United States Patent
Shen et al.

(10) Patent No.: US 11,439,132 B2
(45) Date of Patent: Sep. 13, 2022

(54) HUMANIZED TRANSGENIC ANIMAL

(71) Applicant: Biocytogen Pharmaceuticals (Beijing) Co., Ltd., Beijing (CN)

(72) Inventors: Yuelei Shen, Beijing (CN); Chaoshe Guo, Beijing (CN); Yanan Guo, Beijing (CN); Yang Bai, Beijing (CN); Rui Huang, Beijing (CN); Lei Zhao, Beijing (CN); Xiaofei Zhou, Beijing (CN); Meiling Zhang, Beijing (CN); Jiawei Yao, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/089,479

(22) Filed: Nov. 4, 2020

(65) Prior Publication Data

US 2021/0068379 A1 Mar. 11, 2021

Related U.S. Application Data

(63) Continuation of application No. PCT/CN2020/072714, filed on Jan. 17, 2020.

(30) Foreign Application Priority Data

Jan. 17, 2019 (CN) .......................... 201910044180.6
Jul. 9, 2019 (CN) .......................... 201910616231.8

(51) Int. Cl.
*A01K 67/027* (2006.01)
*C07K 14/525* (2006.01)
*C07K 14/54* (2006.01)
*C07K 14/715* (2006.01)

(52) U.S. Cl.
CPC ........ *A01K 67/0278* (2013.01); *C07K 14/525* (2013.01); *C07K 14/54* (2013.01); *C07K 14/7155* (2013.01); *A01K 2217/072* (2013.01); *A01K 2227/105* (2013.01)

(58) Field of Classification Search
CPC .......... A01K 67/0278; A01K 2217/072; A01K 2227/105; C07K 14/525; C07K 14/54; C07K 14/7155
USPC ................ 800/13, 18, 21; 530/351
See application file for complete search history.

(56) References Cited

U.S. PATENT DOCUMENTS

| 4,683,195 | A | 7/1987 | Mullis et al. |
| 5,869,286 | A | 2/1999 | Yao et al. |
| 9,565,841 | B2* | 2/2017 | Wang ................. A01K 67/0278 |
| 2006/0270003 | A1* | 11/2006 | Arnott ..................... A61P 11/02 435/69.52 |
| 2007/0196371 | A1* | 8/2007 | Kuestner ................. A61P 17/02 424/144.1 |
| 2007/0197441 | A1* | 8/2007 | Rixon ..................... A61P 17/02 514/200 |
| 2013/0254907 | A1* | 9/2013 | Zhu ..................... C12N 15/8509 800/9 |
| 2017/0218092 | A1 | 8/2017 | Chiu et al. |

FOREIGN PATENT DOCUMENTS

| CN | 103387955 | 11/2013 |
| CN | 103642828 | 3/2014 |
| CN | 106470545 | 3/2017 |
| CN | 108424928 | 8/2018 |
| WO | WO 2018/119001 | 6/2018 |

OTHER PUBLICATIONS

UniProtKB/Swiss-Prot. Accession No. AC-Q96F46 (2002)-human IL-17RA.*
Fischer et al. (2015) Arth.&Rheum., vol. 67(1), 51-62. doi.org/10.1002/art.38896, pp. 1-19.*
Li, "Fibroblast Growth Factor 21 Anti-Rheumatoid Arthritis Research," Science and Technology Literature Press, Jun. 2017, p. 84-86 (English abstract).
De Oliveira et al., "Humanized mouse model of skin inflammation is characterized by disturbed keratinocyte differentiation and influx of IL-17A producing T cells," PloS one, Oct. 19, 2012 7(10): 14 Pages.
GenBank Accession No. NG_0280257.1 "*Homo sapiens* interleukin 17 receptor A (IL7RA), RefSeqGene (LRG_355) on chromosome 22," Dec. 14, 2017, 1-12.
GenBank Accession No. NG_033021.1 "*Homo sapiens* interleukin 17A (IL17A), RefSeqGene (LRG_1223) on Chromosome 6," May 30, 2018 1-5.
GenBank Accession No. NP_055154.3 "Interleukin-17 receptor A isoform 1 precursor [*Homo sapiens*]" Jan. 22, 2018, 3 Pages.
GenBank Accession No. AAB99730.1 "IL-17 receptor [*Homo sapiens*]," Jan. 30, 1998, 2 pages.
GenBank Accession No. AAC50341.1 "IL-17 [*Homo sapiens*]," Jan. 16, 1996, 1 Pages.
PCT International Search Report and Written Opinion in International Appln. No. PCT/CN2020/072714, dated Jul. 23, 2020, 24 pages with translation.
Gaffen, "Structure and signalling in the IL-17 receptor family," Nature Reviews Immunology, Aug. 2009, 9(8):556-567.
Hogan et al., "Manipulating the Mouse Embryo: A Laboratory Manual," 1986, Cold Spring Harbor Laboratory Press, 4 Pages.
Toy et al., "Cutting edge: interleukin 17 signals through a heteromeric receptor complex," The Journal of Immunology, Jul. 1, 2006, 177(1): 5 pages.
Zhu et al., "Humanising the mouse genome piece by piece," Nature communications, Apr. 23, 2019, 10(1):1-13.
GenBank Accession No. AAA36758.1 "tumor necrosis factor precursor [Homo sapiens]," Aug. 3, 1993, 1 pages.
International Preliminary Report on Patentability in International Appln. No. PCT/CN2020/072714, dated Jul. 29, 2021, 19 pages.

(Continued)

*Primary Examiner* — Anne Marie S Wehbe
(74) *Attorney, Agent, or Firm* — Fish & Richardson P.C.

(57) ABSTRACT

Provided are a humanized transgenic non-human animal, especially a rodent, in particular a transgenic mouse containing a human interleukin 17A (IL-17A) gene, a human gene 17RA (IL-17RA) and/or a human TNF-alpha gene, and a preparation method therefor and the use thereof.

14 Claims, 32 Drawing Sheets

Specification includes a Sequence Listing.

(56) References Cited

OTHER PUBLICATIONS

GenBank Accession No. NG_007462.1 "Homo sapiens tumor necrosis factor (TNF), RefSeqGene on chromosome 6," Oct. 27, 2019, 6 pages.
GenBank Accession No. NP_002181.1 "interleukin-17A precursor [Homo sapiens]," Nov. 3, 2019, 3 pages.

* cited by examiner

SEQUENCE LISTING

<160> NUMBER OF SEQ ID NOS: 66

<210> SEQ ID NO 1
<211> LENGTH: 1171
<212> TYPE: DNA
<213> ORGANISM: Mus musculus

<400> SEQUENCE: 1

```
atccacctca cacgaggcac aagtgcaccc agcaccagct gatcaggacg cgcaaacatg      60
agtccaggga gagcttcatc tgtgtctctg atgctgttgc tgctgctgag cctggcggct     120
acagtgaagg cagcagcgat catccctcaa agctcagcgt gtccaaacac tgaggccaag     180
gacttcctcc agaatgtgaa ggtcaacctc aaagtcttta actcccttgg cgcaaaagtg     240
agctccagaa ggccctcaga ctacctcaac cgttccacgt caccctggac tctccaccgc     300
aatgaagacc ctgatagata tccctctgtg atctgggaag ctcagtgccg ccaccagcgc     360
tgtgtcaatg cggagggaaa gctggaccac cacatgaatt ctgttctcat ccagcaagag     420
atcctggtcc tgaagaggga gcctgagagc tgccccttca ctttcagggt cgagaagatg     480
ctggtgggtg tgggctgcac ctgcgtggcc tcgattgtcc gccaggcagc ctaaacagag     540
```

```
acccgcggct gaccccctaag aaaccccccac gtttctcagc aaacttactt gcatttttaa    600
aacagttcgt gctattgatt ttcagcaagg aatgtggatt cagaggcaga ttcagaattg    660
tctgccctcc acaatgaaaa gaaggtgtaa aggggtccca aactgcttcg tgtttgtttt    720
tctgtggact ttaaattatt tgtgtattta caatatccca agatagcttt gaagcgtaac    780
ttatttttaat gaagtatcta cattattatt atgtttcttt ctgaagaaga caaaattcaa    840
gactcagaaa ttttattatt taaaaggtaa agcctatatt tatatgagct atttatgaat    900
ctatttattt ttcttcagta tttgaagtat taagaacatg attttcagat ctacctaggg    960
aagtcctaag taagattaaa tattaatgga aatttcagct ttactatttg tttatttaag   1020
gttctctcct ctgaatgggg tgaaaaccaa acttagtttt atgtttaata acttttttaaa   1080
ttattgaaga ttcaaaaaat tggataattt agctccctac tctgttttaa aaaaaaattg   1140
taacaatatc actgtaataa taaagttttg g                                    1171

<210> SEQ ID NO 2
<211> LENGTH: 158
<212> TYPE: PRT
<213> ORGANISM: Mus musculus

<400> SEQUENCE: 2

Met Ser Pro Gly Arg Ala Ser Ser Val Ser Leu Met Leu Leu Leu Leu
1               5                   10                  15

Leu Ser Leu Ala Ala Thr Val Lys Ala Ala Ile Ile Pro Gln Ser
            20                  25                  30

Ser Ala Cys Pro Asn Thr Glu Ala Lys Asp Phe Leu Gln Asn Val Lys
        35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155

<210> SEQ ID NO 3
<211> LENGTH: 1871
<212> TYPE: DNA
<213> ORGANISM: Homo sapiens

<400> SEQUENCE: 3
gtccatctca tagcaggcac aaactcatcc atccccagtt gattggaaga aacaacgatg     60
actcctggga agacctcatt ggtgtcactg ctactgctgc tgagcctgga ggccatagtg    120
aaggcaggaa tcacaatccc acgaaatcca ggatgcccaa attctgagga caagaacttc    180
ccccggactg tgatggtcaa cctgaacatc cataaccgga ataccaatac caatcccaaa    240
aggtcctcag attactacaa ccgatccacc tcaccttgga atctccaccg caatgaggac    300
cctgagagat atccctctgt gatctgggag gcaaagtgcc gccacttggg ctgcatcaac    360
```

-continued

```
gctgatggga acgtggacta ccacatgaac tctgtcccca tccagcaaga gatcctggtc    420
ctgcgcaggg agcctccaca ctgccccaac tccttccggc tggagaagat actggtgtcc    480
gtgggctgca cctgtgtcac cccgattgtc caccatgtgg cctaagagct ctggggagcc    540
cacactcccc aaagcagtta gactatggag agccgaccca gcccctcagg aaccctcatc    600
cttcaaagac agcctcattt cggactaaac tcattagagt tcttaaggca gtttgtccaa    660
ttaaagcttc agaggtaaca cttggccaag atatgagatc tgaattacct ttccctcttt    720
ccaagaagga aggtttgact gagtaccaat ttgcttcttg tttactttt taagggcttt     780 aagttattta tgtatttaat atgccctgag ataactttgg ggtataagat tccattttaa    840
tgaattacct actttatttt gtttgtcttt ttaaagaaga taagattctg ggcttgggaa    900
ttttattatt taaaggtaa aacctgtatt tatttgagct atttaaggat ctatttatgt     960
ttaagtattt agaaaaaggt gaaaaagcac tattatcagt tctgcctagg taaatgtaag   1020
atagaattaa atggcagtgc aaaatttctg agtctttaca acatcggat atagtatttc    1080 ctcctctttg tttttaaaag ttataacatg gctgaaaaga aagattaaac ctactttcat   1140
atgtattaat ttaaattttg caatttgttg aggttttaca agagatacag caagtctaac   1200
tctctgttcc attaaaccct tataataaaa tccttctgta ataataaagt ttcaaaagaa   1260
aatgtttatt tgttctcatt aaatgtattt tagcaaactc agctcttccc tattgggaag   1320
agttatgcaa attctcctat aagcaaaaca aagcatgtct ttgagtaaca atgacctgga   1380
aatacccaaa attccaagtt ctcgatttca catgccttca agactgaaca ccgactaagg   1440
ttttcatact attagccaat gctgtagaca gaagcatttt gataggaata gagcaaataa   1500
gataatggcc ctgaggaatg gcatgtcatt attaaagatc atatggggaa aatgaaaccc   1560
tccccaaaat acaagaagtt ctgggaggag acattgtctt cagactacaa tgtccagttt   1620
ctcccctaga ctcaggcttc cttttggagat taaggcccct cagagatcaa cagaccaaca   1680
tttttctctt cctcaagcaa cactcctagg gcctggcttc tgtctgatca aggcaccaca   1740
caacccagaa aggagctgat ggggcagaac gaactttaag tatgagaaaa gttcagccca   1800
agtaaaataa aaactcaatc acattcaatt ccagagtagt ttcaagtttc acatcgtaac   1860
cattttcgcc c                                                        1871
```

<210> SEQ ID NO 4
<211> LENGTH: 155
<212> TYPE: PRT
<213> ORGANISM: Homo sapiens

<400> SEQUENCE: 4

```
Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95
```

```
Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 5
<211> LENGTH: 3708
<212> TYPE: DNA
<213> ORGANISM: Mus musculus

<400> SEQUENCE: 5
```

| | |
|---|---|
| tagtactcat tactgggact tcccatcata gaattgttca gagtggtcct cagaagcaca | 60 |
| aattataggt aagactgagt taaaatgtag atctggataa gatcctagct ttaccaattc | 120 |
| cataaggcct cccatgtggt cattattgca aataccctcc taccttaaca acaaatcttt | 180 |
| cctttaagtg tcaatttggg attttttttcc agtccaggtt gggcatcttc atacagtagc | 240 |
| tcctacattt aggacctaag gacactttct ctagaactgt tctctattaa acaaaaccaa | 300 |
| tggagaagga gccttatgca atactgtaca atgcattaaa ctaaatggca cctacctgtt | 360 |
| caaacagcca ttgtcttctt taaattagga tgcatgttaa ccactttaaa ctgtgaaatc | 420 |
| cctcctttt acagaccact gctgttattg ctttttcctg aaaagggcca tagaatacaa | 480 |
| attagtgaaa taatagattc tcaatggtag ccctgccatc tgagcagaaa acaaaactga | 540 |
| tttttatgtt tttagtaacg tcttaatttt ccaccacact gagacaaaag atattttatc | 600 |
| ctgtttacaa aagtaagaat tttcccttat ttttggtgtt atcctctctt ataggtagaa | 660 |
| aataatactg tataatggcc taatgatttc aagaagcccc aaagtatctt ttcccttaaa | 720 |
| acatcacttg actacaagca tcctcctgtt tcataccctc ccacacacag ccctggtcct | 780 |
| taaactgtag ctgcccagtc ttgtagctgc tgttttgaat ctgcagagaa gcaagatgga | 840 |
| tacacttgaa ggccactcct gagcaaaatc atcattccta acctactgct tttgtttatt | 900 |
| cattgctatt ttccttctgc aaaaagtcaa ccacaatgaa caggtgagac aaaacctcat | 960 |
| tttataaaac agaagagcat gtctacaaaa aagatgaagt aggtctcaga aaggcaaagg | 1020 |
| cacaacgaaa gtgaagatgc caatctcttg gtaccctcag cacaccaggt ctcactatgg | 1080 |
| ccttccttct gcctctgaag gctaagagcc aatcctgaat aacagcaagc acaaaagaaa | 1140 |
| cctgaccttc tgtgcacagc ccctgtgttc ccaattgctc ctccaaggac aaggctttca | 1200 |
| gatggaggga gtctctatgg ctgggaaatc cgttcttctc aaagccaggc acagccagct | 1260 |
| ccatgtctaa atcttcacac tgttgtgaaa actgatcttg tctctccccc ttccctttat | 1320 |
| ttttagacaa agattgtcac ctctcaaagg cccatacata ggctgagttt tacgactgtg | 1380 |
| ggacagtgga ctggggagat tattagatct tcctcttcat catcagttga cagatttggc | 1440 |
| aggaaacctc ttcctctcct gccagatagc aacaaggagt gtttattcct tggagttcag | 1500 |
| cataggctac aacatagtca tacacttttc aaaggcataa ggatttagag ccaagggata | 1560 |
| agacaaccca ggaatgtctt agactgcagc tgagttctaa aaagaaacaa ggtcatgaat | 1620 |
| ttctgacata atgtttcata ttgccaatca ataacaacaa caacaacaaa agttcagctg | 1680 |
| ttattttcta aaccctatgc agttggtaca aagattaaca aaatagctac aggtgttcaa | 1740 |
| gtaacttaca atatagaaag taaatcagta agcaaacaat atacaggtca agagaaacag | 1800 |

```
acagccacat accaaagaga caaatgagtc taaagtaatc catggagctg agagatggc     1860 tcagcagtta agagtactga ctgctcttcc agaggtcttg agttcaattc cagaaaacca    1920
catggtggct cacaaccatt tgtaatggga tctgatacct tcttctggtg tgtctgaaga    1980
tagcatcagt gtattcacat atattaaata aataaatatt ttttaaaaag taatccatga    2040
agacctatgt tgtataaaaa gttatattat gtacaacaaa atttaagaaa atgagtaaca    2100
cattagccca taaagaagcc aatgttgtgg tatgtttatt ccagtgatgt tattccccga    2160
tagaataact atttgaatag gatcctacaa gtgtgctgat aaacagggtg aaagaggaca    2220
ttgcctaggc tgtattttaa cagaaggtat gtaatttgta gaaggatgac acgtagaaag    2280
ccaggacctg gtgaacccta acatggagca tagtaacatg gaggctagaa gggatgttaa    2340
ttcaaactgc aatactaatt caaggagttc atgcttctca ttcaggaagc tagagaatgg    2400
gaaaagacct ggcaatcaga ggtgtgtgtg agcattatcc cagggataat gccaagggta    2460
ttatcccaag ggtatcccaa gaagtgtcag aaaagcaaac atgatccaaa caggtgaaag    2520
tcagagttac cagccagcaa aagacctaga agaagagca aggtgtgagg tgctgcaact    2580
tctgagaaca cggtgatcat gaacagaatc cagcaatcct accagacatg ccatctattg    2640
aacaggagct atcggtccac ctcatgctgc atgtcagaca aaagctgaag agctgggacc    2700
taatgacccc catattcacc atcttgtcct catatctgct attcctgaag aaaaagactt    2760
ctcaaagaca taaaggcaaa ggtcatctca tggagaggag agaacatgag agagctgttt    2820
ccatcttccc ttctcatccc tcatctcctc ctgttagtag tctccacccg gcagtgcctc    2880
agtgtctcca ctgtctttca gccttcatct tgatttctaa ttctttcttc gatttatcca    2940
atcagtccct tattctttca cttcatttcc ttcctcctta aaagaaaggc ttgataccga    3000
acctcaaaac agcaaatatt aacaggtttc ttgataacat gcaaccgtaa tgacttcact    3060
agtaaacctc atgtctctcg ctactcctta ataactaact agcctttgtg attgtttctt    3120
gcagagaata gacattcaag gaaaaacagt tgcggtactc agttaaatag aacgtgttcc    3180
gttggtgtta aattatttat tttgtatgtc tgtttacata ctaagacatt gagtgggttt    3240
ctttgggcaa gggatgctct ctagccaggg aatttggtag aaaagtgaga agatcaagt    3300 caaaattcaa agtgtgtgtc actaggagac tgtcaagaga ctcacaaacc attactatgg    3360
agcccagctc tgcagcagct tcagatatgt ccatacacac atgatactga atcacagcaa    3420
agcatctctg ttcagctccc aagaagtcat gcttcttgc atagtgaact tctgcccttc    3480
ccatctacct tcgagacaga tgttgcccgt cataaagggg tggttctgtg ctgacctcat    3540
ttgaggatgg aatctttact caaatggtgt caccccccaa cccactcttg acgtaagtga    3600
ccacagaggt agtaaaaccg tataaaaaga gagaaaggag cactactctt catccacctc    3660
acacgaggca caagtgcacc cagcaccagc tgatcaggac gcgcaaac                 3708
```

<210> SEQ ID NO 6
<211> LENGTH: 4765
<212> TYPE: DNA
<213> ORGANISM: Mus musculus

<400> SEQUENCE: 6

```
atctgtagct cggggaacat catgagagag gagcagaaag attgtaagag cagaacaaca     60
ggaagtctgc tggaaacag tctcctagaa atgtcttcat gaacaagcca agacaatatc    120
aatggatata ttaacatgga aggggtaatt tcctcaggtc ctaccctaa acaaagaact     180 acaggcatcc attgacttct gggagaatgt aaaagcctct accagagatg agccccttat    240
```

-continued

| | |
|---|---|
| tgtttgccta atgcagagca gtcagccctg aaaccatatg cacaacaaca acaaaaatgg | 300 |
| actcagcagg ttgtgagtgc atgtgtgtgt gtgtgtatgt gtatgcaaac acatacatgt | 360 |
| gcatatacat gtatgtggca ataataaaga aaaatactat catttaagag tggaggtata | 420 |
| tggaaggggt tcaaggaaga gtgggtctgg aggaagaaag ggaagtggaa aatgacatga | 480 |
| ttctatctgt accaaaaaaa acactttttt aaaatgtaat atgttgagtc ccccaggaag | 540 |
| tagggaggtc tggtggggtg ggaggaatgc aatgaagaac tgtcagaagg tagaccagaa | 600 |
| gggggataat gaccagactg taaaaagag attaagaaa ataaatttta taaataaata | 660 |
| aattaattaa ttgattgatt gattccaaca aaaatagtat attttacacg attataaatt | 720 |
| tgtggtaatt gtacatgaat aatagaaatt tgtgactgca caaatttgga tttcaatcct | 780 |
| ggctttcctt attcgctgct ccctgagaaa tatttctaag cctcttccct cttaatccat | 840 |
| gaaatagaaa actgtgagag taaaacataa ataaataaag aatggcgtag tctctgatag | 900 |
| gtgtcagtag agaaggacac atacagcctt ctcccctgtc agtcttccct aaaacaatgc | 960 |
| ggcagtgcag atgtttgcac agggtcacat tctgtgagat actgtaagta ttacagatga | 1020 |
| gtttcagcac aatggaagga tggagggagg ttacatgcaa acaccactat cttatgcaag | 1080 |
| gagatgagcg tctgcagact ttgatatgtg ggagggactg tcctgttact cacctcaaac | 1140 |
| actctgaagg tcttttgaac ttcagcccct tcagctctcc cctgttggga aaaatatgcc | 1200 |
| tcagagtaac aatgcccttg aaccacccaa ctccacattt ccaatttcat attgccttta | 1260 |
| agacaatgag gacaaggctc ttcccgtacc aggcaatgct atgagcagaa gcattctgca | 1320 |
| ataaattaag caaaagaac agtggcccta ggaaaagaca catcgctgtt agagaccggg | 1380 |
| gtgggggggg gggggcgtc ctaaaactat aacctgatat ttgacataaa agaaattctt | 1440 |
| caaggaaact ctgttttcaa aataggagtc cttgctgtga tgaccaaggg ccaccagaga | 1500 |
| tcaggattcc ctctcagagc ttaggtctgc cctcagtctc tcatccagtg cacccaagca | 1560 |
| ttcagaaggg aagcggcaag aaagagtcag cctcaagaat aaaagttgtt caacacaagc | 1620 |
| aaagtcaaaa ctgagtcata tttgccaaca ggtcagtttc aagctttgaa tcatagccat | 1680 |
| cccagtcccc acgcccgagc ctgttattat gcccagttca gggatccttc tgaatggttc | 1740 |
| tccagccatt cccacgggct ctctgcttct tcttttaatt aatttctttg ggaagaggaa | 1800 |
| gcaggcacct ttagctgctg agctgtctca ttagccttca ctctttactc tctagcaggt | 1860 |
| ccatcaccac ccagaggtct acagtacagc ttccctctcc ttcattctaa tcccaaagcc | 1920 |
| aggaggcaac ttccccagtt cctcttgtca ctagcacctt gtgctctttc agcttggtac | 1980 |
| tgagagccaa cgcgtcacaa gcacacacgc acacacacag ccactgtagt ggtttgaatg | 2040 |
| tgcctggccc agtgagtggc actattagga gatgtggcct tgttggagtg ggtgtggcct | 2100 |
| tgttagagaa agtgtgtcac tgtgggcatg agctttaaga ccctcatccc agcttcattg | 2160 |
| gaagacagtc ttctagcggc cttcagatga agatgtagaa ctcgcagctc ctccagcatt | 2220 |
| atgccatgct cccaccttga tgataataga ctgaatctct gaacctgtaa gccagtccca | 2280 |
| attaaacgtt gtccttacaa gagttgcctt ggtcatgtgt ctgttcacag cagtaaaatt | 2340 |
| ctaagacaca cacacatatg cgcatggggg ggaggggag agagagagag agcattcaca | 2400 |
| ggtgctatct taatgtttta taatcctgct gctcatcatt tctttgggct tcgcagcatg | 2460 |
| gaagctttag gagcaccact aaggaagagc acacatgaac ctgtagtccc agaccgttat | 2520 |
| ttcatattag ttttactatt attggaggct aggaaaaagc cttctgtctt aggatttttg | 2580 |
| ttgttgttgt tgttgttgtt tgtttgtttg tttgtttgtt tttttagtgt tgttataact | 2640 |

```
gtaacaaaaa ttttgaattc tgtttattaa gaaaagagat ttatttcact gacagttcta    2700
gagttgatgg ccattgcacc tgcatcctgc atcagtgtag cttctggtca aggcttcatg    2760
gcaaatgtca tccacataaa gaaacatgtc ctaaagtggc atagagagga ggtaccaggc    2820
tcttctagaa cagcccatct gtcaggacag tcccatgaga cctggtctgc tctctaatga    2880
cagtactgat ctctcccaac agtgattcct tctacaacta aattaccttg cactaggtct    2940
aactctttaa agctgtaagc acttcaaacc caccacaatg gagaccgagt atccagcagt    3000
ggatatttag agaccttatt ggatactttt ttgttttttc tttttctagg aattcaatgg    3060
tgtgttattt tagtgtactt tatttattca ctttacatcc caatcacagc ccccccccaa    3120
cctgtcatcc ccctcctcc ctgcttctct tctcctctag aaggatggag gggtcccctg    3180
ggcatccact ccccaccctg gcacatcaag tctctgaaag gctaggtgct tcctctccca    3240
ctgaggccag acaaaacagc ccagctagaa gaacatatcc cacagacagc caactgcttt    3300
gaggatagct cccgttccag ttgttcagga cccacatgaa gaccaagctg cacatctgct    3360
acatatgaac agggaggcct aggtccagtc catgtatgct tttttgttgg tagttcagtc    3420
cctgagaccc tccaagggtc caggttaatt gactgtgttg gtcttcctgt ggagttccta    3480
tccccttcag gctgaaatcc tttcttctgt tcttctataa gagcccagga gctccatcta    3540
ctgtttgtct gaagctccac aacctctcca acagtgctg taagctagtc attaaatgct    3600
taaagatgca cctacagggg acagttcaca gaacaatctt cgcatctct cattccctga    3660 tacacatcac ttggattcta actttgtctt cccaactctc accattgctc tggatggttt    3720
ccatgcgcct gcagatgcta cctacacaca aagtcaaagg ccacaaagta ctgtctggtt    3780
tacctcacgc cactttctgc ataggtatgt tctaagtgca gtgaggttca cagcctgtgc    3840
actggggctc ctctgctgga atggcttaac cttctttcc tagttgttcc tagttgctcc    3900 tcttttttt cacagattta tttatttatt tattatta tttatttatt tattgtacgt    3960
gagtacactg tcactctatt cagagacacc agaaattaca ttacagatgt ctgtgagcca    4020
ccatgtggtt gctgggattt gaactcggga cctctggtta agagctactg ctcttaaccg    4080
ctgagctatc tctccagccc tgctagctct tctttatatt catagccttc ctttccttcc    4140
tgctatacct taaccctatt ttgtgatgaa agcatgtggc aaaggaaaca aaatgagaga    4200
gaataagagt ctgaggtcgc agccccttca agggtctgcc cacaaaagcc ttactgcctt    4260
ctattaggtc tcatctgcta aaggttccac ctcctcccac tatcactaaa ggctaggaac    4320 caaacccta acatgcagcc cttcagaaaa cactggccaa acaacatca tgcctggatt    4380 tgttcattct tacccactca tttcaagctc aatgctttgc cttatacaac aaaactcttc    4440
ccttcatatt cacaagggct tcacatcctt aggatccatg ttttgtgtct tttgctacct    4500
ttctcaagat gctctgtgga gacagggagt gattagaaga cctcatagat gggcccagac    4560
gaccaagagt ggttgctaat gcccctatct cagagtatcc atgatggagc aggatttaat    4620
gagaggcatt gaagaattgc cttcacaagc tgtgtaacta ggttttttctc cactgaagca    4680 aacccaactg accaaatgca gtttatgtcc tttctcagca cagagccaca gagtatggat    4740
ccaatgtgac agaaaccggt cagtg                                          4765
```

<210> SEQ ID NO 7
<211> LENGTH: 2861
<212> TYPE: DNA
<213> ORGANISM: Homo sapiens

```
<400> SEQUENCE: 7
atgactcctg ggaagacctc attggtggtg agtcctgcac taacgtgcga tgctcttgct      60
gatttggacc agatagtatt tctggaccgt gggcatgaaa cgctgggttc tgactatgga     120
gatccaggaa tactgtatat gtaggatagg aaatgaaagc tttggtaggt atttaagtca     180
ttgtgcagca ttttcaagaa ctgatacaca gcagtttgaa agataagatt aaaactgaaa     240
gatagctata ttggggctaa accacacaag aagtgtcaca tgatgctgtg cagtaagaaa     300
gaaaatttat tgaaagtctg tttttctgag tacaaaggat ttaatataat tctcccacgg     360 cattttctt taaaatgggt cactatcctt gagattttga agccgtagc agcaacaacc       420 tttgttcca ttatctcgta ccatattctc agtacattga actatgtat tctaactaaa       480 cataggtata actgtgtttt agaataagtg gggtttatat tttttaaata tttaacttca     540 agtatcttt ttgaaatctg attttattac agaatcaata catgttaaat ttagaacaac      600
tggaaaatat acctaagaaa acatgaagga gatcgagttt ttagttggat gcctgccagt     660
agcaccaaca gcacttctag catgaatatt gataccacat agatttttcta tagctctttc   720 ttccaatgtg aatgtttgac ttcacgatga gtttcacaga atatgggact gagaacaatg    780
gtgcaggagg atatttctac ctagaaaatc aaggttatta ttccttccca gacctgacaa    840
tgatgcatgt gctgataggc taatgacatg ccatgacttg acatttttat taaaattatt    900
gccaaccaat ggataacatg tcttttcctaa gtcaaaagga gaatgttgaa actagttttt   960
ttaaaaaaat tttaaagcca tggtgttaac attatgttgg tcatctacct agattttttct  1020 ctagctgatc tgaaaaatgt agtatagatt gtcctggaac attgtgtgtt ctctatgatt   1080
agcaatgcat catcatcaca attaattttgt caaaaagaac cacatagtaa tctaatctcc   1140
aacctctctc tccttttccca ttcaattcta gtcactgcta ctgctgctga gcctggaggc  1200
catagtgaag gcaggaatca caatcccacg aaatccagga tgcccaaatt ctgaggacaa   1260
gaacttcccc cggactgtga tggtcaacct gaacatccat aaccggaata ccaataccaa   1320
tcccaaaagg tcctcagatt actacaaccg atccacctca ccttggaatc tccagtacgt   1380
aaagcttcca gataaaaatg ctatattctt catccctctt atgcatcaga ctgccagtta   1440
aatctccctg aggatgattt tattcattta gaattaccag tcaaacctgg aaggaccact   1500
gtgaagagca attctcaaac tttctacaga tttcttaaac caagcacagg acagcctcca   1560
ataatcccta tcctgttaga tctaattgtc actgacacca ataatcaacc caaattaatt   1620
ataatcatta ttctaatatt tatgagaccc caagtctatt ctttatttat tcaaagaata   1680
gacatttatc aaagaggatt aatgcttta ttatcttaac cagagctgcc attgagaaga     1740
tttattgcaa ataattaata attagggttt tttacttta ttcttttgct tatttttgtt    1800
tttgaatccc agtggaataa gtatcactgg ggtatttcta cccctttgtg tgttaaatag    1860
tcttgatcta cttcctaaca tacctatgct gctgtatcc ttagtatacc cagtatttag    1920
accccatcaa gggttaaata ccaaatgtat tttgatcatt tgacttcata caaataagtc    1980
tctgttctgt ggagcctaca gattggtctg attgtaggat ttcttctctt cttcccatta    2040
ctaggaagag tcaaaataaa tcaattcaaa aatgcaagca atcattcac tgatctaaaa     2100 gagagaggga agagaaggtc atagagacac ttaacctttt gtttccagcc ctttatctca    2160
gctctgggct ctgtcccacg aatgtgatct cagataaaat tttgatgtat tccctcttca   2220
aagacagact tcatcaagtc aaataaacag ctatcttatt ctagatggtt ccaagtctac    2280
tcttcctttg gtcttcttct gtctgtcaaa tgtaccctaa aaaagctatc atttgtgtca    2340
```

```
aacttaaatt ttttctgtgg cctcagtcta tcttatttta ttcattcttc aaataaattg   2400
gagaaaaact gatcactgtc ttcttttcta taacaattca cgtgcttgaa aaaaaaatcc   2460
aatttgtccc caaagttctt cttcaaacta acatcattta aagaatttgc aatgcctata   2520
atttgtcatc ctgtgaactt gcctctcttc atgtattcct gttttatttc tttcccactt   2580
taccaggaat tcactttcct cctgattttt ctcccctctg cagccgcaat gaggaccctg   2640
agagatatcc ctctgtgatc tgggaggcaa agtgccgcca cttgggctgc atcaacgctg   2700
atgggaacgt ggactaccac atgaactctg tccccatcca gcaagagatc ctggtcctgc   2760
gcagggagcc tccacactgc cccaactcct tccggctgga agatactg gtgtccgtgg   2820 gctgcacctg tgtcaccccg attgtccacc atgtggccta a                       2861

<210> SEQ ID NO 8
<211> LENGTH: 60
<212> TYPE: DNA
<213> ORGANISM: Artificial Sequence
<220> FEATURE:
<223> OTHER INFORMATION: Junction sequence

<400> SEQUENCE: 8
gcacccagca ccagctgatc aggacgcgca aacatgactc ctgggaagac ctcattggtg   60

<210> SEQ ID NO 9
<211> LENGTH: 50
<212> TYPE: DNA
<213> ORGANISM: Artificial Sequence
<220> FEATURE:
<223> OTHER INFORMATION: Junction sequence

<400> SEQUENCE: 9
cgattgtcca ccatgtggcc taaacagaga cccgcggctg acccctaaga               50

<210> SEQ ID NO 10
<211> LENGTH: 83
<212> TYPE: DNA
<213> ORGANISM: Artificial Sequence
<220> FEATURE:
<223> OTHER INFORMATION: Junction sequence

<400> SEQUENCE: 10
ccggtggaca catctggagt acagcgtctg cgtcgacggt atcgataagc ttgatatcga   60
attccgaagt tcctattctc tag                                           83

<210> SEQ ID NO 11
<211> LENGTH: 81
<212> TYPE: DNA
<213> ORGANISM: Artificial Sequence
<220> FEATURE:
<223> OTHER INFORMATION: Junction sequence

<400> SEQUENCE: 11
agtataggaa cttcatcagt caggtacata atggtggatc cactagtatc tgtagctcgg   60
ggaacatcat gagagaggag c                                             81

<210> SEQ ID NO 12
<211> LENGTH: 26
<212> TYPE: DNA
<213> ORGANISM: Artificial Sequence
<220> FEATURE:
<223> OTHER INFORMATION: Synthetic primer
```

<400> SEQUENCE: 12
cttctgatac atatgcatcc acgtgc        26

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
atgcccacgg tccagaaata ctat        24

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
gctcgactag agcttgcgga        20

<210> SEQ ID NO 15
<211> LENGTH: 25
<212> TYPE: DNA
<213> ORGANISM: Artificial Sequence
<220> FEATURE:
<223> OTHER INFORMATION: Synthetic primer

<400> SEQUENCE: 15
gtgagagcag caagtgctct taacc        25

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
agagcagcat accaattagc aacat        25

<210> SEQ ID NO 17
<211> LENGTH: 23
<212> TYPE: DNA
<213> ORGANISM: Artificial Sequence
<220> FEATURE:
<223> OTHER INFORMATION: Synthetic primer

<400> SEQUENCE: 17
ctaggtgggt tcctcactgg tct        23

<210> SEQ ID NO 18
<211> LENGTH: 27
<212> TYPE: DNA
<213> ORGANISM: Artificial Sequence
<220> FEATURE:
<223> OTHER INFORMATION: Synthetic primer

<400> SEQUENCE: 18
accaaaggaa caagtggaaa gaatcgg        27

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
atcttcctgc ccagcattgc ct                                    22

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
ggatcggcca ttgaacaaga tgg                                   23

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
cagaagaact cgtcaagaag gcg                                   23

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
tctctgttca gctcccaaga agtca                                 25

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
ctcattgcat agcgtcatgt gaca                                  24

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
atgcccacgg tccagaaata ctat                                  24

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

```
<400> SEQUENCE: 25
gaatgtagct agcctgtgca agga                                              24

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26
cagcagactt cctgttgttc tgctc                                             25

<210> SEQ ID NO 27
<211> LENGTH: 25
<212> TYPE: DNA
<213> ORGANISM: Artificial Sequence
<220> FEATURE:
<223> OTHER INFORMATION: Synthetic primer

<400> SEQUENCE: 27
gacaagcgtt agtaggcaca tatac                                             25

<210> SEQ ID NO 28
<211> LENGTH: 24
<212> TYPE: DNA
<213> ORGANISM: Artificial Sequence
<220> FEATURE:
<223> OTHER INFORMATION: Synthetic primer

<400> SEQUENCE: 28
gctccaattt cccacaacat tagt                                              24

<210> SEQ ID NO 29
<211> LENGTH: 3970
<212> TYPE: DNA
<213> ORGANISM: Mus musculus

<400> SEQUENCE: 29
gggggagccg gaagcgggac agaggaggcc gtgtgaagcc gacgagcgcc agtcctcggc        60
cgggaaagcc atcgcgggcc ctcgctgtcg cgcggagcca gctgcgagcg ctccgcgacc       120
gggccgaggg ctatggcgat tcggcgctgc tggccacggg tcgtcccgg gcccgcgctg        180 ggatggctgc ttctgctgct gaacgttctg gccccgggcc gcgcctcccc gcgcctcctc       240
gacttcccgg ctccggtctg cgcgcaggag gggctgagct gcagagtcaa gaatagtact       300
tgtctggatg acagctggat ccaccccaaa aacctgaccc cgtcttcccc aaaaaacatc       360
tatatcaatc ttagtgtttc ctctacccag cacggagaat tagtccctgt gttgcatgtt       420
gagtggaccc tgcagacaga tgccagcatc ctgtacctcg agggtgcaga gctgtccgtc       480
ctgcagctga acaccaatga gcggctgtgt gtcaagttcc agtttctgtc catgctgcag       540
catcaccgta agcggtggcg gttttccttc agccactttg tggtagatcc tggccaggag       600
tatgaagtga ctgttcacca cctgccgaag cccatccctg atgggaccc aaaccacaaa       660 tccaagatca tctttgtgcc tgactgtgag gacagcaaga tgaagatgac tacctcatgc       720
gtgagctcag gcagcctttg ggatcccaac atcactgtgg agccttgga cacacagcat       780 ctgcgagtgg acttcaccct gtggaatgaa tccacccct accaggtcct gctggaaagt       840
ttctccgact cagagaacca cagctgcttt gatgtcgtta acaaatatt tgcgcccagg       900 caagaagaat tccatcagcg agctaatgtc acattcactc taagcaagtt tcactggtgc       960
```

```
tgccatcacc acgtgcaggt ccagcccttc ttcagcagct gcctaaatga ctgtttgaga    1020
cacgctgtga ctgtgccctg cccagtaatc tcaaatacca cagttcccaa gccagttgca    1080
gactacattc ccctgtgggt gtatggcctc atcacactca tcgccattct gctggtggga    1140
tctgtcatcg tgctgatcat ctgtatgacc tggaggcttt ctggcgccga tcaagagaaa    1200
catggtgatg actccaaaat caatggcatc ttgcccgtag cagacctgac tcccccaccc    1260
ctgaggccca ggaaggtctg gatcgtctac tcggccgacc accccctcta tgtggaggtg    1320
gtcctaaagt tcgcccagtt cctgatcact gcctgtggca ctgaagtagc ccttgacctc    1380
ctggaagagc aggttatctc tgaggtgggg gtcatgacct gggtgagccg acagaagcag    1440
gagatggtgg agagcaactc caaaatcatc atcctgtgtt cccgaggcac ccaagcaaag    1500
tggaaagcta tcttgggttg ggctgagcct gctgtccagc tacggtgtga ccactggaag    1560
cctgctgggg accttttcac tgcagccatg aacatgatcc tgccagactt caagaggcca    1620
gcctgcttcg gcacctacgt tgtttgctac ttcagtggca tctgtagtga gagggatgtc    1680
cccgacctct tcaacatcac ctccaggtac ccactcatgg acagatttga ggaggtttac    1740
ttccggatcc aggacctgga gatgtttgaa cccggccgga tgcaccatgt cagagagctc    1800 acagggggaca attacctgca gagccctagt ggccggcagc tcaaggaggc tgtgcttagg    1860
ttccaggagt ggcaaaccca gtgccccgac tggttcgagc gtgagaacct ctgcttagct    1920
gatggccaag atcttccctc cctggatgaa gaagtgtttg aagacccact gctgccacca    1980
gggggaggaa ttgtcaaaca gcagcccctg gtgcgggaac tcccatctga cggctgcctt    2040
gtggtagatg tctgtgtcag tgaggaagaa agtagaatgg caaagctgga ccctcagcta    2100
tggccacaga gagagctagt ggctcacacc ctccaaagca tggtgctgcc agcagagcag    2160
gtccctgcag ctcatgtggt ggagcctctc catctcccag acggcagtgg agcagctgcc    2220
cagctgccca tgacagagga cagcgaggct tgcccgctgc tgggggtcca gaggaacagc    2280
atcctttgcc tccccgtgga ctcagatgac ttgccactct gtagcacccc aatgatgtca    2340
cctgaccacc tccaaggcga tgcaagagag cagctagaaa gcctaatgct ctcggtgctg    2400
cagcagagcc tgagtggaca gccccctggag agctggccga ggccagaggt ggtcctcgag    2460
ggctgcacac cctctgagga ggagcagcgg cagtcggtgc agtcggacca gggctacatc    2520
tccaggagct ccccgcagcc ccccgagtgg ctcacggagg aggaagagct agaactgggt    2580
gagcccgttg agtctctctc tcctgaggaa ctacggagcc tgaggaagct ccagaggcag    2640
cttttcttct gggagctcga gaagaaccct ggctggaaca gcttggagcc acggagaccc    2700
accccagaag agcagaatcc ctcctaggcc tcctgagcct gctacttaag agggtgtata    2760
ttgtactctg tgtgtgcgtg cgtgtgtgtg tgtgtgtgtg tgtgtgtgtg cgtgtgtgtg    2820
tgtgtgtgtg tgtgtgtgtg tgtgtagtgc ccggcttaga aatgtgaaca tctgaatctg    2880
acatagtgtt gtatacctga agtcccagca cttgggaact gagacttgat gatctcctga    2940
agccaggtgt tcagggccag tgtgaaaaca tagcaagacc tcagagaaat caatgcagac    3000
atcttggtac tgatccctaa acacacccct ttccctgata acccgacatg agcatctggt    3060
catcattgca caagaatcca cagcccgttc ccagagctca tagccaagtg tgttgctcat    3120
tccttgaata tttattctgt acctactatt catcagacat ttggaattca aaaacaagtt    3180
acatgacaca gccttagcca ctaagaagct taaaattcgg taaggatgta aaattagcca    3240 ggatgaaatag agggctgctg ccctggctgc agaagaaccc gagagagcct gcgggtggcg    3300
tctgggcaag aggggagtgg cctgtggatt gagtattagg aaggagccag agctcagggt    3360
```

```
ggagagagct ctgtggggct agggtgggag cagctgggga ctcctctcat gagtggatct    3420
gttgccctac gggggaggaa acttcatgcc aaatataccc agaagtcttc tcagatcagt    3480
tctttagaaa gagctggtat agaaatgggt gatgtaaaac ttgagaagca ggaagaggcg    3540
tgtgaaatcc tgtgctctct caagtgctgg ctgccagtcc gtgggagggc tgcggcatgt    3600
gattcttcat gggctgcagc caccagatcc ctggagagct ctacctcggg gtacagtgag    3660
ggagttgaga aagatgtgag ggtagtgggc atggggggcgt ggcataacag agaactcgg    3720 gaggccctca aggtcagagg aaagtatgtc actgtataac tacagtaaga gaggttgttt    3780
aaagtagctc cagggcgccc tcatggggca gacagcagcc ttgtggcgta ggttctagag    3840
aatgcacagg tcttcctaga cttaggtgag aaaaggacca tgaaatgctg tgggaagcac    3900
gaattcagtg attgtgtgtg tgcatatgtg tgtgcagtaa tgaagactta ataaagttgc    3960
tgtattggta                                                          3970
```

<210> SEQ ID NO 30
<211> LENGTH: 864
<212> TYPE: PRT
<213> ORGANISM: Mus musculus

<400> SEQUENCE: 30

```
Met Ala Ile Arg Arg Cys Trp Pro Arg Val Val Pro Gly Pro Ala Leu
1               5                   10                  15

Gly Trp Leu Leu Leu Leu Asn Val Leu Ala Pro Gly Arg Ala Ser
            20                  25                  30

Pro Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Lys Asn Leu Thr Pro Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255
```

Gln Glu Glu Phe His Gln Arg Ala Asn Val Thr Phe Thr Leu Ser Lys
                260                 265                 270

Phe His Trp Cys Cys His His His Val Gln Val Gln Pro Phe Phe Ser
        275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp Val Tyr Gly Leu Ile Thr Leu Ile Ala Ile Leu Leu Val Gly
                325                 330                 335

Ser Val Ile Val Leu Ile Ile Cys Met Thr Trp Arg Leu Ser Gly Ala
            340                 345                 350

Asp Gln Glu Lys His Gly Asp Asp Ser Lys Ile Asn Gly Ile Leu Pro
        355                 360                 365

Val Ala Asp Leu Thr Pro Pro Leu Arg Pro Arg Lys Val Trp Ile
    370                 375                 380

Val Tyr Ser Ala Asp His Pro Leu Tyr Val Glu Val Val Leu Lys Phe
385                 390                 395                 400

Ala Gln Phe Leu Ile Thr Ala Cys Gly Thr Glu Val Ala Leu Asp Leu
                405                 410                 415

Leu Glu Glu Gln Val Ile Ser Glu Val Gly Val Met Thr Trp Val Ser
            420                 425                 430

Arg Gln Lys Gln Glu Met Val Glu Ser Asn Ser Lys Ile Ile Ile Leu
        435                 440                 445

Cys Ser Arg Gly Thr Gln Ala Lys Trp Lys Ala Ile Leu Gly Trp Ala
450                 455                 460

Glu Pro Ala Val Gln Leu Arg Cys Asp His Trp Lys Pro Ala Gly Asp
465                 470                 475                 480

Leu Phe Thr Ala Ala Met Asn Met Ile Leu Pro Asp Phe Lys Arg Pro
                485                 490                 495

Ala Cys Phe Gly Thr Tyr Val Val Cys Tyr Phe Ser Gly Ile Cys Ser
            500                 505                 510

Glu Arg Asp Val Pro Asp Leu Phe Asn Ile Thr Ser Arg Tyr Pro Leu
        515                 520                 525

Met Asp Arg Phe Glu Glu Val Tyr Phe Arg Ile Gln Asp Leu Glu Met
530                 535                 540

Phe Glu Pro Gly Arg Met His His Val Arg Glu Leu Thr Gly Asp Asn
545                 550                 555                 560

Tyr Leu Gln Ser Pro Ser Gly Arg Gln Leu Lys Glu Ala Val Leu Arg
                565                 570                 575

Phe Gln Glu Trp Gln Thr Gln Cys Pro Asp Trp Phe Glu Arg Glu Asn
            580                 585                 590

Leu Cys Leu Ala Asp Gly Gln Asp Leu Pro Ser Leu Asp Glu Glu Val
        595                 600                 605

Phe Glu Asp Pro Leu Leu Pro Pro Gly Gly Gly Ile Val Lys Gln Gln
610                 615                 620

Pro Leu Val Arg Glu Leu Pro Ser Asp Gly Cys Leu Val Asp Val
625                 630                 635                 640

Cys Val Ser Glu Glu Glu Ser Arg Met Ala Lys Leu Asp Pro Gln Leu
                645                 650                 655

Trp Pro Gln Arg Glu Leu Val Ala His Thr Leu Gln Ser Met Val Leu
            660                 665                 670

```
Pro Ala Glu Gln Val Pro Ala His Val Val Glu Pro Leu His Leu
        675                 680                 685

Pro Asp Gly Ser Gly Ala Ala Gln Leu Pro Met Thr Glu Asp Ser
    690                 695                 700

Glu Ala Cys Pro Leu Leu Gly Val Gln Arg Asn Ser Ile Leu Cys Leu
705                 710                 715                 720

Pro Val Asp Ser Asp Asp Leu Pro Leu Cys Ser Thr Pro Met Met Ser
                725                 730                 735

Pro Asp His Leu Gln Gly Asp Ala Arg Glu Gln Leu Glu Ser Leu Met
            740                 745                 750

Leu Ser Val Leu Gln Gln Ser Leu Ser Gly Gln Pro Leu Glu Ser Trp
        755                 760                 765

Pro Arg Pro Glu Val Val Leu Glu Gly Cys Thr Pro Ser Glu Glu Glu
    770                 775                 780

Gln Arg Gln Ser Val Gln Ser Asp Gln Gly Tyr Ile Ser Arg Ser Ser
785                 790                 795                 800

Pro Gln Pro Pro Glu Trp Leu Thr Glu Glu Glu Leu Glu Leu Gly
                805                 810                 815

Glu Pro Val Glu Ser Leu Ser Pro Glu Glu Leu Arg Ser Leu Arg Lys
            820                 825                 830

Leu Gln Arg Gln Leu Phe Phe Trp Glu Leu Glu Lys Asn Pro Gly Trp
        835                 840                 845

Asn Ser Leu Glu Pro Arg Arg Pro Thr Pro Glu Glu Gln Asn Pro Ser
    850                 855                 860

<210> SEQ ID NO 31
<211> LENGTH: 8608
<212> TYPE: DNA
<213> ORGANISM: Homo sapiens

<400> SEQUENCE: 31
ctgggcccgg gctggaagcc ggaagcgagc aaagtggagc cgactcgaac tccaccgcgg      60
aaaagaaagc tcagaacgt tcgttcgctg cgtccccagc cggggccgag ccctccgcga     120
cgccagccgg gccatggggg ccgcacgcag ccgccgtcc gctgtcccgg ggcccctgct     180
ggggctgctc ctgctgctcc tgggcgtgct ggccccgggt ggcgcctccc tgcgactcct     240
ggaccaccgg gcgctggtct gctcccagcc ggggctaaac tgcacggtca agaatagtac     300
ctgcctggat gacagctgga ttcaccctcg aaacctgacc cctcctcccc aaaggacct      360
gcagatccag ctgcactttg cccacaccca acaaggagac ctgttccccg tggctcacat     420
cgaatggaca ctgcagacag acgccagcat cctgtacctc gagggtgcag agttatctgt     480
cctgcagctg aacaccaatg aacgtttgtg cgtcaggttt gagtttctgt ccaaactgag     540
gcatcaccac aggcggtggc gttttacctt cagccacttt gtggttgacc ctgaccagga     600
atatgaggtg accgttcacc acctgcccaa gccatccct gatggggacc caaaccacca     660
gtccaagaat ttccttgtgc ctgactgtga gcacgccagg atgaaggtaa ccacgccatg     720
catgagctca ggcagcctgt gggaccccaa catcaccgtg gagaccctgg aggcccacca     780
gctgcgtgtg agcttcaccc tgtggaacga atctacccat taccagatcc tgctgaccag     840
ttttccgcac atggagaacc acagttgctt tgagcacatg caccacatac tgcgcccag      900
accagaagag ttccaccagc gatccaacgt cacactcact ctacgcaacc ttaagggtg      960
ctgtcgccac caagtgcaga tccagccctt cttcagcagc tgcctcaatg actgcctcag    1020
acactccgcg actgtttcct gcccagaaat gccagacact ccagaaccaa ttccggacta    1080
```

```
catgcccctg tgggtgtact ggttcatcac gggcatctcc atcctgctgg tgggctccgt    1140
catcctgctc atcgtctgca tgacctggag gctagctggg cctggaagtg aaaaatacag    1200
tgatgacacc aaatacaccg atggcctgcc tgcggctgac ctgatccccc caccgctgaa    1260
gcccaggaag gtctggatca tctactcagc cgaccacccc ctctacgtgg acgtggtcct    1320
gaaattcgcc cagttcctgc tcaccgcctg cggcacggaa gtggccctgg acctgctgga    1380
agagcaggcc atctcggagg caggagtcat gacctgggtg ggccgtcaga agcaggagat    1440
ggtggagagc aactctaaga tcatcgtcct gtgctcccgc ggcacgcgcg ccaagtggca    1500
ggcgctcctg ggccgggggg cgcctgtgcg gctgcgctgc gaccacggaa agcccgtggg    1560
ggacctgttc actgcagcca tgaacatgat cctcccggac ttcaagaggc cagcctgctt    1620
cggcacctac gtagtctgct acttcagcga ggtcagctgt gacggcgacg tccccgacct    1680
gttcggcgcg cgccgcggt acccgctcat ggacaggttc gaggaggtgt acttccgcat    1740
ccaggacctg gagatgttcc agccgggccg catgcaccgc gtaggggagc tgtcggggga    1800
caactacctg cggagcccgg gcggcaggca gctccgcgcc gccctggaca ggttccggga    1860
ctggcaggtc cgctgtcccg actggttcga atgtgagaac ctctactcag cagatgacca    1920
ggatgccccg tccctggacg aagaggtgtt tgaggagcca ctgctgcctc cgggaaccgg    1980
catcgtgaag cgggcgcccc tggtgcgcga gcctggctcc caggcctgcc tggccataga    2040
cccgctggtc gggaggaag gaggagcagc agtggcaaag ctggaacctc acctgcagcc    2100
ccggggtcag ccagcgccgc agcccctcca caccctggtg ctcgccgcag aggaggggc    2160
cctggtggcc gcggtggagc ctgggcccct ggctgacggt gccgcagtcc ggctggcact    2220
ggcgggggag ggcgaggcct gcccgctgct gggcagcccg ggcgctgggc gaaatagcgt    2280
cctcttcctc cccgtggacc ccgaggactc gcccttggc agcagcaccc ccatggcgtc    2340
tcctgacctc cttccagagg acgtgaggga gcacctcgaa ggcttgatgc tctcgctctt    2400
cgagcagagt ctgagctgcc aggcccaggg gggctgcagt agaccgcca tggtcctcac    2460
agacccacac acgccctacg aggaggagca gcggcagtca gtgcagtctg accagggcta    2520
catctccagg agctccccgc agcccccga gggactcacg gaaatggagg aagaggagga    2580
agaggagcag gacccaggga agccggccct gccactctct cccgaggacc tggagagcct    2640
gaggagcctc cagcggcagc tgcttttccg ccagctgcag aagaactcgg gctgggacac    2700
gatggggtca gagtcagagg ggcccagtgc atgagggcgg ctccccaggg accgcccaga    2760
tcccagcttt gagagaggag tgtgtgtgca cgtattcatc tgtgtgtaca tgtctgcatg    2820
tgtatatgtt cgtgtgtgaa atgtaggctt taaaatgtaa atgtctggat tttaatccca    2880
ggcatccctc ctaactttttc tttgtgcagc ggtctggtta tcgtctatcc caggggaat    2940
ccacacagcc cgctcccagg agctaatggt agagcgtcct tgaggctcca ttattcgttc    3000
attcagcatt tattgtgcac ctactatgtg gcgggcattt gggataccaa gataaattgc    3060
atgcggcatg gccccagcca tgaaggaact taaccgctag tgccgaggac acgttaaacg    3120
aacaggatgg gccgggcacg gtggctcacg cctgtaatcc cagcacactg ggaggccgag    3180
gcaggtggat cactctgagg tcaggagttt gagccagcct ggccaacatg gtgaaacccc    3240
atctccacta aaaatagaaa aattagccgg gcatggtgac acatgcctgt agtcctagct    3300
acttgggagg ctgaggcagg agaattgctt gaatctggga ggcagaggtt gcagtgagcc    3360
gagattgtgc cattgcactg cagcctggat gacagagcga gactctatct caaaaaaaaa    3420
aaaaaaaaaa gatggtcacg cgggatgtaa acgctgaatg ggccaggtgc agtggctcat    3480
```

```
gcttgtaatc ccagcacttt gggaaggcga ggcaggtgga ttgcttgagc tcaggagttc    3540
aagaccagcc tgggcgacat agtgagacct catctctacc taaattttt tttagtcagt    3600 catggtggca catgcctgta gtcccagcta ctcgggaggc tgatgccaga tgatcacttg    3660
agcccaggag gtagaggctg cagtgagcta taatggtacc attgcaatcc agcctgggca    3720
gcagagtgag accctgtctc aaaaaaaata aaaagtaga aagatggagt ggaagcctgc    3780
ccagggttgt gagcatgcac gggaaaggca cccaggtcag gggggatccc cgaggagatg    3840
cctgagctga aggattgtgg ttggggaaag cgtagtccca gcaaggaagc agtttgtggg    3900
taagtgctgg gaggtgagtg gagtgagctt gtcagggagc tgctggtgga gcctggaggg    3960
gaaggaggga ggcagtgaga gagatcgggg tgggggtgg ggggatgtcg ccagagctca    4020
ggggtgggga cagccttgtg cgcatcagtc ctgaggcctg gggcaccttt cgtctgatga    4080
gcctctgcat ggagagaggc tgagggctaa acacagctgg atgtcacctg agttcattta    4140
taggaagaga gaaatgtcga ggtgaaacgt aaaagcatct ggcaggaagg tgagtctgaa    4200
gccctgcacc cgcgttccga ctatcagtgg ggagctgtta gcacgtagga ttcttcagag    4260
cagctgggct ggagctcccc tgagctcagg aagcccagg gtgcaagggc aaggaaatga    4320
ggggtggtgg gtcagtgaag atctgggcag accttgtgtg gggaaggggt gctgctgtga    4380
cttcagggtc tgaggtccaa agacagcatt tgaaagagg ctctgaagcc agtgtttgaa    4440
gaatttgttc ctgaagtacc tcctgggggt aggctagagg cttctggctt cagggtcctg    4500
aagaacacat tgaggtgccg tctgacactg aataggggtg cccttcattc ctatgcctga    4560
gtccttaact atatttccaa cctccagtga ggaggagaag attcggaaat gtgacaggag    4620
agcaaacagg acagtttgca tgtgtgtgtg cgcacacata catgtgcgtg aaagattatc    4680
aataaaagtg cataaatttg ttgatctggt aagagtttct agcaggaagg tcgagccact    4740
tactgtaggt caagaagttg ctagttgcgg agttttttct tgcagttaga ctttacctag    4800
tggtagcagg gccaccaaag ctctgtgtcc cagatggtgt atggcccata atccacccaa    4860
cagcagcaaa ggaccaggca aaggagaaca ggagcagaag cctcccagcc actagccttt    4920
tgggctcagt ctctccaata atcctggaga ggggcttcgt tgggtctgga cacctaccat    4980
gcattctgtg accttttccct agcttccaat aaataactgt ttgacgccca gagtacagga    5040
taccacaatg cactcttcct gcgtagagca catgttccca tctgctccca ttcctcagga    5100
accttgaatt ctagctctgc tggcctttga gcccatgcca gtaaatgtcc tgatgggcat    5160
tgcctactat ctccagggca gctgcctttg tcctcctaac agctttattg gagtacagtt    5220
cacttaccat acaatccaca attgaccctg cacaatttga tgccggttta gtatagtcac    5280
agttcagcag ccatcagcac agtcagtctt agagtttact accccaaaa gaaatccagc    5340 ccccccttagt caccaccccca acctccccat ccctaggcac ccctaggcta ctttgatctc    5400
tgtagacttg cctcttctgg acatgacata gagaaaggag tcataaattc tccaaggtgt    5460
ctgtttcttc tttaatgtca ttccctgttt ctcctcacat tccctcccca tttcctgggc    5520
ccagtctcac actggtcctt gcttacccta aatgctatta attccatcac tctgagtatg    5580
gtgtttgctg tccgctgaat gccaagagct tcaagagtgt gtgtaaataa agccacacct    5640
ttatttttgt attattctga accatggcta ataaattgtt tcaccaagaa atgtctctct    5700
aagaacaggt gccctccacg ctgtgcccct cccacctctt cagctcgtct cctgagtgtg    5760
cagaggtggt tccggttggg aaagaagcag cggagcatct aaccatgcct gtgtccaggc    5820
cgattatgca cgcagccacc aacaagctcc caactcccgc gtagagtttc atgactttt    5880
```

```
cctgcctact atcttgatcc tagttttttt tttgttttt ttttttttaa ggaataatta    5940
ctttgattca aaaccagttt ctcttttctg cataggaagg tccttgaagg tgtttagggt    6000
ctaaaaaggg tggtgttcgg tctctgaaac atccattcag cagtttgagc tgggatctct    6060
gaatgcaagg gtatgatgga tatacttctt tcttgctttt gttgtgtttt ggttttttgt    6120
ttgttttaa gtcagggtct ctctgtcacc aggctgtatt acagtggtgc aatcatggct    6180
cactgcagcc tcgacctccc aggctcaagc catctttcca cctcagcctg ccagtggcta    6240
gaactacagg cgtgcaccac tgtgcccggc taatttgtgt gtatatattt tgtagaaatg    6300
gggtttcacc atgttgtcca ggctggtcac gaactcctgg gctcaagcca tctgcccgcc    6360
tcatcctccc aaagtgctgg gattataggc ctgagcccac cgtgcctggc ctttcctgtt    6420
tatctttgaa aattaaatag gcataagag agaagaagat gtacttacaa tgcagtgggt    6480
ggttttaact ctatagcctt tgggctctgt ggttggtgct ccccttccta aataaatgag    6540
gtgtatgcag ggccctcttc tgccttagcg ccctgccagc tgggactcca gcaaggcccg    6600
gggcacctga ggacagagtg agatggaggg ccgctgctcc agcagccggg cctgcatccc    6660
acaagtcaac tgtgtcggac agaggatcct tacaaagaag aggcagcagg ttgggggct    6720
ggccagctgc tcgtccgccc taggtagctt gctcatctgt aaagtgggtg gggcaggagt    6780
tcccacctca tggggtcctg gcaagcctgc agtatccccg agtggcacca gcctgcttct    6840
ggggcagagc agtttgtgcc ccctgaggta ccactgatcc tctttccctg ctattaggta    6900
ttgctctctt cctccggtgt ttgccttttc agattataga agtaatatgt gttcccatat    6960
ttggcgtctc tcaggagctc aggaagtact tggctgagtg aacatgtcca ttgtggaaaa    7020
atggcaacaa tatggattcc atgggtatat tttatagaag aatatgaaga aaagcagcta    7080
cccctaaacc cattgcacaa gctgttcatg ttaattctgt acccgacgct ttccccacgg    7140
ggcctcccct cactctgaaa tggcatccag gtccatcttg ccctccacct ctgcatggct    7200
ctccatgccc catcgcctct cccagatcct agcactgggt ccacactctc gcccctgtcca    7260
tttaggttga tgaaagcagg cagtcacccg ggtgggccag tcttgcctgt gggaggaaca    7320
tgcagtctcc tgtctcatgg tttgaagtgt gccaggaagc ctggcccagc ccacctcccc    7380
ctggagtcct tcccaggagg aataacccct taggtcattg actataagat gagttcgctc    7440
actggatcct tcctctctga tgagacagga agaaggtaca cagtgaccag gtaggaggag    7500
gagagggagt agaaaggagg gatgcgggtg gctggtccct gcatttgcct gcttccctgc    7560
acgggtgtcc cactggccgc ctctgctcac cagtgtcatg ggattctctc agaagatgaa    7620
aacagcccct gctttttgc tagaatggct gagctttcat ggaaaggaag ctggacccaa    7680
gcaacagccg actaccgaag gttgcctgga gcagtgcaga tgtgggagga agaagggcct    7740
tggtgcacac tggcttttct tcctgactgc aatgtggcat tgtgccagct acctcctctt    7800
tctcggcctc aggaaaatgg agagaaagca gccctgaagg tggctgtgac gagggaaggg    7860
gcagagggcc tgacagtcaa ccacgcgcta tattttcctg ttcttcctta gggcaagaac    7920
tgcatggcca gactcaggca aggcctaggt gtgggctggg cattgcctac acgtgaagag    7980
atcactccgc gtccctactg cacctgtcac aaagtgcctt ctgatatgcc tggcaaacca    8040
aaatcggtga gcgccagctt gcttccctag aagacatttc taaatattca taacatgctt    8100
gctcaaatca atcaccttat tttacatccg ctccagggag aaatgaagac atggtcctac    8160
gttgttctgt aattatttc tatgtaaatt ttgttccttg ttacaattat atatgtctta    8220
ggggaaagga ccatttcaca tgtgtcacct catgtgattc tcaccacagc cctgtgattg    8280
```

```
ctcctgtttt ataaataatg acatagttcc agttgatggc caaagccaca gctaacgaga      8340
ggcagagaga gctcaggctc ccaggagctt ccactctcag accttgcctc ccgggctgcc      8400
ctgagtgaaa cgcctgctta gcatttggca cagccagaag cagcaagcta gggtcacaac      8460
acagagaggg gctgtgtaat actggctgcc tctgtgctaa gaaaaaaaaa aaatcactgt      8520
gtgtttgttt attttggtgc aggcccagtg ttcttgctta gacttaatac taccccttcat     8580 gttaaaataa aaccaaacaa aaacccat                                          8608

<210> SEQ ID NO 32
<211> LENGTH: 866
<212> TYPE: PRT
<213> ORGANISM: Homo sapiens

<400> SEQUENCE: 32

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320
```

-continued

```
Val Tyr Trp Phe Ile Thr Gly Ile Ser Ile Leu Leu Val Gly Ser Val
            325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
            355                 360                 365

Asp Leu Ile Pro Pro Leu Lys Pro Arg Lys Val Trp Ile Ile Tyr
370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
            405                 410                 415

Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
            450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
            485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
            515                 520                 525

Phe Glu Glu Val Tyr Phe Arg Ile Gln Asp Leu Glu Met Phe Gln Pro
            530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
            565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
            595                 600                 605

Pro Leu Leu Pro Pro Gly Thr Gly Ile Val Lys Arg Ala Pro Leu Val
            610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
            645                 650                 655

Arg Gly Gln Pro Ala Pro Gln Pro Leu His Thr Leu Val Leu Ala Ala
            660                 665                 670

Glu Glu Gly Ala Leu Val Ala Val Glu Pro Gly Pro Leu Ala Asp
            675                 680                 685

Gly Ala Ala Val Arg Leu Ala Leu Ala Gly Glu Gly Glu Ala Cys Pro
            690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
            725                 730                 735
```

```
Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
    770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
    850                 855                 860

Ser Ala
865

<210> SEQ ID NO 33
<211> LENGTH: 4547
<212> TYPE: DNA
<213> ORGANISM: Mus musculus

<400> SEQUENCE: 33
```

| | | | | | |
|---|---|---|---|---|---|
| gcagttcagt | attagctgct | gtcataatct | cttcatcatt | ctgaatattc | tgtgatttct | 60 |
| ccaagatggc | taacaatgcc | attcaatggt | attcgtcttg | tttgattgct | tggttggtag | 120 |
| gttggttggt | ttggttttgt | tttttaagag | ggtttctctc | ttgtagacca | ggctggcctt | 180 |
| gaacagaggg | ccactagaga | gacactgagg | tttttgtttt | aaagagcata | ttttgtactc | 240 |
| accttcaacc | ccaggactca | gtccctgagt | ttgaggccag | cgtggtctac | agagcgagtg | 300 |
| tacagcaggg | ctgtataaag | aatgagtatc | cttcatagag | tatgagtgtc | cttctgtttg | 360 |
| ggggaaggag | tggttggttg | gtgttggtgc | ctggggccgt | acagggcgag | catgcgtgca | 420 |
| tttatgctgt | tgggattgaa | cctaggtcgt | acatgtcctt | aaacatttcc | tagtgactta | 480 |
| ccccttagtc | ccaggaatag | ggcttctgaa | aggattaagg | agacagctgg | ggagcaaatc | 540 |
| acgggcagaa | caagatctat | attagtagtg | tccaacgatg | ataccaaatg | cattttatat | 600 |
| taagaagatt | tacaggggct | gttggtggtt | cactgggtaa | aggtgctggc | caccatacct | 660 |
| cacaacctga | gttcaatccc | tgggaccaac | aaagtgaaag | gaaagaacca | actcctgaaa | 720 |
| gttatctccc | ggcctctctg | tatgtgtgcc | tgtgtgcatc | acacacacaa | taataaaaaa | 780 |
| tgaaaaaaaa | aagttgtagg | gactgagaga | cttagtgggt | aagctcttgc | taagcaagca | 840 |
| tgaaagcctg | tgttcagatt | tctaccgacc | acaagccagg | tgtagcagct | gtgcctataa | 900 |
| ccccagtgtc | agaggacaga | aacaagtgga | tcctgagggc | tcactggcca | tcttagaaca | 960 |
| ctgagttcca | aattcactga | gaggccttgt | ctcaaaagaa | taaggtagag | aaagaccctg | 1020 |
| tctcagaaca | agacaaggta | gagaaactac | aggggaggcg | ccttgacctc | aacctccggc | 1080 |
| tcccacacac | ctgcacacaa | gtacatgtgc | atacctcaac | atcagtgcaa | attctatatt | 1140 |
| gaaattaaat | tataaataaa | ataaatagaa | ggtggaatag | atggctcagt | ggttaaggat | 1200 |
| actgtctggt | cttccagagg | accagcgttc | aattcccagc | caccatatcg | tggctcacaa | 1260 |
| ctacttataa | ttccaacttc | aagggatcct | gcttccattt | ctaacttctt | ctggcatgca | 1320 |

```
aatggtacac agatacacat gcaggcaaaa caccaggcac atagaatata tattttttaa      1380
ttttaaagaa gcatatgtct cttccccaaa taatattctc atttgctcac ctctttttt       1440 ttttttttt ttttggtttt tcgagacagg gtttctctgt gtagccctgg ctgtcctggt      1500
actcactttg tagaccaggc tggcctcaaa ctcagaaatc cgcctgcctc tgcctcccta      1560
gtgctgggat taaaggcgtg cgccaccaag ctcggcgctt atctcatttt taaatctttt      1620
gtttagatta atatcataaa ctttcatctt taaattcatt tttaaatttt atttatttac      1680
atcctaaatg ttgcccctca aagattttt taaatattta tttacttaat gtatatgggt      1740
gcactgtcgc tgtcttcaga cacaccagga gagggcattg aatcccatta cagatggttt      1800
tcagccacca tgtggttgct gcccctcaaa gatttattaa ttaattttac atatatgagt      1860
gctctacctg cttgtacgcc tgcaaaccag aagagggcat cacatcccaa tatagatggt      1920
tgtgagccaa catgtggtag ctgggagttg aactcaggac ctctggtaga gcagacagtg      1980
ctcttaactg ctgagccatc tctccagctc tttaaattcg tttttattaa gtaatgtagg      2040
gattcctttt ttaaaattgt actgggatat ttaaaacagc tccctaagtc acactcaagc      2100
ctgctcccca aaggcaggca cttataatgg acttgtttgt ttcttttgac acctatgttt      2160
tcgcagtgtg ccttttact caccccgggt aatagaggaa acatcacttg ctccagatct      2220
ctgctttccc attacatttg tatcatggtt tgattttcag cttcctgttg ttacagcaag      2280
gcagctgttg tctctagtga ggcaagagat gcactttgat aaacatttt ctggtagtta      2340 ctcccctctc cccttcacag atgatcacac atccaactat taacaagcaa gactgaaact      2400
gtagggcttg aagtatcaag ctatttctgt cagttgtagc aagctagtca gccaagtgtt      2460
tccaaacccc tcccacttcc tcctcttgtc aggataggta gcatcttgcc ctggatttta      2520
agtagcttct gatgggtaag aaagagggag tcccccaaat gcagtatagc tgctgttgtt      2580
tctgtaagag tcccagtccc aggagcagtt tctgtcctgt gtcccagttc acaggagtgc      2640
tggatgggaa gagaggagca ggcttgtagg acttaatctc agaacatggt atgctgtgtg      2700
tctgtgggaa cgagcagaga catcgagata ggtcttgttt tacacctgca aggaccattt      2760
ggcaggctgt gatgttagcc cagggcagtg aaggacagtt agtcacaaag aactgggaga      2820
cgtacgtgaa gtctggaccc caagagcatg tgaactggtg ccccaaacag gtaggaagga      2880
cacagatgaa atagtaggct cagaatggat cctggcatga tatcatcctg tggcctattt      2940
tatgaatgaa ccctgaggca tcacatcgcc gagtcctgca ctctgctccc tctggagaga      3000
cagctgtcaa tcagtgtcca tcctagacac agtgcggtac tgtgcacccg tcatccaggc      3060
cttgcctctg ctgcacatca gcttcatggg atggtgtggg ccaatctggg tagttcaggc      3120
ctggaagtca cagaacttga attccagagc ttccttgcta tcttgccagc agtgacagtc      3180
actccttaga gtcccagatt ccagctctag aggatgtccc ctatcacttg tgacagagat      3240
tggcagtgtt gccagtgaac tatgcataat gagtcagggt ttcatgacta agtcagagtt      3300
ctgtggcatt tcctaaactg atggccagtc tgagaacacc agcccagtgt ttacagtgtt      3360
tgtgaagcag aagtgagaag tgaaggtctg tttcatcatc tcccatatcc acttcctgcc      3420
ctgcgtcttt actcctgtgg ttagtttaat ttccagcaat agtgtgaagt tggtgttaga      3480
gtattctgat ttttaaaaa agatttattt attttatgta tgtatgagta cactgttagc      3540
tgtactgatg gttgtgagct atcatgtggt tgctgggaat ttgaattcag gacctctgct      3600
cgctctggtt gaccccactt gctctggtcg gctctgctct ctccggccta agatttatt      3660 tatttttata tctatatcac tgtcttcaga cacaccagaa gagggtgtca aatctcatta      3720
```

| | |
|---|---|
| cagatggttg tgggcctcta tgtggttgct gggatttgag ctcaggacct tcagaagagc | 3780 |
| agtcagtgct cttaaccact gggccatctt tctagcccaa ctactctgat tttatgttga | 3840 |
| agaaattgag gctttgagta aggtggtgat tcaaccaggg ctctgtgtgt gtgtgtgtgt | 3900 |
| gtgtgtgtgt gtgtgtgtgt gtggcgcata tgtgtggtgt tgtggtgtgt gtgtggtata | 3960 |
| tggtgtgtgt gtgggggggc agaacagtta tttaaacttt tcctaacaag tttataaatt | 4020 |
| tgatgcttca cctctgagga aaattagaaa ccttggaatt ttaagacctt cttttccaga | 4080 |
| caccctctct gttttgtagt ttgttttttgt ttttattatt atttctttttt attgtttcaa | 4140 |
| ttcccagccc ataacagtta ttcagaaagc ctccaagtct agctttgctt ggcagctcat | 4200 |
| gcctttagtt ccggcaatca gggtagtgga gacaagctgt tctctgtgaa ttcaaggtca | 4260 |
| gccaagtcta ggatattctg tcccccaaag atgcgccctc tcccaaagat aaaacgcctc | 4320 |
| cagttctgtt tgctgtctgc ccaccactca cctcctctgc tggacaaaga ggaacaaaag | 4380 |
| tgcagaagac ttttgactac ttggcagcag agcagctccc aaaagtgagc tgggagggag | 4440 |
| acagggactg tgtgaaccgc tctcaggggc ctgccaggca gcggggccac tgggagcctg | 4500 |
| gcccttctca tcggtaatca acacttcctt tcttcccaca ggggctg | 4547 |

<210> SEQ ID NO 34
<211> LENGTH: 3608
<212> TYPE: DNA
<213> ORGANISM: Mus musculus

<400> SEQUENCE: 34

| | |
|---|---|
| tccaccagct ttgtagtcac aggagaccta atcttagatt ccatttcctc ttctgtaaaa | 60 |
| gaggacactc ggacctccac gagtctagag taaccctgct cattccctgt ctactcctgc | 120 |
| cctggctgag tttaacagg gagaaggtgt gttgcctagg ctgaccctgt cctgtgctag | 180 |
| aatggatctt tggtcctctg ggaaacctgc ctccacactt gctgatgttc atccatatca | 240 |
| tggtttatct tgaattgtgg ggtccacaga ttctgggaag ggtcacatga cattccgtgt | 300 |
| gatgtcgaag tgtgtccagc tgctattaca ttttctacgg cttcctcgag tgtccccacc | 360 |
| acagggaaga gaaaaggaga aaactcactc actagtcatt ggagtatctt tgacaatcct | 420 |
| gagcaaaggc ccaaagaaca gggactgaaa ttaagagtct aaatcacttc tttaggaact | 480 |
| gagatgtaac tcaggggtag agcccttgcc caatatgccc aaggccctgg tttccctccc | 540 |
| ggtcactgtc atccaaggag agcaattact taagagtcta gttcccttc tttacttcaa | 600 |
| ggacaccagg aggaggaaat gtcgaaagga ccatgggggc tgctgctgtc aggaagtgtt | 660 |
| gtaagatgtc tgcttcctgc atggactgcc cttccctcca gtggagtctg ctcatagagg | 720 |
| cttgagtggc aggactgcag aaaggggcca gggagtccac cccagctcag gtctgtggct | 780 |
| cccagcctgg agaagccaca gaagaatcca gaccctagct gactgaaggg cccagcactt | 840 |
| cgcacataac cttgagaatg tccctccata gccccactcc tcagaaacaa tggggtgtca | 900 |
| gaggcatcag tccctgttca cctagcttac tggagcagct gacccagggc tcacacctac | 960 |
| acagccacaa gacctgttct ctgcagaggc ccagaaatgt ctagtggtca ctggctggtg | 1020 |
| ttgctccct tgtccacctg tatcattaag cagccgtcca tcagacatct gtgagccctt | 1080 |
| cagttgttgt ttctctttgg aataagccgc tccatagatt tcttttcctt gcaggcgccg | 1140 |
| atcaagagaa acatggtgat gactccaaaa tcaatggtca gtagcgcatg ctctgtgggg | 1200 |
| tctgcctgct ttctgaagcc tgctgggttc ctggggtaga tagatctgtt gtgtctctgg | 1260 |
| tcaaactcct gagtcctttc agaaggccct atccttacgt aggacacaag tctccacctc | 1320 |

```
atacagagag ggctttggga tgctccaaac atccttctta atttaattgc ttagacaaag      1380
aagagaaggt gaacattttt cagggaaaac ccttcctgaa tgggcgtttc tcttccatgg      1440
gcattgtacc tttaattctt ctgatttatt ttgatttatg aggtcccact atgcagcctt      1500
ggctggcctg caactttcta tgtagatcag gcatagagaa ctcctgcctc tgcctcccga      1560
gtgctgggat taaaggggtg caccactatg tctggctttc taccccttt tcatttaaaa       1620 tgatgaaaat atcagccaaa gaccagctgg cgctatgtgg aggagactgg aggcagcgag      1680
gagggaggga gactggttcc tgctcacaca gggcccacac tgcttcctca tatatcacaa      1740
ggcaacatag cagcatctgg tctaccagaa ggctgtttgc cgaaggtaga aagtcagact      1800
ctgccttcag tgcaggtagt tcacaggctg actctggagc cgtggtcctc aaccttccta      1860
atgctgtgac cctttaatac agttcctcat attgtggtga ccccaaccat aaaattatgt      1920
ttgttgttac ttcataatta taactctgct actgtaattc atgacataaa tatctgatat      1980
gcaggctatc tgatatacaa tcctgtgaaa gggccgttca accccgaag ggttaagaac        2040 cgctactcta gagagcaatg cccaggtcca gtccttggca tgaggatcag cacacgtttc      2100
tttgtctctt ccaggcatct tgcccgtagc agacctgact cccccacccc tgaggcccag      2160
gaaggtctgg atcgtctact cggccgacca cccctctat gtggaggtgg tcctaaagtt        2220
cgcccagttc ctgatcactg cctgtggcac tgaagtagcc cttgacctcc tggaagagca      2280
ggttatctct gaggtggggg tcatgacctg ggtgagccga cagaagcagg agatggtgga      2340
gagcaactcc aaaatcatca tcctgtgttc ccgaggcacc caagcaaagt ggaaagctat      2400
cttgggttgg gctgagcctg ctgtccagct acggtgtgac cactggaagc ctgctgggga      2460 cctttcact gcagccatga acatgatcct gccagacttc aagaggccag cctgcttcgg       2520
cacctacgtt gtttgctact tcagtggcat ctgtagtgag agggatgtcc ccgacctctt      2580
caacatcacc tccaggtacc cactcatgga cagatttgag gaggtttact tccggatcca      2640
ggacctggag atgtttgaac ccggccggat gcaccatgtc agagagctca caggggacaa      2700
ttacctgcag agccctagtg gccggcagct caaggaggct gtgcttaggt tccaggagtg      2760
gcaaacccga tgcccgact ggttcgagcg tgagaacctc tgcttagctg atggccaaga       2820
tcttccctcc ctggatgaag aagtgtttga agacccactg ctgccaccag ggggaggaat      2880
tgtcaaacag cagcccctgg tgcgggaact cccatctgac ggctgccttg tggtagatgt      2940
ctgtgtcagt gaggaagaaa gtagaatggc aaagctggac cctcagctat ggccacagag      3000
agagctagtg gctcacaccc tccaaagcat ggtgctgcca gcagagcagg tccctgcagc      3060
tcatgtggtg gagcctctcc atctcccaga cggcagtgga gcagctgccc agctgcccat      3120
gacagaggac agcgaggctt gcccgctgct gggggtccag aggaacagca tcctttgcct      3180
ccccgtggac tcagatgact tgccactctg tagcacccca atgatgtcac ctgaccacct      3240
ccaaggcgat gcaagagagc agctagaaag cctaatgctc tcggtgctgc agcagagcct      3300
gagtggacag cccctggaga gctggccgag gccagaggtg gtcctcgagg gctgcacacc      3360
ctctgaggag gagcagcggc agtcggtgca gtcggaccag ggctacatct ccaggagctc      3420
cccgcagccc cccgagtggc tcacggagga ggaagagcta gaactgggtg agcccgttga      3480
gtctctctct cctgaggaac tacggagcct gaggaagctc cagaggcagc ttttcttctg      3540
ggagctcgag aagaaccctg gctggaacag cttggagcca cggagaccca ccccagaaga      3600
gcagaatc                                                              3608
```

<210> SEQ ID NO 35
<211> LENGTH: 8865
<212> TYPE: DNA
<213> ORGANISM: Homo sapiens

<400> SEQUENCE: 35

| | | | | | |
|---|---|---|---|---|---|
| aactgcacgg | tcaagaatag | taagtcatct | ttttctgttc | ttcttcttgt | tgccttctta | 60 |
| atcaagtgag | agcctgctgc | caacttctga | cagaagtctt | gccatgccac | tccaggttca | 120 |
| ggctgtgagc | tacagccatc | cgcaggaggg | ttcccggaga | attgtggatg | cgtgcacctg | 180 |
| cgcttcctgt | cgagaacatt | cattatgcaa | aagtcaggaa | aggagaaaca | gaactgtcat | 240 |
| ttggattgtg | aaagtattct | ctggggagct | gccctactgt | atctataata | taatttgatt | 300 |
| tgccacagct | tgtcactgta | aagtgagaga | catctgtgct | gttgattttg | ttttgtttta | 360 |
| attcaaagag | gcacatattc | aagtgtctga | gccaattaga | gaccctgac | atataacaat | 420 |
| aaagcagctc | ttactacaac | tgcatccctc | ctgtgccctt | attcccaatc | acaacttctt | 480 |
| ctcaaaatca | acttgtgtac | tttgtcttct | ctcctaaaat | tccctttaga | cttgagaggt | 540 |
| ttgcagtgac | cccagtaaac | attagagaag | agggagcagg | gcagtaaagc | tgaggacgcg | 600 |
| gccaagggcc | acaggctgga | aggccgcggg | ccctgagct | gtttgctgtc | tagctgtctg | 660 |
| tacctgctgc | tggggcatct | cagggtctcg | gctataagtc | tctgaatgtt | gcttttccct | 720 |
| ggctgccagg | tacctgcctg | gatgacagct | ggattcaccc | tcgaaacctg | accccctcct | 780 |
| ccccaaagga | cctgcagatc | cagctgcact | tgcccacac | ccaacaagga | gacctgttcc | 840 |
| ccgtggctca | catcgaatgg | acactgcaga | cagacggtga | gtgggcatgc | cagcagggcc | 900 |
| ctgggggatt | ctccctgcct | ccaagtggct | ctcccagtca | ggctcaggat | tgggctccca | 960 |
| gtcctgtgct | cagacatggg | ggttcaaatt | tagtgctata | aggatccgtc | atttcatgca | 1020 |
| gtcaaatact | tgttcagcat | tttagatatt | aacccacagt | gataccttct | catcacacca | 1080 |
| ttcttcatga | aaggacttcc | ttcaacctaa | tatttttagc | accctgaggg | gaaaaaaaag | 1140 |
| caagcagtta | attttgtgac | tacagtacca | aaaatgaagt | ggaaaatggt | aacacatttg | 1200 |
| tcaacctgtt | ccctgaattt | aggggccagc | acttttaaaa | cgtcccccaa | gcctattcag | 1260 |
| gaatggagag | tttatgttac | agaattggga | cgattgggc | ttatgagcac | tagccccaga | 1320 |
| tttgtgaacg | gggcatgggg | gaagttcttt | ttggaagtcc | ccgccctcag | tgctcctgct | 1380 |
| gacagccaca | acctcgtgag | gatggtgggg | atggctgtgt | ttgacaccca | tgccagattg | 1440 |
| tcaaagccct | caccacaagt | ttgcaaagcc | tttacttcta | gcccagtgta | aagtgtcatt | 1500 |
| tttccttgcc | cagctgggaa | ataactgtct | gcaaggcggt | aggctgaggc | cagagagtga | 1560 |
| actgaaagga | acaggatgtg | gagagttggg | taagacggca | gatttctttt | taggagtgaa | 1620 |
| caaccgcaac | agatagggaa | gtgacacacc | cagcacttgt | cttggctgat | ctgcatctgt | 1680 |
| ttgtcttctc | ttctccctct | cctgcagcca | gcatcctgta | cctcgagggt | gcagagttat | 1740 |
| ctgtcctgca | gctgaacacc | aatgaacgtt | tgtgcgtcag | gtttgagttt | ctgtccaaac | 1800 |
| tgaggcatca | ccacaggcgg | gtaagaacac | agctcctgag | tggattatgt | tccactgatg | 1860 |
| acaccagtac | agacttcttg | tccccaaatt | cagaccctga | tttagagtgg | gggagaccca | 1920 |
| gaggtgctga | gggagtctgt | ggaattcaga | atggcagcct | gagatgggca | gaagtcaaaa | 1980 |
| gagaagtggt | gtggccgccg | tgagcaatag | tgagggacag | agcgtatttt | tgaaagcgtc | 2040 |
| cctcacctgc | tcacccctgg | ttttctcttcc | cactttacct | agctattcgt | tcggaaagga | 2100 |
| agttgaattg | gaaggcagct | tccacagccc | tacctcctgc | catctttgtg | taactttgtg | 2160 |

| | |
|---|---|
| taacatctttt tatgtgtaac ttggattcag ctggggccta ccttcaggaa gaaaaaaccg | 2220 |
| cccagaccaa agaactgctg taggtgggca aatgagcact acaacagctt agtctcattt | 2280 |
| tgctgctcac agctaaatgg tgaaatgttg attcttgttt aagtttgttt aaagcagtgg | 2340 |
| gtctcaaagt gtggtccgta gaccagcagc ctcagcctca cctgggaacg tggtagagat | 2400 |
| gtttggcccc accccagact tcccaggcca gaaactctta gggtggggtc cagcaactgg | 2460 |
| tgcttaaccc ttaagtcatc acgatgcgag ccttagtttg aagactactg gtttaaatct | 2520 |
| gcaaatggtc acttgaaaac aagttagatc tcccacaaac tcaagcagca aaggcagaac | 2580 |
| ccctctccga tgttaaatta ggaccccaa acttgactgc tatgcgaatg gtgagaacca | 2640 |
| ggttcctccg tccacttaga agcaaaggac cccggcccct ccaccagggt aactagaatg | 2700 |
| ggggttggag tcgatgtctg taatctctaa cacccagaaa ataacttagc acaaattcaa | 2760 |
| atatcattgc aactgaggtg cctgctggcc cagggtgagt gggggtctct agcttgtcct | 2820 |
| ttgcaccttt ttactccata atggtctcaa gaggttcctg gcttttccgt ttgaggagga | 2880 |
| agaatcattt gacaaatagt ttttacctgc ctggcgtgtg ccagatctcc atagcccaa | 2940 |
| gtccctggc tccgccctct catacccatt gtcctagaat ttgagagggc aggtgggagg | 3000 |
| ggtgggacta cttccacttt ccccaaattc ttttgcctta ttcactgtct actgatgagg | 3060 |
| ccagatccag gtttaaaaaa aaaaaaaaa aaaacaggca gaaaggacca gaggaaacaa | 3120 |
| aaaacaaaga tactgatttc cctgaccttg gattttgctg tggttgttgc tttgttctta | 3180 |
| tttttggctg aatattcggg agtgggtggg aacgggggtc tttgggcata gatgggtgac | 3240 |
| agaggtgtgt gtaatccatc caccttccct tcctcccttc tcttcagtgg cgttttacct | 3300 |
| tcagccactt tgtggttgac cctgaccagg aatatgaggt gaccgttcac cacctgccca | 3360 |
| agcccatccc tgatggggac ccaaaccacc agtccaagaa tttccttgtg cctggtaaga | 3420 |
| gcatcctccc aagacattcc ctccccaatg gcctctgtga aaggaagca ccaggtggca | 3480 |
| cagatgccag ccccccctgct cagcaagaca ttggctggca ttgccagcac ctgggaccca | 3540 |
| cagaacaaac agaggccaag actgggagtg ctttggtgtg tgctgcaacc tccattccct | 3600 |
| gaggcagagg ccattctctg ttggcacaac agtggacggt ggcccaagat cccaggagtt | 3660 |
| ttatgggaac cagagcacct ccctctatct agagaagcac ccagcctgcc cagaaaatag | 3720 |
| cataaaggca agccacaagc cactcgtggg gaagttgcag cctctgcccc cagcctggtc | 3780 |
| ccagcctccg tggcttgctc ttctccttcc accttacatt ctgcctgcat catccaacgt | 3840 |
| tcatcccatg catggcgctc tactccccat gcctatccac actgcctgtg attaccgcca | 3900 |
| ggcttttctt ctcaggcatc ctttgatgta catgtacctt ctacttctct gtcctcccca | 3960 |
| gaagctcagc tattacctac atttctctct ttttgttttt aatagagata gggtcttgct | 4020 |
| ttgtcaccca ggctatagtg caattttgct atcctagctc aatgcagcct cgaactcctg | 4080 |
| ggctcatgcg attctcctgc ctcagtctct ctacaattct ctgtccatag ccagctatgt | 4140 |
| caggaagccc acttgaaaac aaagcctggg tcttctgccc attttataa tctccagaac | 4200 |
| ctcacgaatt gccttgcata tagtaggttg gtcaagaaat gcttgttaag gatggtgttg | 4260 |
| accttcttca tcctgggacc accctgcaca cacgcgtgca cacacactct gtgcttaccc | 4320 |
| tgctttatgt caccgcgtgt ggctcatcac tccctgactg gtactgcatg ctgtgtgttt | 4380 |
| gcttttattg gtctcttcta ctgggttgca atcccagggg gcagggctt tgtcttgttt | 4440 |
| accactgtac ctccagtgcc aagaacaggg cctggtgcat agttggtgct caatatgtat | 4500 |
| ttgttgaagg agtgaatctc ctcagttctc gcttctgttc ctaaagttga ctgactcagt | 4560 |

-continued

```
ccctgtccct ccatggtgat tcacacctgt cacatgtctt ctcagcctgt gcaaagacag      4620
gggcagccgg ggacaagaag ctgtgggtgg cagagaagg aactggaggg gaccaagatt       4680
gcttggtcac ccacagcaag ctcaggagga atgcacttgc atcaggaggg ttccccgaga      4740
gatgaggatc agacaggcag gctggcaccc atgccaaggt gggtccagcc ctggagctca      4800
ctctgaaggg gccacctgcg gacaggctcc cagtggggaa aagattgttg ttcttggtgt      4860
caggagtctg gaagaacaga tttctgaagg cagaggctta atgagtttcc ttttttctgg      4920
gtcgacagac tgtgagcacg ccaggatgaa ggtaaccacg ccatgcatga gctcaggtaa      4980
cagctggccc gggagagctt tatttggatg catacacatg cacatgtgcg tgccctcct      5040 cactcccagc ctgcgtgtgt gaccttggca ggcagcctgt gggaccccaa catcaccgtg      5100
gagaccctgg aggcccacca gctgcgtgtg agcttcaccc tgtggaacga atctacccat      5160
taccagatcc tgctgaccag ttttccgcac atggagaacc acagttgctt tgagcacatg      5220
caccacatac ctgcggtaac tctgctcttt ttgacccctc tagcatagct caggaccacc      5280
cctccaagcc ctgagtctct tctctgctgg tctgacagaa ccgcgttgct agaagctcgc      5340
gactcagggc tgtgcttagt ccatagtgat catggcgcct tgccctttt cttccccagt      5400 gatcttatgc ttgatagaaa ggcagttgac tgtgtcctgc ccatgactca gtccttttg      5460 ttctttcctc ccccacacgc ccccttgttc tcttttgtt ttgctttgtt tattacaaaa       5520
aggatttgag gatttaaaaa aagaagaaa tgtgaaaata gagacaaagg ggaactaaag       5580
ataaggaaat aaggccaggt gcagtggctc ccacctgtaa tcccaatact ttgggaggcc      5640
aaggcaggag aatggcttga agttggagtt cgagactaca gtaagccatg atggcaccac      5700
tgcacccact ctggggggaca gagcgagacc ctgtctctaa aaagaaaat aaaaattgaa      5760 aaataaataa agtacattaa tgacataaaa tatgccaggc acagtggttc acgcctataa      5820
tcccagcagt ttgggaggcc aaggcaggtg gatcacttga ggtcaggagt tcgagaccag      5880
cctgaccaac atgatgaaac ccatctctca ctaaaagtac aaaaattagc caggtgtgct      5940
ggcacacgcc tgtaatccca gcaatttggg aaactgaggc agaagaatca cttgaacctg      6000
ggaggcagag gttgtagtga gctgagattg tgccactgca ctccagcctg ggtgacaaga      6060
gtgatactcc atctctaaaa aaaagaaat aaggtaata cgatgaagcc agctcagtgc        6120
aggaaacgtg tgctgtgtgg ttctgtacaa ctggtgtcca tgaacacaga tttgttgccc     6180
caattcccag cagccaaagc aaagagagac ttaccagtta ctacacgtac ttaaggattt     6240
acaataaacc agcttccatg cagaaacgga gttttttttct ggaatagaaa cctgaaaagc   6300
atttctcccc tggccttcct aagggggtgct ctggacagcc tctccatggc agtgccacag     6360
cgtgttctta cccaactagc cttacccatc ccaactagcc ttacccatcc tcgcctctct     6420
cctcagccca gaccagaaga gttccaccag cgatccaacg tcacactcac tctacgcaac     6480
cttaaagggt gctgtcgcca ccaagtgcag gtgggtgagt gtggtgtgga caggtgcagg     6540
gagcaaaaca ggtggcaatt atagagtgga caggagtgag gagtgtgcac aggtgaagag    6600
tggtgtggac gggagtgggg agtgtgcaca ggtggagaga gtggtgtgga cgggagtggg     6660
gagcgtgcac aggtggagag tgtgtgtgt ctggagtgg ggagtgtgca caggtggaga       6720
gtggtgtgga cgggagtggg gagcgtgcac aggtggagag agtggtgtgg acgggagtgg     6780
ggaacgtgca caggtggaga gagtggtgtg gctgggagtg gggagcgtgc acaggtggag     6840
agagtggtgt ggctgagagt ggggagcgtg cacaggtgga gagtgtggtg tggctgggag    6900
tggggagcgt gcacaggtgg agagagtggt gtggctggga gtggggagcg tgcacaggtg    6960
```

```
gagagtgtgg tgtggctggg agtggggagc gtgcacaggt ggggagagtg gtgtggctgg    7020
gagtggggag cgtgcacagg tggagaggtg tggctgggag tggggagcgt gcacaggtgg    7080
agagagtggt gtggctggga gtggggagcg tgcacaggtg gagagagtgg tgtggctggg    7140
agtggggagc gtgcacaggt ggagagtgtg gtgtggctgg gagtggggag cgtgcacagg    7200
tggagagtgt ggtgtggctg gagtggggag cgtgcacagg tggagagagt ggtgtggctg    7260
ggagtgggga gcgtgcacag gtggagagag tggtgtggct gggagtgggg agcgtgcaca    7320
ggtggagagt gtggtgtgga cgggagtggg gagcgtgcac agtctggcat tcttgctggt    7380
ggacagggga aagcttgtcc tctctgtggc accaagcacc actaccagtc aggattcctt    7440
gcctggtaag gcactgcccc tgcctttctc ctgtctggtt ctcccaccct cacctgggca    7500
ggggttcgct gacccgccct tgctggaggg agatgatggt cacctggaga tcgtggtgta    7560
gccagccagg atccctcct ctcacattgc cgctgctggc tggaaggcat gggcgctcta     7620
cagttctgga gcccttttcc tgccctctct gcccgcagat ccagcccttc ttcagcagct    7680
gcctcaatga ctgcctcaga cactccgcga ctgtttcctg cccagaaatg ccagacactc    7740
caggtagggg acatgcggct gtcctaggcc atactgggag aacaagtggc tgaaggcccc    7800
cagcctgtgc tgcgtcctta cctggttctg aggggtgatt agggaggaga gtttagttta    7860
acttggagtc cttcaggcct gaagtgtgga gtggggcttt agagtgtcac tccctggggc    7920
tggactcctg gctgtctttc attagctatg tagccttagg caaattactt aatcttttg     7980 attctcaact tccttgactg gaaaatgagg tggttttat cctagagccc tagttctgtg     8040
ccatgcactg agcgcagtgc tccaacatgc cgtccatttt ttcatcctca ctcattgtga    8100
gtcacggtac tatgcagtag aggatccccc caccccaaac cccaggttcc tggataagga    8160
aactgaggca cagagatgtt gaataacttg tccaagatca cacagcaggg acgctgtttt    8220
caaaagtcgc atgccctaat gcacgggagg ctgcagccac gtgctcacca aaggcaagg    8280 cgcaggcatg gagccaggct ggaaggagaa cccagcctcc caaggaggag gcaaggtgtc   8340
tcttcttaga ccagcaactc aagtgtctct tgtagatggt ttcattaagt tcaacctgga    8400
tctagagtgc ctggtgcagg gccaacatca ttaaagccct caagggacgt cagttgtgtt    8460
tcttgtgatg actgggaagg gttaagaatg ctatttcc ttttcctct gttctcattg       8520 cagaaccaat tccgggtaag cttggatctc tctccgacag cactgcagcc ctcagggac    8580 attccccagt ggccacttga gaagtccctg cctcagccag gcagacaagg ctgaaccgag    8640
gccagcccgg ggtggggggt gagaccatgg tttgtcgtgg tggggccaga gaggacagag    8700
cctggggctg gggagcaggg ctgggggcct cagggtgggc agggcaggcc ccgccgcatc    8760
actcacgctg ttctgctcac cgcagactac atgcccctgt gggtgtactg gttcatcacg    8820
ggcatctcca tcctgctggt gggctccgtc atcctgctca tcgtc                   8865
```

<210> SEQ ID NO 36
<211> LENGTH: 50
<212> TYPE: DNA
<213> ORGANISM: Artificial Sequence
<220> FEATURE:
<223> OTHER INFORMATION: Junction sequence

<400> SEQUENCE: 36
cttcctttct tcccacaggg gctgaactgc acggtcaaga atagtaagtc                    50

```
<210> SEQ ID NO 37
<211> LENGTH: 60
<212> TYPE: DNA
<213> ORGANISM: Artificial Sequence
<220> FEATURE:
<223> OTHER INFORMATION: Junction sequence

<400> SEQUENCE: 37
tggtgggctc cgtcatcctg ctcatcgtct gtatgacctg gaggctttct ggtaaggact    60

<210> SEQ ID NO 38
<211> LENGTH: 3964
<212> TYPE: DNA
<213> ORGANISM: Artificial Sequence
<220> FEATURE:
<223> OTHER INFORMATION: Humanized IL17RA

<400> SEQUENCE: 38
gggggagccg gaagcgggac agaggaggcc gtgtgaagcc gacgagcgcc agtcctcggc    60
cgggaaagcc atcgcgggcc ctcgctgtcg cgcggagcca gctgcgagcg ctccgcgacc   120
gggccgaggg ctatggcgat cggcgctgc tggccacggg tcgtccccgg gcccgcgctg   180
ggatggctgc ttctgctgct gaacgttctg gccccgggcc gcgcctcccc gcgcctcctc   240
gacttcccgg ctccggtctg cgcgcaggag gggctgaact gcacggtcaa gaatagtacc   300
tgcctggatg acagctggat tcaccctcga aacctgaccc cctcctcccc aaaggacctg   360
cagatccagc tgcactttgc ccacacccaa caaggagacc tgttcccgt ggctcacatc   420 gaatggacac tgcagacaga cgccagcatc ctgtacctcg agggtgcaga gttatctgtc   480
ctgcagctga acaccaatga acgtttgtgc gtcaggtttg agtttctgtc caaactgagg   540
catcaccaca ggcggtggcg ttttaccttc agccactttg tggttgaccc tgaccaggaa   600
tatgaggtga ccgttcacca cctgcccaag cccatccctg atgggaccc aaaccaccag   660 tccaagaatt tccttgtgcc tgactgtgag cacgccagga tgaaggtaac cacgccatgc   720
atgagctcag gcagcctgtg ggaccccaac atcaccgtgg agaccctgga ggcccaccag   780
ctgcgtgtga gcttcaccct gtggaacgaa tctacccatt accagatcct gctgaccagt   840
tttccgcaca tggagaacca cagttgcttt gagcacatgc accacatacc tgcgcccaga   900
ccagaagagt tccaccagcg atccaacgtc acactcactc tacgcaacct taagggtgc    960 tgtcgccacc aagtgcagat ccagccctt ttcagcagct gcctcaatga ctgcctcaga   1020
cactccgcga ctgtttcctg cccagaaatg ccagacactc cagaaccaat tccggactac   1080
atgcccctgt gggtgtactg gttcatcacg ggcatctcca tcctgctggt gggctccgtc   1140
atcctgctca tcgtctgtat gacctggagg ctttctggcg ccgatcaaga gaaacatggt   1200
gatgactcca aaatcaatgg catcttgccc gtagcagacc tgactccccc accctgagg   1260 cccaggaagg tctggatcgt ctactcggcc gaccacccc tctatgtgga ggtggtccta   1320
aagttcgccc agttcctgat cactgcctgt ggcactgaag tagcccttga cctcctggaa   1380
gagcaggtta tctctgaggt gggggtcatg acctgggtga gccgacagaa gcaggagatg   1440
gtggagagca actccaaaat catcatcctg tgttcccgag gcacccaagc aaagtggaaa   1500
gctatcttgg gttgggctga gctgctgtc cagctacggt gtgaccactg gaagcctgct   1560 ggggacctt tcactgcagc catgaacatg atcctgccag acttcaagag gccagcctgc   1620
ttcggcacct acgttgtttg ctacttcagt ggcatctgta gtgagaggga tgtccccgac   1680
ctcttcaaca tcacctccag gtacccactc atggacagat ttgaggaggt ttacttccgg   1740
```

```
atccaggacc tggagatgtt tgaacccggc cggatgcacc atgtcagaga gctcacaggg    1800
gacaattacc tgcagagccc tagtggccgg cagctcaagg aggctgtgct taggttccag    1860
gagtggcaaa cccagtgccc cgactggttc gagcgtgaga acctctgctt agctgatggc    1920
caagatcttc cctccctgga tgaagaagtg tttgaagacc cactgctgcc accaggggga    1980
ggaattgtca aacagcagcc cctggtgcgg gaactcccat ctgacggctg ccttgtggta    2040
gatgtctgtg tcagtgagga agaaagtaga atggcaaagc tggaccctca gctatggcca    2100
cagagagagc tagtggctca cacctccaa agcatggtgc tgccagcaga gcaggtccct    2160
gcagctcatg tggtggagcc tctccatctc ccagacggca gtggagcagc tgcccagctg    2220
cccatgacag aggacagcga ggcttgcccg ctgctggggg tccagaggaa cagcatcctt    2280
tgcctccccg tggactcaga tgacttgcca ctctgtagca ccccaatgat gtcacctgac    2340
cacctccaag gcgatgcaag agagcagcta gaaagcctaa tgctctcggt gctgcagcag    2400
agcctgagtg gacagcccct ggagagctgg ccgaggccag aggtggtcct cgagggctgc    2460
acaccctctg aggaggagca gcggcagtcg gtgcagtcgg accagggcta catctccagg    2520
agctccccgc agcccccga gtggctcacg gaggaggaag agctagaact gggtgagccc    2580
gttgagtctc tctctcctga ggaactacgg agcctgagga agctccagag gcagctttc    2640 ttctgggagc tcgagaagaa ccctggctgg aacagcttgg agccacggag acccaccca    2700 gaagagcaga atccctccta ggcctcctga gcctgctact taagagggtg tatattgtac    2760
tctgtgtgtg cgtgcgtgtg tgtgtgtgtg tgtgtgtgtg tgtgcgtgtg tgtgtgtgtg    2820
tgtgtgtgtg tgtgtgtgta gtgcccggct tagaaatgtg aacatctgaa tctgacatag    2880
tgttgtatac ctgaagtccc agcacttggg aactgagact tgatgatctc ctgaagccag    2940
gtgttcaggg ccagtgtgaa aacatagcaa gacctcagag aaatcaatgc agacatcttg    3000
gtactgatcc ctaaacacac ccctttccct gataacccga catgagcatc tggtcatcat    3060
tgcacaagaa tccacagccc gttcccagag ctcatagcca agtgtgttgc tcattccttg    3120
aatatttatt ctgtacctac tattcatcag acatttggaa ttcaaaaaca agttacatga    3180
cacagcctta gccactaaga agcttaaaat tcggtaagga tgtaaaatta gccaggatga    3240
atagagggct gctgccctgg ctgcagaaga acccgagaga gcctgcgggt ggcgtctggg    3300
caagagggga gtggcctgtg gattgagtat taggaaggag ccagagctca gggtggagag    3360
agctctgtgg ggctagggtg ggagcagctg gggactcctc tcatgagtgg atctgttgcc    3420
ctacggggga ggaaacttca tgccaaatat acccagaagt cttctcagat cagttctta    3480 gaaagagctg gtatagaaat gggtgatgta aaacttgaga agcaggaaga ggcgtgtgaa    3540
atcctgtgct ctctcaagtg ctggctgcca gtccgtggga gggctgcggc atgtgattct    3600
tcatgggctg cagccaccag atccctggag agctctacct cggggtacag tgagggagtt    3660
gagaaagatg tgagggtagt gggcatgggg gcgtggcata acaggagaac tcgggaggcc    3720
ctcaaggtca gaggaaagta tgtcactgta taactacagt aagagaggtt gtttaaagta    3780
gctccagggc gccctcatgg ggcagacagc agccttgtgg cgtaggttct agagaatgca    3840
caggtcttcc tagacttagg tgagaaaagg accatgaaat gctgtgggaa gcacgaattc    3900
agtgattgtg tgtgtgcata tgtgtgtgca gtaatgaaga cttaataaag ttgctgtatt    3960
ggta                                                                3964
```

-continued

<210> SEQ ID NO 39
<211> LENGTH: 862
<212> TYPE: PRT
<213> ORGANISM: Artificial Sequence
<220> FEATURE:
<223> OTHER INFORMATION: Humanized IL17RA

<400> SEQUENCE: 39

```
Met Ala Ile Arg Arg Cys Trp Pro Arg Val Val Pro Gly Pro Ala Leu
1               5                   10                  15

Gly Trp Leu Leu Leu Leu Leu Asn Val Leu Ala Pro Gly Arg Ala Ser
            20                  25                  30

Pro Arg Leu Leu Asp Phe Pro Ala Pro Val Cys Ala Gln Glu Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65              70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145             150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225             230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305             310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ser Gly Ala Asp Gln
            340                 345                 350

Glu Lys His Gly Asp Asp Ser Lys Ile Asn Gly Ile Leu Pro Val Ala
        355                 360                 365
```

```
Asp Leu Thr Pro Pro Leu Arg Pro Arg Lys Val Trp Ile Val Tyr
370                 375                 380

Ser Ala Asp His Pro Leu Tyr Val Glu Val Val Leu Lys Phe Ala Gln
385                 390                 395                 400

Phe Leu Ile Thr Ala Cys Gly Thr Glu Val Ala Leu Asp Leu Leu Glu
            405                 410                 415

Glu Gln Val Ile Ser Glu Val Gly Val Met Thr Trp Val Ser Arg Gln
            420                 425                 430

Lys Gln Glu Met Val Glu Ser Asn Ser Lys Ile Ile Ile Leu Cys Ser
        435                 440                 445

Arg Gly Thr Gln Ala Lys Trp Lys Ala Ile Leu Gly Trp Ala Glu Pro
450                 455                 460

Ala Val Gln Leu Arg Cys Asp His Trp Lys Pro Ala Gly Asp Leu Phe
465                 470                 475                 480

Thr Ala Ala Met Asn Met Ile Leu Pro Asp Phe Lys Arg Pro Ala Cys
                485                 490                 495

Phe Gly Thr Tyr Val Val Cys Tyr Phe Ser Gly Ile Cys Ser Glu Arg
            500                 505                 510

Asp Val Pro Asp Leu Phe Asn Ile Thr Ser Arg Tyr Pro Leu Met Asp
            515                 520                 525

Arg Phe Glu Glu Val Tyr Phe Arg Ile Gln Asp Leu Glu Met Phe Glu
530                 535                 540

Pro Gly Arg Met His His Val Arg Glu Leu Thr Gly Asp Asn Tyr Leu
545                 550                 555                 560

Gln Ser Pro Ser Gly Arg Gln Leu Lys Glu Ala Val Leu Arg Phe Gln
                565                 570                 575

Glu Trp Gln Thr Gln Cys Pro Asp Trp Phe Glu Arg Glu Asn Leu Cys
            580                 585                 590

Leu Ala Asp Gly Gln Asp Leu Pro Ser Leu Asp Glu Glu Val Phe Glu
            595                 600                 605

Asp Pro Leu Leu Pro Pro Gly Gly Ile Val Lys Gln Gln Pro Leu
            610                 615                 620

Val Arg Glu Leu Pro Ser Asp Gly Cys Leu Val Val Asp Val Cys Val
625                 630                 635                 640

Ser Glu Glu Glu Ser Arg Met Ala Lys Leu Asp Pro Gln Leu Trp Pro
                645                 650                 655

Gln Arg Glu Leu Val Ala His Thr Leu Gln Ser Met Val Leu Pro Ala
            660                 665                 670

Glu Gln Val Pro Ala Ala His Val Val Glu Pro Leu His Leu Pro Asp
            675                 680                 685

Gly Ser Gly Ala Ala Ala Gln Leu Pro Met Thr Glu Asp Ser Glu Ala
            690                 695                 700

Cys Pro Leu Leu Gly Val Gln Arg Asn Ser Ile Leu Cys Leu Pro Val
705                 710                 715                 720

Asp Ser Asp Asp Leu Pro Leu Cys Ser Thr Pro Met Met Ser Pro Asp
                725                 730                 735

His Leu Gln Gly Asp Ala Arg Glu Gln Leu Glu Ser Leu Met Leu Ser
            740                 745                 750

Val Leu Gln Gln Ser Leu Ser Gly Gln Pro Leu Glu Ser Trp Pro Arg
            755                 760                 765

Pro Glu Val Val Leu Glu Gly Cys Thr Pro Ser Glu Glu Glu Gln Arg
770                 775                 780
```

```
Gln Ser Val Gln Ser Asp Gln Gly Tyr Ile Ser Arg Ser Ser Pro Gln
785                 790                 795                 800

Pro Pro Glu Trp Leu Thr Glu Glu Glu Leu Glu Leu Gly Glu Pro
            805                 810                 815

Val Glu Ser Leu Ser Pro Glu Glu Leu Arg Ser Leu Arg Lys Leu Gln
        820                 825                 830

Arg Gln Leu Phe Phe Trp Glu Leu Glu Lys Asn Pro Gly Trp Asn Ser
        835                 840                 845

Leu Glu Pro Arg Arg Pro Thr Pro Glu Glu Gln Asn Pro Ser
    850                 855                 860

<210> SEQ ID NO 40
<211> LENGTH: 80
<212> TYPE: DNA
<213> ORGANISM: Artificial Sequence
<220> FEATURE:
<223> OTHER INFORMATION: Junction sequence

<400> SEQUENCE: 40
aggagcagac cctgaactca caagggaaga ccctcactcg atatcgaatt ccgaagttcc    60
tattctctag aaagtatagg                                               80

<210> SEQ ID NO 41
<211> LENGTH: 80
<212> TYPE: DNA
<213> ORGANISM: Artificial Sequence
<220> FEATURE:
<223> OTHER INFORMATION: Junction sequence

<400> SEQUENCE: 41
gtataggaac ttcatcagtc aggtacataa tggtggatcc caattgtcca ccagctttgt    60
agtcacagga gacctaatct                                               80

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
gctcgactag agcttgcgga                                               20

<210> SEQ ID NO 43
<211> LENGTH: 25
<212> TYPE: DNA
<213> ORGANISM: Artificial Sequence
<220> FEATURE:
<223> OTHER INFORMATION: Synthetic primer

<400> SEQUENCE: 43
tcttaagtag caggctcagg aggcc                                         25

<210> SEQ ID NO 44
<211> LENGTH: 23
<212> TYPE: DNA
<213> ORGANISM: Artificial Sequence
<220> FEATURE:
<223> OTHER INFORMATION: Synthetic primer

<400> SEQUENCE: 44
gttcaccagc gtgaatgctc aca                                           23
```

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
ctgtcagaag ttggcagcag g                                    21

<210> SEQ ID NO 46
<211> LENGTH: 25
<212> TYPE: DNA
<213> ORGANISM: Artificial Sequence
<220> FEATURE:
<223> OTHER INFORMATION: Synthetic primer

<400> SEQUENCE: 46
ggactggatg agacagctca aaggg                                25

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
gctgcttaca gggcttcttc ctcaa                                25

<210> SEQ ID NO 48
<211> LENGTH: 25
<212> TYPE: DNA
<213> ORGANISM: Artificial Sequence
<220> FEATURE:
<223> OTHER INFORMATION: Synthetic primer

<400> SEQUENCE: 48
gagacgcaat gggcagttag attcc                                25

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
aaatgttcca gcacttcctg ggtgt                                25

<210> SEQ ID NO 50
<211> LENGTH: 22
<212> TYPE: DNA
<213> ORGANISM: Artificial Sequence
<220> FEATURE:
<223> OTHER INFORMATION: Synthetic primer

<400> SEQUENCE: 50
accactcacc tcctctgctg ga                                   22

<210> SEQ ID NO 51
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 51
cctcatggag cacagatgcc tat                                              23

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
ctgtcagaag ttggcagcag g                                                21

<210> SEQ ID NO 53
<211> LENGTH: 25
<212> TYPE: DNA
<213> ORGANISM: Artificial Sequence
<220> FEATURE:
<223> OTHER INFORMATION: Synthetic primer

<400> SEQUENCE: 53
caaacagcag cctacacaac ttcat                                            25

<210> SEQ ID NO 54
<211> LENGTH: 24
<212> TYPE: DNA
<213> ORGANISM: Artificial Sequence
<220> FEATURE:
<223> OTHER INFORMATION: Synthetic primer

<400> SEQUENCE: 54
ctaggcaaca caccttctcc ctgt                                             24

<210> SEQ ID NO 55
<211> LENGTH: 1653
<212> TYPE: DNA
<213> ORGANISM: Mus musculus

<400> SEQUENCE: 55
agcagaagct ccctcagcga ggacagcaag ggactagcca ggagggagaa cagaaactcc       60
agaacatctt ggaaatagct cccagaaaag caagcagcca accaggcagg ttctgtccct      120
ttcactcact ggcccaaggc gccacatctc cctccagaaa agacaccatg agcacagaaa      180
gcatgatccg cgacgtggaa ctggcagaag aggcactccc ccaaaagatg ggggcttcc       240 agaactccag gcggtgccta tgtctcagcc tcttctcatt cctgcttgtg cagggggcca      300
ccacgctctt ctgtctactg aacttcgggg tgatcggtcc ccaaagggat gagaagttcc      360
caaatggcct ccctctcatc agttctatgg cccagaccct cacactcaga tcatcttctc      420
aaaattcgag tgacaagcct gtagcccacg tcgtagcaaa ccaccaagtg gaggagcagc      480
tggagtggct gagccagcgc gccaacgccc tcctggccaa cggcatggat ctcaaagaca      540
accaactagt ggtgccagcc gatgggttgt accttgtcta ctcccaggtt ctcttcaagg      600
gacaaggctg ccccgactac gtgctcctca cccacaccgt cagccgattt gctatctcat      660
accaggagaa agtcaacctc ctctctgccg tcaagagccc ctgccccaag gacacccctg      720
agggggctga gctcaaaccc tggtatgagc ccatatacct gggaggagtc ttccagctgg      780 agaagggga ccaactcagc gctgaggtca atctgcccaa gtacttagac tttgcggagt      840
ccgggcaggt ctactttgga gtcattgctc tgtgaaggga tgggtgttc atccattctc      900 tacccagccc ccactctgac cccttactc tgaccccttt attgtctact cctcagagcc      960
```

```
cccagtctgt atccttctaa cttagaaagg ggattatggc tcagggtcca actctgtgct   1020
cagagctttc aacaactact cagaaacaca agatgctggg acagtgacct ggactgtggg   1080
cctctcatgc accaccatca aggactcaaa tgggctttcc gaattcactg gagcctcgaa   1140
tgtccattcc tgagttctgc aaagggagag tggtcaggtt gcctctgtct cagaatgagg   1200
ctggataaga tctcaggcct tcctaccttc agacctttcc agattcttcc ctgaggtgca   1260
atgcacagcc ttcctcacag agccagcccc cctctatta tatttgcact tattatttat   1320
tatttattta ttatttattt atttgcttat gaatgtattt atttggaagg ccggggtgtc   1380
ctggaggacc cagtgtggga agctgtcttc agacagacat gttttctgtg aaaacggagc   1440
tgagctgtcc ccacctggcc tctctacctt gttgcctcct cttttgctta tgtttaaaac   1500
aaaatattta tctaacccaa ttgtcttaat aacgctgatt tggtgaccag gctgtcgcta   1560
catcactgaa cctctgctcc ccacgggagc cgtgactgta atcgccctac gggtcattga   1620
gagaaataaa gatcgcttgg aaaagaaatg tga                                1653
```

<210> SEQ ID NO 56
<211> LENGTH: 235
<212> TYPE: PRT
<213> ORGANISM: Mus musculus

<400> SEQUENCE: 56

```
Met Ser Thr Glu Ser Met Ile Arg Asp Val Glu Leu Ala Glu Ala
1               5                   10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
        50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
                100                 105                 110

Asn Ala Leu Leu Ala Asn Gly Met Asp Leu Lys Asp Asn Gln Leu Val
            115                 120                 125

Val Pro Ala Asp Gly Leu Tyr Leu Val Tyr Ser Gln Val Leu Phe Lys
        130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235
```

<210> SEQ ID NO 57
<211> LENGTH: 1686
<212> TYPE: DNA
<213> ORGANISM: Homo sapiens

<400> SEQUENCE: 57

```
cagacgctcc ctcagcaagg acagcagagg accagctaag agggagagaa gcaactacag      60
accccccctg aaaacaaccc tcagacgcca catcccctga caagctgcca ggcaggttct     120
cttcctctca catactgacc cacgctccca ccctctctcc cctggaaagg acaccatgag     180
cactgaaagc atgatccggg acgtggagct ggccgaggag gcgctcccca gaagacagg      240
ggggccccag ggctccaggc ggtgcttgtt cctcagcctc ttctccttcc tgatcgtggc     300
aggcgccacc acgctcttct gctgctgca ctttggagtg atcggccccc agagggaaga     360
gttcccagg gacctctctc taatcagccc tctggcccag gcagtcagat catcttctcg     420
aaccccgagt gacaagcctg tagcccatgt tgtagcaaac cctcaagctg aggggcagct     480
ccagtggctg aaccgccggg ccaatgccct cctggccaat ggcgtggagc tgagagataa     540
ccagctggtg gtgccatcag agggcctgta cctcatctac tcccaggtcc tcttcaaggg     600
ccaaggctgc ccctccaccc atgtgctcct cacccacacc atcagccgca tcgccgtctc     660
ctaccagacc aaggtcaacc tcctctctgc catcaagagc cctgccaga gggagacccc     720
agaggggct gaggccaagc cctggtatga gcccatctat ctgggagggg tcttccagct     780
ggagaaggt gaccgactca cgctgagat caatcggccc gactatctcg actttgccga     840
gtctgggcag gtctactttg ggatcattgc cctgtgagga ggacgaacat ccaaccttcc     900
caaacgcctc ccctgccca atccctttat tacccctcc ttcagacacc ctcaacctct     960
tctggctcaa aaagagaatt gggggcttag ggtcggaacc caagcttaga actttaagca    1020
acaagaccac cacttcgaaa cctgggattc aggaatgtgt ggcctgcaca gtgaagtgct    1080
ggcaaccact aagaattcaa actggggcct ccagaactca ctggggccta cagctttgat    1140
ccctgacatc tggaatctgg agaccaggga gcctttggtt ctggccagaa tgctgcagga    1200
cttgagaaga cctcacctag aaattgacac aagtggacct taggccttcc tctctccaga    1260
tgtttccaga cttccttgag acacggagcc cagccctccc catggagcca gctccctcta    1320
tttatgtttg cacttgtgat tatttattat ttatttatta tttatttatt tacagatgaa    1380
tgtatttatt tgggagaccg gggtatcctg ggggacccaa tgtaggagct gccttggctc    1440
agacatgttt tccgtgaaaa cggagctgaa caataggctg ttcccatgta gccccctggc    1500
ctctgtgcct tcttttgatt atgttttta aaatatttat ctgattaagt tgtctaaaca    1560
atgctgattt ggtgaccaac tgtcactcat tgctgagcct ctgctcccca ggggagttgt    1620
gtctgtaatc gccctactat tcagtggcga gaaataaagt ttgcttagaa aagaaaaaaa    1680
aaaaaa                                                              1686
```

<210> SEQ ID NO 58
<211> LENGTH: 233
<212> TYPE: PRT
<213> ORGANISM: Homo sapiens

<400> SEQUENCE: 58

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30
```

```
Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 59
<211> LENGTH: 6173
<212> TYPE: DNA
<213> ORGANISM: Mus musculus

<400> SEQUENCE: 59
agcctgctta gcctgctcag gctgtgggtc ccatggccag ttctgccaaa ggccaaaaga      60
actatggcat gatatagacg agaaattaca ggacttcgtt gtttgtttgt tttgacaaag     120
tgttccgtgt aatccctgta gctaaatagg accttgaaca cctcctgatc tttctgactt     180
tatttcccca atgttagggt tatagcatgc atccacacct agtttacctg gtgccaggga     240
tagaactcaa gactttctgc atgctaggca ggcatgtgcc aattgaactg catcctctag     300
ccctgaaaga ggtgtttatg cgtttccttc ctccattaca tctgggcagc caccaatgct     360
gtaggttctg ccttgaagca ctttctcctt cccattctcc ccaggatgca ggctcttgtc     420
atgggctctt tctgggtcat tgtaaaatgc tcttcactgg tctccatggt gacctcagaa     480
ccttcctctg attcttcatc ttgcttaaag actccatttt ataacattaa cgtgtaagtg     540
ggtctttctt ttatgtaaac tttgttggtg gctctctatc tttattagta tgagatttaa     600
atcctgcagg tgagttcgag gccagcctag tccacaaaga gagttctagg acagacagag     660
ctgttacaca aagaaatcct gtcttaaaaa gaaagcaaac aacaacaaca aaccctgcg      720 gggtgtgttc tctgcttacc acagtctttc ttctgcttat tctatatgta cccagatgca     780
cacctcagac caggagggct ctctctcagg cagacagtac atattgttct tccctacctc     840
tcttcctttc ttccttcctt cctttctttc tttcttctt tctttctctc ttttttttt      900 tttttgttgt tgttttggt tttggttttt tgagacaggg tttctctgta tagctctggc     960
```

-continued

```
tgtcctggaa ctcactctgt agaccagctg cctcgaact cagaaatccg cctgcctctg    1020
cctcccaagt gctgggatta aaggcatgcg ccaccaatgt ccagctctct acatttctta    1080
tctccactat aaatgccccc aggttccacg gatttcctga ggactgcctt gccaaggtca    1140
tgaaactcga tcacactcca ctaaacttga gatccccaaa gtcaaggatt tatctcttgg    1200
agctgtctcc ctgattcctt gttccaggtg cacaagtgtt tgtgggatgc agaggaagag    1260
actggatgag aactaccgag ttcacagctc acatccctga aggatggggc ctgagtagct    1320
ggacacttca gaatgagtga cagcctaaga cgtgagaaga agcacttctg tgccttttcca   1380 gccttcggtc ctacccacat cttcccccaa ggcaagccat cgaaactgga attcctcttt    1440
tccaaccagg gtcctggaga ctagaatcct cctttttttc catgacctaa tagtattgcc    1500
cttcccccac ctttggtgta agaacttctc ctaacaaaaa tttctagtcc taagtcagag    1560
gcctcatcct gtagggtcct gccccatccc aaggaggagg aaggactgcc aatcagagcg    1620
tcatgagagc tgagcagaca ggacctgctt ctcttccctc tcaattgttt gggcctgaga    1680
acagcagtgt gcccagtggc cagcctgact gccaccatca ccagctgcag cctgctacaa    1740
tagtctgact gatgccatgt ggcaacagcg gtgacatctg aggtggccag ctgttgtcat    1800
ctatctccat cttaaaaaaa aaaacgagca aaaaataaat aataaatcat cttcaaaaac    1860 tttgctttt gagagctgta acttacaagc tgagagaaaa ctggttccga acaggagttt    1920
cctactcagt gtttctcaga cagaaactag accaacctaa cagccatcag gagtatcctt    1980
gtgactttgg ctatccactt aagacagtct agagtcacct gaaaaggagt ctcagctgag    2040
ggattgccca ggctgtatgt gtttgggagg cggggagggg gggtgttaat tgatgtagga    2100
ggcccaagac caccatgagt ggcaccgtcc tctgcacagg ggatcctggg ttgtataaga    2160
aagcttgata gatggatgac attcggtgca cacaccatta atcccagcac ttggaaggtt    2220
gaagtaggtg atttctgtga gttcaaggcc atcctgatgc acatattgag ttccagggca    2280
gctagggcta catagtgaga gcctgtctct atgtatatgt atgtatacat gtatatgtat    2340
atatgtgtgt ataagtaata tataaaatat aataataaaa taactttaaa gagtaaattt    2400
tgaaaaaaaa tcaaacactt tgataataat aataataaga agaaaagag ccaggcaatg     2460 gtggtgtatg cctttaatcc cagcacttgg gaggcagagg caggcggatt tctgagtttc    2520
aaggccagcc tggtctaaaa agtgagttcc aggacaacca gggctacaca gagaaaccct    2580
gtcttgaaaa acaaaagaa agagagggg gggggaagga aggaaggaag gaaggaagga      2640
aggaaggaag gaaggaaaga aagaagaaa gaaagaaaga aagaaagaaa gaaagaaaga     2700
aagaaagaga aggaagttgg gccagcaaga tggctcagtg ggcaaaggtg cttactggct    2760
ttacctaatg gcctgagttc agttcccaga acccatacag cagcttacaa ctgtctataa    2820
ctcctgttcc aggagagctg acatcctcat acaggcatac aagcaggcaa acaccaatt     2880 tacatgaaat aaaaatgaat tatatattaa gaaaaaaag agctgtactc tgacctccac     2940
atgtggcctg tggcacttgt atgtactcac ataaatagat atgttttttaa atgttctgct   3000 gtgtgtatag gattttttgcc tgcatgtatg tctcagcacc atttgagtat agtgcctgca   3060
aaggccagaa gaggatgtca catccccaca aactgcaagg acagatgtaa taagccaaca    3120
tgcagatgct gggaattaac actggtcctc tggaagaaca tctagtgctc agaaccctaa    3180
gccatttctc caatcctcaa aacaatattt taaaattttg tcttaagaca gaaatcatca    3240
atgtgactgc tgggaatgtg gggatggact caggggctca cacatgcctg caagcagcta    3300
cctgagctgt gtcccaggcc ttccaataga gaagcactgc tcagatgtcc tttgttgggc    3360
```

```
agtggtagca cacaccttta atcccagcac ttgggaggca gaggcagacg gatttctgag    3420
tttggggcca gcctggtcta caaagtgagt tccaggacag ccagggctat acagagaaac    3480
cctgtctcga aaacaaaca aacaaacaaa caaaaaactg ccttcacctg tgtagaattc    3540
tgaagctccc tctgtacaga gcattggaag cctggggtgt acatttgggg ttacatgatc    3600
ttggggttct aagagaatac ccccaaatca tcttccagac ctggaacatt ctaggacagg    3660
gttctcaacc ttcctaactc catgacccct taatacagtt cctcatgttg tggtgacccc    3720
aaccatacaa ttattttcgt tgctatttca taactgtaat ttcgctgcta ttatgaatca    3780
taatgtaaat atttgtttta aatagaggtt tgccaaaggg accttgccca caggttgaga    3840
actgccgctc cagagagtaa ggggacacag ttaagattgt tacacaccag gatgccccag    3900
atttggggag agggcactgt aatgaacttc cttgacatga aactggcaga tgaaactggc    3960
agaaaaaaaa aaaaaagctg gcagtggtg gcacacacct ttaatcccag cacttgggag    4020
gcagaggcag gcggatttct gagttctagg ccagcctggt ctacagagtg agtttcagga    4080
cagccagggc tacacagaga aaccctgtct cgaaaaaagc aaaaaaaaaa aaaaaaaaa    4140
aaaaaaactg gcagatgacc agaaaataca gatatattgg aataactgtg acttgaaccc    4200
ccaaagacaa gagaggaaat aggcctgaag gggcggcagg catgtcaagc atccagagcc    4260
ctgggttcga acctgaaaaa acaaaggtgc cgctaaccac atgtggcttc ggagccctcc    4320
agacatgacc atgatcgaca gagagggaaa tgtgcagaga agcctgtgag cagtcaaggg    4380
tgcagaagtg atataaacca tcactcttca gggaaccagg cttccagtca cagcccagct    4440
gcaccctctc cacgaattgc tcggccgttc actggaactc ctgggcctga cccagctccc    4500
tgctagtccc tgcggcccac agttccccgg acccgactcc cttcccaga acgcagtagt    4560
ctaagccctt agcctgcggt tctctcctag gccccagcct ttcctgcctt cgactgaaac    4620
agcagcatct tctaagccct gggggcttcc ccaagcccca gccccgacct agaacccgcc    4680
cgctgcctgc cacactgccg cttcctctat aaagggaccc gagcgccagc gcccaggacc    4740
ccgcacagca ggtgagcctc tcctacctg tctccttggg cttaccctgg tatcaggcat    4800
ccctcaggat cctacctcct ttcttgagcc acagccttt ctatacaacc tgcctggatc    4860
cccagcctta atgggtctgg tcctcctgtc gtggctttga ttttttggtct gttcctgtgg    4920
cggccttatc agtctctctc tctctctctc tctctctctc tctctctctc tctctctctc    4980
tctctctctc tccctctctc tctctctctc tctctctctt tctctctctc tgcctctgtt    5040
agccattgtc tgattctatg gtggagcttt cctcttcccc tctgtctctc cttatccctg    5100
ctcacttcag ggttcccctg cctgtcccct tttctgtctg tcgccctgtc tctcagggtg    5160
gctgtctcag ctgggaggta aggtctgtct tccgctgtgt gccccgcctc cgctacacac    5220
acacactctc tctctctctc tcagcaggtt ctccacatga cactgctcgg ccgtctccac    5280
ctcttgaggg tgcttggcac ccctcctgtc ttcctcctgg ggctgctgct ggccctgcct    5340
ctaggggccc aggtgaggca gcaagagatt gggggtgctg gggtggccta gctaactcag    5400
agtcctagag tcctctccac tctcttctgt cccagggact ctctggtgtc cgcttctccg    5460
ctgccaggac agcccatcca ctccctcaga agcacttgac ccatggcatc ctgaaacctg    5520
ctgctcacct tgttggtaaa cttctgcctc cagaggagag gtccagtccc tgccttttgt    5580
cctacttgcc caggggctca ggcgatcttc ccatctcccc acaccaactt ttcttacccc    5640
taagggcagg caccccactc ccatctccct accaaccatc ccacttgtcc agtgcctgct    5700
ccctcaggga tggggacctc tgatcttgat agccccccaa tgtcttgtgc ctcttcccag    5760
```

| | |
|---|---|
| ggtaccccag caagcagaac tcactgctct ggagagcaag cacggatcgt gcctttctcc | 5820 |
| gacatggctt ctctttgagc aacaactccc tcctgatccc caccagtggc ctctactttg | 5880 |
| tctactccca ggtggttttc tctggagaaa gctgctcccc cagggccatt cccactccca | 5940 |
| tctacctggc acacgaggtc cagctctttt cctcccaata cccttccat gtgcctctcc | 6000 |
| tcagtgcgca gaagtctgtg tatccgggac ttcaaggacc gtgggtgcgc tcaatgtacc | 6060 |
| aggggctgt gttcctgctc agtaagggag accagctgtc cacccacacc gacggcatct | 6120 |
| cccatctaca cttcagcccc agcagtgtat tctttggagc ctttgcactg tag | 6173 |

<210> SEQ ID NO 60
<211> LENGTH: 4033
<212> TYPE: DNA
<213> ORGANISM: Mus musculus

<400> SEQUENCE: 60

| | |
|---|---|
| catcggcttc ctcctggaac tcctcctcct cggacacaat ccctccccc accccacccc | 60 |
| tgccattttc agctcctttg ctttcttcat tagtctgccc cttaacgtgc ctgcgactga | 120 |
| cctgctgccc cttaaagaag ggctgtcaga acccgtggtg gtccatgcct ttagccccag | 180 |
| ccctggagag ttccaggtga cccaggacta tatgtgagac ccggactata gatagataga | 240 |
| tagatagata gatagataga tagatagata gatagataga tagatagata gatagataga | 300 |
| gcatacatcc atccatacat acattacata catactacat acatataacc tatcaggccc | 360 |
| aactgaactg atgggcccaa cccacggagc tttgttccac agtctttgta gtttttctct | 420 |
| ctgggaacga atcctgccta ccttctcctg ttggctcctc ctcacagagg cagaagccag | 480 |
| gagcaagggt gtatgtgagg gggtcttgtg gggaccaggt cttgctact tgtggattc | 540 |
| tttctcccac cctttctcgc cctggtttca ccccctaaca ctagatagga tagaaataag | 600 |
| gattaggaaa atccgtgagt ctaatatctt ccttcgtt tcttctttga ccgacccgca | 660 |
| gctgctaaca aacctcaacc aacctcccta acctttcagc atcctggcaa tcagggtgct | 720 |
| ggcagaagtc tcagggttta attgtccctt cttccgccct cttggagccc tggccttaga | 780 |
| gccaggacgt gggtgcaaca ggtgtccaca gttcaaagct gggtcagcca cctgcacg | 840 |
| tgtcccagaa tcaaaaacca cgtctgcatt tccgtgaaga cactggcaag ggccggcata | 900 |
| gtttacattc tttattttca aaattcgtgt cctacattcc gttctccccc ccccccgcca | 960 |
| cgcccccggc cgctcgggac tgtcggggtc ccggacatca cgattcacac attcgcaccg | 1020 |
| tcagtcgatc ctccaggaat gaatacagat ggctgtcacc ccaccatcac cgccccgaag | 1080 |
| aaggtcttcc ctctcctgta gtccaccatg tcggggtgac tgatgttaac gtagaccctc | 1140 |
| tcgccgctcc ggagctgcgc caggccgccg aaccccacgc tcgtgtacca taacgacccg | 1200 |
| tacccgatgg ggtccacaac aggtgtgact gtctccgcgc cctccagcag caactcgggg | 1260 |
| gaacctcgcc cgtaggcgcc cccgcgcgg tacagggcgc tgcgcagcgt gagcgagcga | 1320 |
| gcacggcttc ggccggcagg gggcgtcctg cccctgtacc cgacgtggca gtagaggtaa | 1380 |
| tagacgccgt cctgtggcag cgccagcccg tgggtggggg agaactgcgc gccgctcctc | 1440 |
| agaaacgctt cttcttggct cgcctcccag ctgagccctt gcccactcat ccaagcgcct | 1500 |
| gcagaaaggg acacgcgtga cgcgctcggc cgtgatctct aggtcggaga cccgggcagg | 1560 |
| atgagcaggg acctggagcg gaggagcggg gtcttcctcc ttctgtggta cttagcgggg | 1620 |
| aggggcagga ataacggtgc tatctatcac ccgaagggac taaagtggcg agatccctgc | 1680 |
| cggttttttac ctgtttcctg agcagtcagt cataccgagg gagaagttgg tggtggagga | 1740 |

```
gttgggaaag taccagtagt gtcatagcag agccaaagga ctctcgctta ctgtgggggt    1800
acatagccag cactcttcgg tctaccagat gcttacctat gaggtgggca gcagggagct    1860
cagggttgag gtcagtttct ggttccccct ttggcagctg ttgaacccct ggatctggtg    1920
tagaatccgc agctggagac aggatggtca tccatgcaga tgcctcccga gaggactgcg    1980
caacagggcc ctgggatgtg gaggctagat tcctggaagc attggatctc tgaggatgca    2040 gacggggtc aggagtctct gagaggctag agggtgaggg caagatgcac gacggtttgc     2100
tgtcatccag tcttttctga gcctgtgctc ctgagccaat gatcttctca acctggatgg    2160
gtaggtaggg ttagagtgcc cagaggtcag atttggctaa tggcaactcc accctccca    2220 ccgtagagcc cagccccaag gcctgggcct gctgtgtcct ccctagactg catcttgcta    2280
gaagaacaaa caaagacgat gtatgcaggc agagagacgc aagtgcagtg ttatctggaa    2340
aagaagccaa ccaggaaggg gcttgaaaat tcaggctagg attgcctgga gaggcaaaga    2400
cagaccagac attccctctg gggagagcgg ccagctgagc gcggtgggca gaagcacagc    2460
cataagtaaa taaacagtca caagaggcag ccctctggag cccgttgcag ccactcaccc    2520
gacgtccctg atcctgcggc accaaggcca gcacagccag gacagtgata ggcactgcca    2580
acaacagggt caccagggaa gtagctcctg ccacagccag caagaggcag cccctccct    2640 ggggtctccc acccaggccc tgcagtcccc gtgtccccat ccagactcag aactaggacc    2700
ggggcagggg ctttcatacc tcaggggtag acccccccac cccgcagac ccacacacct     2760 gccccctgcc cggggacttt ccgaacaccc ttcctcccct cacccagctt cctgtttacc    2820
cagcgctggg gccggggttg ggtggctgga tgcctgggtt ctctgaactg ggaaggaga    2880 tggggtagag agaggttttc aaggtaaaga tgaagagggg cttggcaggg agggaagatg    2940
aagcccaggg aaggaaggga gcttgcagaa ggccaggcaa caaacaaggt tgtcatggcc    3000
aggtaggact ccaagtatct cgtgtgttct tcatgcttct ggaccttaca gtgctgaagg    3060
gagggctgca aagacacacg cacctgcaca catgcatgca cgcacgcacg cgcgcgcgca    3120
cacacacaca cacacacaca cacacacaca cacgggaggg ggggtgagga gatggagtgg    3180
gaggccaaca agggtcggct gtgtgtctgc gtccctgata cgaccctctc cccacactgg    3240
ctgacttctt cctgtttcag tctctaaaac cagatgggaa aggcagaatt aagtgggtcc    3300
gcagtggtta tggcttatg aagggggctc agcctctctc tctctctctc tctctctctc    3360
tctctgtcct gataaagcaa tacagaggca cactccacct taagggagtc tgtctagaat    3420
gagcctcctc cattgggaag catcaactac ttataaatga gggacagggc aaatgaatgt    3480
atgaatgaat gaatgaatga atgagaaatt tgttgacttc aatgaacatc aggaaccgaa    3540
ttaatggcac ccgaggggca gctgattgga gtttagggaa gagcaggtcg gaggaaggtg    3600
gacagaggtt tcaggccatg tccccttcct ggtgaccttg cagtctctat gtcccagacc    3660
agacaactcg tttggaaaat attaccaaca ccaatattag tagaatacag ctgactgacc    3720
aaaggcacca agaatgtgct agccactgaa ctacagtctt tattacacta gccacttcgt    3780
ctccatggga aagccctaag aagatgctga ggcccagaga gacgaaaagg cagtgttggg    3840
atagcagtag agtttcctga cagggcactt ggctagtagg tttgattctg taacaggcaa    3900
aacagaacta attccagctt catacatttt actagatgta aattttgtct tcctgaggca    3960
aggaaaaaaa aagaggaaac aaagactaac ttgaacaatt cagcggtaac atgaggtaat    4020
agtcacaacc tgg                                                     4033
```

```
<210> SEQ ID NO 61
<211> LENGTH: 6287
<212> TYPE: DNA
<213> ORGANISM: Homo sapiens

<400> SEQUENCE: 61
aacttggaaa atccagaaa gaaaaaataa ttgatttcaa gaccttctcc ccattctgcc      60
tccattctga ccatttcagg ggtcgtcacc acctctcctt tggccattcc aacagctcaa     120
gtcttccctg atcaagtcac cggagctttc aaagaaggaa ttctaggcat cccaggggac     180
cacacctccc tgaaccatcc ctgatgtctg tctggctgag gatttcaagc ctgcctagga     240
attcccagcc caaagctgtt ggtctgtccc accagctagg tggggcctag atccacacac     300
agaggaagag caggcacatg gaggagcttg ggggatgact agaggcaggg aggggactat     360
ttatgaaggc aaaaaaatta aattatttat ttatggagga tggagagagg ggaataatag     420
aagaacatcc aaggagaaac agagacaggc ccaagagatg aagagtgaga gggcatgcgc     480
acaaggctga ccaagagaga aagaagtagg catgagggat cacagggccc cagaaggcag     540
ggaaaggctc tgaaagccag ctgccgacca gagccccaca cggaggcatc tgcaccctcg     600
atgaagccca ataaacctct tttctctgaa atgctgtctg cttgtgtgtg tgtgtctggg     660
agtgagaact tcccagtcta tctaaggaat ggagggaggg acagagggct caaagggagc     720
aagagctgtg gggagaacaa aaggataagg gctcagagag cttcagggat atgtgatgga     780
ctcaccaggt gaggccgcca gactgctgca ggggaagcaa aggagaagct gagaagatga     840
aggaaaagtc agggtctgga ggggcggggg tcagggagct cctgggagat atggccacat     900
gtagcggctc tgaggaatgg gttacaggag acctctgggg agatgtgacc acagcaatgg     960
gtaggagaat gtccagggct atggaagtcg agtatgggga ccccccctta acgaagacag    1020
ggccatgtag agggccccag ggagtgaaag agcctccagg acctccaggt atggaataca    1080
ggggacgttt aagaagatat ggccacacac tggggccctg agaagtgaga gcttcatgaa    1140
aaaaatcagg gaccccagag ttccttggaa gccaagactg aaaccagcat tatgagtctc    1200
cgggtcagaa tgaaagaaga aggcctgccc cagtggggtc tgtgaattcc cgggggtgat    1260
ttcactcccc gggctgtcc caggcttgtc cctgctaccc ccacccagcc tttcctgagg     1320
cctcaagcct gccaccaagc cccagctcc ttctccccgc agggacccaa acacaggcct     1380
caggactcaa cacagctttt ccctccaacc ccgttttctc tccctcaagg actcagcttt    1440
ctgaagcccc tcccagttct agttctatct ttttcctgca tcctgtctgg aagttagaag    1500
gaaacagacc acagacctgg tccccaaaag aaatggaggc aataggtttt gaggggcatg    1560
gggacggggt tcagcctcca gggtcctaca cacaaatcag tcagtggccc agaagacccc    1620
cctcggaatc ggagcaggga ggatggggag tgtgaggggt atccttgatg cttgtgtgtc    1680
cccaactttc caaatcccg cccccgcgat ggagaagaaa ccgagacaga aggtgcaggg     1740
cccactaccg cttcctccag atgagctcat gggtttctcc accaaggaag ttttccgctg    1800
gttgaatgat tctttccccg ccctcctctc gccccaggga catataaagg cagttgttgg    1860
cacacccagc cagcagacgc tccctcagca aggacagcag aggaccagct aagagggaga    1920
gaagcaacta cagacccccc ctgaaaacaa ccctcagacg ccacatcccc tgacaagctg    1980
ccaggcaggt tctcttcctc tcacatactg acccacggct ccaccctctc tccctggaa     2040 aggacaccat gagcactgaa agcatgatcc gggacgtgga gctggccgag gaggcgctcc    2100
ccaagaagac agggggggccc cagggctcca ggcggtgctt gttcctcagc ctcttctcct    2160
```

```
tcctgatcgt ggcaggcgcc accacgctct tctgcctgct gcactttgga gtgatcggcc      2220
cccagaggga agaggtgagt gcctggccag ccttcatcca ctctcccacc caagggaaa       2280 tggagacgca agagagggag agagatggga tgggtgaaag atgtgcgctg atagggaggg      2340
atggagagaa aaaacgtgg agaagacgg ggatgcagaa agagatgtgg caagagatgg        2400
ggaagagaga gagagaaaga tggagagaca ggatgtctgg cacatggaag gtgctcacta     2460
agtgtgtatg gagtgaatga atgaatgaat gaatgaacaa gcagatatat aaataagata     2520
tggagacaga tgtgggtgt gagaagagag atggggaag aaacaagtga tatgaataaa        2580
gatggtgaga cagaaagagc gggaaatatg acagctaagg agagatggg gggagataag      2640 gagagaagaa gatagggtgt ctggcacaca gaagacactc agggaaagag ctgttgaatg     2700
cctggaaggt gaatacacag atgaatggag agagaaaacc agacacctca gggctaagag    2760
cgcaggccag acaggcagcc agctgttcct cctttaaggg tgactccctc gatgttaacc    2820
attctccttc tccccaacag ttccccaggg acctctctct aatcagccct ctggcccagg    2880
cagtcagtaa gtgtctccaa acctctttcc taattctggg tttgggtttg ggggtagggt   2940
tagtaccggt atggaagcag tggggaaat ttaaagtttt ggtcttgggg gaggatggat    3000
ggaggtgaaa gtagggggt attttctagg aagtttaagg gtctcagctt tttcttttct     3060
ctctcctctt caggatcatc ttctcgaacc ccgagtgaca agcctgtagc ccatgttgta     3120
ggtaagagct ctgaggatgt gtcttggaac ttggagggct aggatttggg gattgaagcc    3180
cggctgatgg taggcagaac ttggagacaa tgtgagaagg actcgctgag ctcaagggaa    3240
gggtggagga acagcacagg ccttagtggg atactcagaa cgtcatggcc aggtgggatg    3300
tgggatgaca gacagagagg acaggaaccg gatgtggggt gggcagagct cgagggccag    3360
gatgtggaga gtgaaccgac atggccacac tgactctcct ctccctctct ccctccctcc    3420
agcaaaccct caagctgagg ggcagctcca gtggctgaac cgccgggcca atgccctcct    3480
ggccaatggc gtggagctga gagataacca gctggtggtg ccatcagagg gcctgtacct    3540
catctactcc caggtcctct tcaagggcca aggctgcccc tccacccatg tgctcctcac    3600
ccacaccatc agccgcatcg ccgtctccta ccagaccaag gtcaacctcc tctctgccat    3660
caagagcccc tgccagaggg agacccccaga gggggctgag gccaagccct ggtatgagcc   3720
catctatctg ggaggggtct tccagctgga aagggtgac cgactcagcg ctgagatcaa     3780
tcggcccgac tatctcgact tgccgagtc tgggcaggtc tactttggga tcattgccct     3840
gtgaggagga cgaacatcca accttcccaa acgcctcccc tgccccaatc cctttattac   3900 ccctccttc agacaccctc aacctcttct ggctcaaaaa gagaattggg ggcttagggt     3960
cggaacccaa gcttagaact ttaagcaaca agaccaccac ttcgaaacct gggattcagg    4020
aatgtgtggc ctgcacagtg aagtgctggc aaccactaag aattcaaact ggggcctcca    4080
gaactcactg gggcctacag cttttgatccc tgacatctgg aatctggaga ccagggagcc    4140
tttggttctg gccagaatgc tgcaggactt gagaagacct cacctagaaa ttgacacaag    4200
tggaccttag gccttcctct ctccagatgt ttccagactt ccttgagaca cggagcccag    4260
ccctccccat ggagccagct ccctctattt atgtttgcac ttgtgattat ttattattta    4320
tttattattt atttatttac agatgaatgt atttatttgg gagaccgggg tatcctgggg    4380
gacccaatgt aggagctgcc ttggctcaga catgttttcc gtgaaaacgg agctgaacaa    4440
taggctgttc ccatgtagcc ccctggcctc tgtgccttct tttgattatg ttttttaaaa    4500
tatttatctg attaagttgt ctaaacaatg ctgatttggt gaccaactgt cactcattgc    4560
```

```
tgagcctctg ctccccaggg gagttgtgtc tgtaatcgcc ctactattca gtggcgagaa    4620
ataaagtttg cttagaaaag aaacatggtc tccttcttgg aattaattct gcatctgcct    4680
cttcttgtgg gtgggaagaa gctccctaag tcctctctcc acaggcttta agatccctcg    4740
gacccagtcc catccttaga ctcctagggc cctggagacc ctacataaac aaagcccaac    4800
agaatattcc ccatccccca ggaaacaaga gcctgaacct aattacctct ccctcagggc    4860
atgggaattt ccaactctgg gaattccaat ccttgctggg aaaatcctgc agctcaggtg    4920
agatttccgg ctgttgcagc tggccagcag tccgagaga gctggagagg agccgcattc     4980
tcaggtacct gaatcacaca gccaagggac ttccagagat tcgggtgtct aggcttcaaa    5040
tcaccctgtc ctaactctgc aacctgaacc agccacttaa cctatctatc caatggggat    5100
aggaatgtcc accacacata gggcatgtga gagaaggcct gacctccatc agaggacctc    5160
actcagccct tggcacagtg ggcacttagt gaattctggc ttccttcaac cagttttccag   5220 ctgttctatc cccttccatt ctctcagtgg gtgaaatcga agagactgag gacaataaag    5280
aacaaggaac cgaactgccg gacgtggtgg catgcacctg taatcctacc actttgcaag    5340
gccaaggtga gaggatcgct tgaacccagg agttccagag caacctgggc aacatagtga    5400
gatcctgtct ctattttta aaaagaatg aaacatagga ataagatgtg ggtgaaggac      5460
tcacatgccg gcttggtccc actggtcttt gtggtgaagg aggggagagg tgagaggtgg    5520
gtaatccgga aagagaaaag cacccctcc ctggatgaag gctcttctgg agagagtcaa     5580
agacaaataa gggtggggcg cagtggctca tgcctgttat cccaacactt tgggaggctg    5640
aggtgggagg accacttgag cccactagtt caagaccagc ctgtgcaaca tagcaagacc    5700
ttgtttctag aaaaaaaatt aaagattagt caggtgtagt ggtgcatgcc tgtaatccta    5760
gctcctcagg aggctgaggc aggaggatca ctcaagccca ggagtttgag gttacagtaa    5820
gctatgatca tgccactgta cccccgtctg ggtgacagaa cgagaccctg tctcaaaaaa    5880
ataataattc aaaaacaaa tatggagacg gaaattgagc cccctagac tgggagcccc       5940 cactgagttc ggaaattagg ctttacctcc agccctgggg tgccaggcag gagaaaacca    6000
tgtggtaggc tgaggggta gggtgaccca ttggggtgac ctagataggg ccttgggtca     6060
ccctctgcct cctccagcct gtggctgaaa gtcagccatg aagtaatggg ggacactgtt    6120
actcatccca gaagcaccca cacttactca cttttgggaa gggggaccta aagtgtgaaa    6180
aaaaggtgag gattttccgt ctcaccctaa atgggacacc ctaagtgggg catcggtttt    6240
tcctcctccc cagaacttcc tggtgttttc aggcaccaca ggctcct                  6287
```

<210> SEQ ID NO 62
<211> LENGTH: 79
<212> TYPE: DNA
<213> ORGANISM: Artificial Sequence
<220> FEATURE:
<223> OTHER INFORMATION: Junction sequence

<400> SEQUENCE: 62

```
aatgtatgct atacgaagtt attaggtccc tcgagggat ccgaattcat cggcttcctc      60
ctggaactcc tcctcctcg                                                   79
```

<210> SEQ ID NO 63
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 63
ggtgacctag atagtgcctg g                                              21

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
tcagtcgcag gcacgttaag                                                20

<210> SEQ ID NO 65
<211> LENGTH: 22
<212> TYPE: DNA
<213> ORGANISM: Artificial Sequence
<220> FEATURE:
<223> OTHER INFORMATION: Synthetic primer

<400> SEQUENCE: 65
tgcatcgcat tgtctgagta gg                                             22

<210> SEQ ID NO 66
<211> LENGTH: 1162
<212> TYPE: DNA
<213> ORGANISM: Artificial Sequence
<220> FEATURE:
<223> OTHER INFORMATION: Humanized IL17A

<400> SEQUENCE: 66
atccacctca cacgaggcac aagtgcaccc agcaccagct gatcaggacg cgcaaacatg     60
actcctggga agacctcatt ggtgtcactg ctactgctgc tgagcctgga ggccatagtg    120
aaggcaggaa tcacaatccc acgaaatcca ggatgcccaa attctgagga caagaacttc    180
ccccggactg tgatggtcaa cctgaacatc ataaccgga ataccaatac caatcccaaa    240
aggtcctcag attactacaa ccgatccacc tcaccttgga atctccaccg caatgaggac    300
cctgagagat atccctctgt gatctgggag gcaaagtgcc gccacttggg ctgcatcaac    360
gctgatggga acgtggacta ccacatgaac tctgtcccca tccagcaaga gatcctggtc    420
ctgcgcaggg agcctccaca ctgccccaac tccttccggc tggagaagat actggtgtcc    480
gtgggctgca cctgtgtcac cccgattgtc accatgtgg cctaaacaga acccgcggc    540 tgaccctaa gaaaccccca cgtttctcag caaacttact tgcatttta aaacagttcg    600 tgctattgat tttcagcaag gaatgtggat tcagaggcag attcagaatt gtctgccctc    660
cacaatgaaa agaaggtgta aagggtccc aaactgcttc gtgtttgttt ttctgtggac    720
tttaaattat ttgtgtattt acaatatccc aagatagctt tgaagcgtaa cttattttaa    780
tgaagtatct acattattat tatgtttctt tctgaagaag acaaaattca agactcagaa    840
attttattat ttaaaaggta aagcctatat ttatatgagc tatttatgaa tctatttatt    900
tttcttcagt atttgaagta ttaagaacat gattttcaga tctacctagg gaagtcctaa    960
gtaagattaa atattaatgg aaatttcagc tttactattg tttattaa ggttctctcc    1020 tctgaatggg gtgaaaacca aacttagttt tatgtttaat aacttttaa attattgaag    1080 attcaaaaaa ttggataatt tagctcccta ctctgtttta aaaaaaaatt gtaacaatat    1140
cactgtaata ataaagttttt gg                                          1162
```

HUMANIZED TRANSGENIC ANIMAL

CLAIM OF PRIORITY

This application in a continuation of International Application No. PCT/CN2020/072714, filed on Jan. 17, 2020, which claims the priorities of Chinese Patent Application No. CN 201910044180.6 filed on Jan. 17, 2019 and entitled "GENETICALLY MODIFIED NON-HUMAN ANIMAL" and Chinese Patent Application No. CN 201910616231.8 filed on Jul. 9, 2019 and entitled "GENETICALLY MODIFIED NON-HUMAN ANIMAL", which are incorporated herein by reference in their entirety.

TECHNICAL FIELD

The disclosure relates to the field of genetic engineering, and specifically to a genetically-modified non-human animal, especially a rodent, such as a genetically-modified mouse. Specifically, the disclosure relates to a genetically-modified mouse containing a human interleukin 17A (IL-17A) gene, a human 17RA (IL-17RA) gene and/or a human TNF-alpha gene, and a method for producing the same, and a use thereof.

BACKGROUND

Interleukin (IL) 17 (IL17 or IL-17) family is a class of characteristic cytokine, which is mainly secreted by activated T cells. Six members of the IL-17 family have been discovered, namely IL-17A, IL-17B, IL-17C, IL-17D, IL-17E (also known as IL-25) and IL-17F. IL-17 receptors (IL17R or IL-17R) have also been grouped into a unique family, which included 5 homologous member subunits presently, namely IL-17RA, IL-17RB, IL-17RC, IL-17RD and IL-17RE. IL-17 binds to the receptor to activate the downstream signaling pathways (including MAP kinase pathway, NF-kB pathway, mRNA stabilization signaling pathway, ERK signaling pathway and JAK/STAT signaling pathway), and then stimulates a variety of cells to produce inflammatory mediators. It has become a key participant in immune and inflammatory diseases, and may lead to organ-specific or systemic autoimmune diseases.

A large number of studies have shown that a variety of autoimmune diseases (such as multiple sclerosis, asthma, inflammatory bowel disease, psoriasis, and rheumatoid arthritis) have high levels of IL-17 expression. In addition, IL-17 is also closely related to the occurrence and development of a variety of autoimmune diseases, including Crohn's disease, Behcet's disease, systemic lupus erythematosus, primary Sjogren's syndrome, multiple sclerosis, myocarditis, type I diabetes, thyroiditis, atopic dermatitis, hypersensitivity, rheumatoid arthritis, graft versus host disease and psoriasis. In addition, IL-17 is also expressed in a variety of tumor tissues. IL-17 is capable of cooperating with TNF-α, LTα, IFNγ and IL-1β to enhance inflammation. Deficiency of IL-17 and IL-17R leads to the reduction of allergen-specific immune response and autoimmune inflammation. Blocking the biological activity of IL-17 in vivo by specific antibodies has shown significant clinical effects. At present, the US FDA has approved three human IL-17/IL-17R-related antibodies, including IL-17A monoclonal antibody Secukinumab, Ixekizumab and IL-17RA monoclonal antibody Brodalumab, which are mainly used for moderate to severe plaque psoriasis. However, these agents have obvious side effects, such as infections, diarrhea, etc., and Brodalumab is found associated with patients' suicidal tendency. Many drugs targeting this signaling pathway are or have entered clinical research. Considering that most of the existing drugs for the treatment of autoimmune diseases can only ameliorate the symptoms of the diseases and are far from fully meeting the clinical needs, more drugs targeting IL-17/IL-17R still need to be developed. Experimental animal disease models are indispensable research tools for studying the etiology and pathogenesis of human diseases, developing prevention and treatment technologies and drugs. Because the amino acid sequences of human IL-17 and IL-17 receptor family are significantly different from the corresponding protein in rodents, for example, the identity of human IL-17A and mouse IL-17A protein sequence is only 60%, so antibodies that recognize human IL-17A protein usually cannot recognize mouse IL-17A, that is, regular mice cannot be used to screen and evaluate the effectiveness of drugs targeting the IL-17/IL-17R signaling pathway. In view of the wide participation of IL-17/IL-17R in the process of diseases and the great application value of targeting this signaling pathway, in order to make preclinical trials more effective and minimize R&D failures, there is an urgent need in the field to develop non-human animal models expressing humanized proteins associated with IL-17/IL-17R signaling pathway.

SUMMARY

Unless otherwise specified, the practice of this disclosure will adopt the traditional techniques of cell biology, cell culture, molecular biology, genetically-modified biology, recombinant DNA and immunology. These techniques are descripted in detail in the following documents. For example: Molecular Cloning A Laboratory Manual, $2^{nd}$ Ed., ed. By Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986).
IL-17A/IR-17RA Cytokine interleukin 17 (IL17 or IL-17) family is a class of characteristic cytokine, which is mainly secreted by activated T cells. Six members of the IL-17 family have been discovered, namely IL-17A, IL-17B, IL-17C, IL-17D, IL-17E (also known as IL-25) and IL-17F. Members of the IL-17 family have low sequence similarity with any other known cytokines, and the sequence similarity among the members of the family is also relatively low. For example, IL-17F has the highest homology with IL-17A (55%), and is usually co-expressed with IL-17A; the sequences of IL-17B, IL-17D and IL-17C overlap with that of IL-17A by 29% to 23%; and IL-17E seems to be the most different member of the family, with only 16% sequence homology (Gaffen S L, Nat. Rev. Immunol. 2009 August; 9(8):556-67). IL-17 receptors (IL-17R or IL17R) have also been grouped into a unique family, including 5 homologous subunits presently, namely IL-17RA, IL-17RB, IL-17RC, IL-17RD and IL-17RE, in which IL-17RB, -RC, -RD, -RE have homology with the earliest discovered IL-17RA. IL-17 binds to the receptor to activate the downstream signaling pathways (including MAP kinase pathway, NF-kB pathway, mRNA stabilization signaling pathway, ERK signaling pathway and JAK/STAT signaling pathway), and stimulates a variety of cells to produce inflammatory mediators. It has become a key participant in immune and inflammatory diseases, and may lead to organ-specific or systemic autoimmune diseases.

IL17 receptors are type I transmembrane proteins. Among them, IL-17RA is ubiquitously expressed; IL-17RB dominant expresses on the surface of a type of NKT cells that mediate airway allergic reactions; IL-17RC only expresses in stromal cells and non-hematopoietic cells, but not in thymus and leukocytes; IL-17RD mainly expresses in endothelial cells, epithelial cells and smooth muscle cells; the cells expressing IL-17RE are not yet clear, and some studies have shown that the colon cells and kidney cells of mice might express IL-17RE. The IL-17 family members all contain cysteine knot formed by 4 cysteines and 2 serines. Except for IL-17B, the IL-17 family members all form dimer. IL-17A and IL-17F can exist as homodimer or form heterodimer with each other, which binds to the receptor heterodimer formed by IL-17RA and IL-17RC to initiate the downstream signal transduction pathway. The dimer of IL-17A or IL-17F first binds to one of the receptors, IL17-RA and IL17-RC, and after binding, the unbound monomer in the dimer exhibits a decreased affinity for the previously bound receptor, causing the remaining monomer to only bind to another type of receptor. In mice, this is a little difference. Although murine IL-17RA can bind murine IL-17A and IL17-F, murine IL-17RC can only bind IL-17F. At present, it is not fully understood which ligand each IL-17R binds to (see Table 1), but studies have suggested that the ubiquitously expressed IL-17RA may be a signal transduction subunit shared by all IL-17 family members. According to different activated cells, IL-17RA signal can induce the synthesis of a variety of molecules, such as cytokines, chemokines, antimicrobial peptides, mucins, etc. IL-17RA-deficient mice are resistant to a variety of inflammatory diseases, such as rheumatoid arthritis, multiple sclerosis (MS), and asthma, but are also prone to infections by multiple pathogens, such as *Toxoplasma gondii* and *Candida albicans*. In addition, both human IL-17A and human IL-17F can cause the production of chemokine ligand (CXCL) 1 in murine cells, suggesting that there is no species specificity. However, hIL-17AR alone cannot initiate signaling pathways in IL-17RA−/− mouse fibroblasts, suggesting that hIL-17AR and hIL-17RC are species-specific.

TABLE 1

IL17/IL-17R family

| Receptor (complex) | Ligand |
|---|---|
| IL-17RA/RC | IL-17A, IL-17F, IL-17A/F, vIL-17* |
| IL-17RA/RB | IL-17E (IL-25) |
| IL-17RD (SEF) | Unknown |
| IL-17RA/RD | Unknown |
| IL-17RE | IL-17C |
| Unknown | IL-17D |

*indicates virus IL-17, see Gaffen SL. Current opinion in immunology. 2011;23(5):613-619.

Because the amino acid sequence of human IL-17 family and IL-17 receptor family are significantly different from the corresponding proteins in rodents, for example, the identity of human IL-17A and mouse IL-17A protein sequences is only 60%, antibodies that recognize human IL-17A protein usually cannot recognize mouse IL-17A, that is, regular mice cannot used to screen and evaluate the effectiveness of drugs targeting the IL-17/IL-17R signaling pathway.

Genetically-Modified Non-Human Animal

The disclosure solves the above technical problems by constructing a genetically-modified non-human animal, such as a genetically-modified mouse containing a sequence of human IL-17A gene and/or IL-17RA gene in the genome.

Accordingly, in one aspect, the disclosure relates to a genetically-modified non-human animal containing a sequence of the human IL-17A gene in an expressible form in the genome.

As used herein, a gene in an "expressible form" means that the gene is expressed in animal or animal cells under the control of a promoter that can function in the animal or animal cells. The promoter is not particularly limited as long as it functions in the animal or animal cells into which the gene has been introduced. The promoter may be a promoter derived from the animal or animal cell, or a heterologous promoter. The promoter may also be a natural promoter of the gene to be introduced or a promoter of another gene.

In some embodiments, the sequence of the corresponding endogenous sequence in the genome of the animal is replaced with the human IL-17A gene. In some embodiments, at least 1, at least 2, or all 3 of exons 1-3 of the human IL-17A gene, in a whole or partially, are used to replace the corresponding endogenous sequences in the genome of the animal.

The term "corresponding" as used herein refers to a method used to determine the corresponding nucleotide/amino acid sequence corresponding to a certain nucleotide/amino acid sequence. For example, for the purpose of the disclosure, when referring to a certain nucleotide/amino acid sequence, those skilled in the art can compare another nucleotide/amino acid sequence with the reference sequence, so as to determine which sequence in the another nucleotide/amino acid sequence is the nucleotide/amino acid sequence corresponding to the reference nucleotide/amino acid sequence.

In some embodiments, the animal expresses human IL-17A protein. For example, the human IL-17A protein may comprise an amino acid sequence with at least 80% sequence identity, such as at least 85%, at least 90%, at least 95%, at least 98% or at least 99% sequence identity with SEQ ID NO: 4, or comprises or consists of SEQ ID NO: 4.

In some embodiments, the sequence of the human IL-17A gene comprises the coding sequence of the human IL-17A gene. In some embodiments, the sequence of the human IL-17A gene comprises the sequence from the start codon to the stop codon of the human IL-17A gene.

In some embodiments, the sequence of the human IL-17A gene comprises a nucleotide sequence with at least 80% sequence identity, such as at least 85%, at least 90%, at least 95%, at least 98% or at least 99% sequence identity with SEQ ID NO: 7. In a preferred embodiment, the sequence of the human IL-17A gene comprises or consists of SEQ ID NO: 7.

The correlation between two amino acid sequences or between two nucleotide sequences is described by the parameter "sequence identity".

In some embodiments of the above genetically-modified non-human animal, the animal is homozygous for the human IL-17A gene sequence or a fragment thereof. In other embodiments, the animal is heterozygous for the human IL-17A gene sequence or a fragment thereof.

Individuals of a biological population or species usually include multiple alleles at each locus. An exogenous allele is an allele introduced into an organism, while an endogenous allele is an allele naturally present in the cell, and usually the one in the wild-type unmodified organism. Heterozygous animals have two types of allele. In some cases, it is desirable to introduce an exogenous allele to produce an animal that is homozygous for the allele, and the allele is already present in the heterozygous animal.

In some embodiments, in addition to the sequence of the human IL-17A gene in an expressible form, the genome of the genetically-modified animal may also comprises a sequence of the human IL-17RA gene in an expressible form and/or a sequence of the human TNF-α gene in an expressible form. In some embodiments, the animal may be homozygous or heterozygous for the sequence of the human IL-17RA gene and/or the sequence of the human TNF-α gene.

In some embodiments, the sequence of the human IL-17RA gene is used to replace the corresponding endogenous sequence in the genome of the animal. In some embodiments, at least 1, at least 2, at least 3, at least 4, at least 5, at least 6, at least 7, at least 8, at least 9, at least 10, or all 11 of exons 1-11 of the human IL-17RA gene, in a whole or partially, are used to replace the corresponding endogenous sequences in the genome of the animal.

In some embodiments, the sequence of the human TNF-α gene is used to replace the corresponding endogenous sequence in the genome of the animal.

In some embodiments, the animal expresses human IL-17RA protein or humanized IL-17RA protein, and/or human TNF-α protein.

In some embodiments, the human IL-17RA protein comprises an amino acid sequence with at least 80% sequence identity, such as at least 85%, at least 90%, at least 95%, at least 98% or at least 99% sequence identity with SEQ ID NO: 32, or comprises or consists of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with amino acids 49-341 of SEQ ID NO: 32, or comprises or consists of amino acids 49-341 of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with SEQ ID NO: 39, or comprises or consists of SEQ ID NO: 39.

In some embodiments, the human TNF-α protein comprises an amino acid sequence with at least 80% sequence identity, such as at least 85%, at least 90%, at least 95%, at least 98% or at least 99% sequence identity with SEQ ID NO: 58, or comprises or consists of SEQ ID NO: 58.

In some embodiments, the sequence of the human IL-17RA gene comprises the coding sequence of the human IL-17RA gene. In other embodiments, the sequence of the human IL-17RA comprises the sequence from exon 2 to exon 11 of the human IL-17RA gene.

In some embodiments, the sequence of the human IL-17RA gene comprises a nucleotide sequence with at least 80% sequence identity, such as at least 85%, at least 90%, at least 95%, at least 98% or at least 99% sequence identity with SEQ ID NO: 35. In a preferred embodiment, the sequence of the human IL-17RA gene comprises or consists of SEQ ID NO: 35.

In some embodiments, the sequence of the human TNF-α gene comprises the coding sequence of the human TNF-α gene. In some embodiments, the sequence of the human TNF-α gene comprises the sequence from the start codon to the stop codon of the human TNF-α gene.

In some embodiments, the sequence of the human TNF-α gene comprises a nucleotide sequence with at least 80% sequence identity, such as at least 85%, at least 90%, at least 95%, at least 98% or at least 99% sequence identity with SEQ ID NO: 61. In a preferred embodiment, the sequence of the human TNF-α gene comprises or consists of SEQ ID NO: 61.

In another aspect, the disclosure relates to a genetically-modified non-human animal comprising a sequence of the human IL-17RA gene in an expressible form in the genome of the animal.

In some embodiments, the sequence of the human IL-17RA gene is used to replace the corresponding endogenous sequence in the genome of the animal.

In some embodiments, the animal expresses human IL-17RA protein. In other embodiments, the animal expresses humanized IL-17RA protein.

In some embodiments, the human IL-17RA protein comprises an amino acid sequence with at least 80% sequence identity, such as at least 85%, at least 90%, at least 95%, at least 98% or at least 99% sequence identity with SEQ ID NO: 32, or comprises or consists of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with amino acids 49-341 of SEQ ID NO: 32, or comprises or consists of amino acids 49-341 of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with SEQ ID NO: 39, or comprises or consists of SEQ ID NO: 39.

In some embodiments, the sequence of the human IL-17RA gene comprises the coding sequence of the human IL-17RA gene. In other embodiments, the sequence of the human IL-17RA comprises the sequence from exon 2 to exon 11 of the human IL-17RA gene.

In some embodiments, the sequence of the human IL-17RA gene comprises a nucleotide sequence with at least 80% sequence identity, such as at least 85%, at least 90%, at least 95%, at least 98% or at least 99% sequence identity with SEQ ID NO: 35. In a preferred embodiment, the sequence of the human IL-17RA gene comprises or consists of SEQ ID NO: 35.

In some embodiments, the animal is homozygous for the sequence of the human IL-17RA gene. In other embodiments, the animal is heterozygous for the sequence of the human IL-17RA gene.

In some embodiments, in addition to the sequence of the human IL-17RA gene in an expressible form, the genome of the genetically-modified animal may also comprise a sequence of the human TNF-α gene in an expressible form. The animal may be homozygous or heterozygous for the sequence of the human TNF-α gene.

In some embodiments, the sequence of the human TNF-α gene is used to replace the corresponding endogenous sequence in the genome of the animal.

In some embodiments, the human TNF-α protein comprises an amino acid sequence with at least 80% sequence identity, such as at least 85%, at least 90%, at least 95%, at least 98% or at least 99% sequence identity with SEQ ID NO: 58, or comprises or consists of SEQ ID NO: 58.

In some embodiments, the sequence of the human TNF-α gene comprises the coding sequence of the human TNF-α gene. In some embodiments, the sequence of the human TNF-α gene comprises the sequence from the start codon to the stop codon of the human TNF-α gene.

In some embodiments, the sequence of the human TNF-α gene comprises a nucleotide sequence with at least 80% sequence identity, such as at least 85%, at least 90%, at least 95%, at least 98% or at least 99% sequence identity with SEQ ID NO: 61. In a preferred embodiment, the sequence of the human TNF-α gene comprises or consists of SEQ ID NO: 61.

In any of the embodiments of the above genetically-modified non-human animal, the animal may be selected from mammals, such as non-primates, for example, livestock, pigs, cattle, sheep, goats, chickens, rabbits, fish, zebrafish, dogs, mice, cats, rats, and laboratory animals.

In some embodiments, the animal is a rodent, such as a mouse or a rat. In a preferred embodiment, the animal is a mouse.

Various strains of mice and rats are known in the art and can be used to produce genetically-modified non-human animals as described in the present application. For example, the mouse can be selected from the following strains:

C57BL strain, for example, selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/01a;

129 strain, for example, selected from 129P1, 129P2, 129P3, 129X1, 129S1 (e.g., 129I/SV, 129I/SvIm), 129S2, 129S4, 129S5, 129S9/SvEvH, 129S6 (129/SvEvTac), 129S7, 129S8, 129T1, 129T2;

BALB strain, such as BALB/c; and hybrids of the above strains, for example, 50% BALB/c-50% 129S4/Sv; or 50% C57BL/6-50% 129.

The rat may be selected from the following strains: Wistar rat, LEA rat, Sprague Dawley rat, Fischer rat, F344, F6 and Dark Agouti, and hybrids of two or more of the above strains.

In another aspect, the disclosure relates to cells obtained from the above genetically-modified non-human animals. In some embodiments, the cells may be selected from somatic cells, stem cells such as embryonic stem cells, germ cells, and fertilized eggs.

Animal Cells

In one aspect, the disclosure relates to a non-human animal cell comprising a sequence of the human IL-17A gene in an expressible form in the genome of the cell.

In some embodiments, the sequence of the human IL-17A gene is used to replace the corresponding endogenous sequence in the genome of the cell.

In some embodiments, the cell expresses human IL-17A protein. For example, the human IL-17A protein comprises an amino acid sequence with at least 80% sequence identity, such as at least 85%, at least 90%, at least 95%, at least 98% or at least 99% sequence identity with SEQ ID NO: 4, or comprises or consists of SEQ ID NO: 4.

In some embodiments, the sequence of the human IL-17A gene comprises the coding sequence of the human IL-17A gene. In some embodiments, the sequence of the human IL-17A gene comprises the sequence from the start codon to the stop codon of the human IL-17A gene.

In some embodiments, the sequence of the human IL-17A gene comprises a nucleotide sequence with at least 80% sequence identity, such as at least 85%, at least 90%, at least 95%, at least 98% or at least 99% sequence identity with SEQ ID NO: 7. In a preferred embodiment, the sequence of the human IL-17A gene comprises or consists of SEQ ID NO: 7.

In some embodiments, the cell is homozygous for the human IL-17A gene sequence or a fragment thereof. In other embodiments, the cell is heterozygous for the human IL-17A gene sequence or a fragment thereof.

In some embodiments, the genome of the cell also comprises a sequence of the human IL-17RA gene and/or a sequence of the human TNF-α gene in an expressible form.

In some embodiments, the sequence of the human IL-17RA gene and/or the sequence of the human TNF-α gene are used to replace the corresponding endogenous sequence in the genome of the cell.

In some embodiments, the cell expresses human IL-17RA protein or humanized IL-17RA protein, and/or human TNF-α protein.

In some embodiments, the human IL-17RA protein comprises an amino acid sequence with at least 80% sequence identity, such as at least 85%, at least 90%, at least 95%, at least 98% or at least 99% sequence identity with SEQ ID NO: 32, or comprises or consists of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with amino acids 49-341 of SEQ ID NO: 32, or comprises or consists of amino acids 49-341 of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with SEQ ID NO: 39, or comprises or consists of SEQ ID NO: 39.

In some embodiments, the human TNF-α protein comprises an amino acid sequence with at least 80% sequence identity, such as at least 85%, at least 90%, at least 95%, at least 98% or at least 99% sequence identity with SEQ ID NO: 58, or comprises or consists of SEQ ID NO: 58.

In some embodiments, the sequence of the human IL-17RA gene comprises the coding sequence of the human IL-17RA gene. In other embodiments, the sequence of the human IL-17RA gene comprises the sequence from exon 2 to exon 11 of the human IL-17RA gene.

In some embodiments, the sequence of the human IL-17RA gene comprises a nucleotide sequence with at least 80% sequence identity, such as at least 85%, at least 90%, at least 95%, at least 98% or at least 99% sequence identity with SEQ ID NO: 35. In a preferred embodiment, the sequence of the human IL-17RA gene comprises or consists of SEQ ID NO: 35.

In some embodiments, the sequence of the human TNF-α gene comprises the coding sequence of the human TNF-α gene. In some embodiments, the sequence of the human TNF-α gene comprises the sequence from the start codon to the stop codon of the human TNF-α gene.

In some embodiments, the sequence of the human TNF-α gene comprises a nucleotide sequence with at least 80% sequence identity, such as at least 85%, at least 90%, at least 95%, at least 98% or at least 99% sequence identity with SEQ ID NO: 61. In a preferred embodiment, the sequence of the human TNF-α gene comprises or consists of SEQ ID NO: 61.

In another aspect, the disclosure relates to a non-human animal cell a sequence of the human IL-17A gene in an expressible form in the genome of the cell.

In some embodiments, the sequence of the human IL-17RA gene is used to replace the corresponding endogenous sequence in the genome of the cell.

In some embodiments, the cell expresses human IL-17RA protein. In other embodiments, the cell expresses humanized IL-17RA protein.

In some embodiments, the human IL-17RA protein comprises an amino acid sequence with at least 80% sequence identity, such as at least 85%, at least 90%, at least 95%, at least 98% or at least 99% sequence identity with SEQ ID NO: 32, or comprises or consists of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with amino acids 49-341 of SEQ ID NO: 32, or comprises or consists of amino acids 49-341 of SEQ ID NO: 32.

In some embodiments, the humanized IL-17RA protein comprises an amino acid sequence with at least 80% sequence identity, such as at least 85%, at least 90%, at least 95%, at least 98% or at least 99% sequence identity with SEQ ID NO: 39, or comprises or consists of SEQ ID NO: 39.

In some embodiments, the sequence of the human IL-17RA gene comprises the coding sequence of the human IL-17RA gene. In other embodiments, the sequence of the human IL-17RA comprises the sequence from exon 2 to exon 11 of the human IL-17RA gene.

In some embodiments, the sequence of the human IL-17RA gene comprises a nucleotide sequence with at least 80% sequence identity, such as at least 85%, at least 90%, at least 95%, at least 98% or at least 99% sequence identity with SEQ ID NO: 35. In a preferred embodiment, the sequence of the human IL-17RA gene comprises or consists of SEQ ID NO: 35.

In some embodiments, the cell is homozygous for the sequence of the human IL-17RA gene. In other embodiments, the cell is heterozygous for the sequence of the human IL-17RA gene.

In some embodiments, in addition to the sequence of the human IL-17RA gene in an expressible form, the genome of the cell may also comprise a sequence of the human TNF-α gene in an expressible form. The cell may be homozygous or heterozygous for the sequence of the human TNF-α gene.

In some embodiments, the sequence of the human TNF-α gene is used to replace the corresponding endogenous sequence in the genome of the cell.

In some embodiments, the cell expresses human TNF-α protein. In some embodiments, the human TNF-α protein comprises an amino acid sequence with at least 80% sequence identity, such as at least 85%, at least 90%, at least 95%, at least 98% or at least 99% sequence identity with SEQ ID NO: 58, or comprises or consists of SEQ ID NO: 58.

In some embodiments, the sequence of the human TNF-α gene comprises the coding sequence of the human TNF-α gene. In some embodiments, the sequence of the human TNF-α gene comprises the sequence from the start codon to the stop codon of the human TNF-α gene.

In some embodiments, the sequence of the human TNF-α gene comprises a nucleotide sequence with at least 80% sequence identity, such as at least 85%, at least 90%, at least 95%, at least 98% or at least 99% sequence identity with SEQ ID NO: 61. In a preferred embodiment, the sequence of the human TNF-α gene comprises or consists of SEQ ID NO: 61.

In any of the above embodiments regarding non-human animal cells, the cells may be rodent cells, such as mouse or rat cells. The mice and rats may be any strain of mice and rats known in the art, for example, any strain of mice and rats described above.

In any of the above embodiments regarding non-human animal cells, the cells may be selected from somatic cells, stem cells such as embryonic stem cells, germ cells, and fertilized eggs.

In one aspect, the disclosure relates to the uses of the non-human animal cells of the disclosure in the production of a genetically-modified non-human animal.

In another aspect, the disclosure relates to uses of the genetically-modified non-human animal and non-human animal cells of the disclosure in screening agents for regulating IL-17A/IL-17RA signaling pathway.

In some embodiments, the agent may be selected from antibodies, antibody fragments, receptors or ligands or a fragment thereof, fusion proteins, and small molecule compounds.

In yet another aspect, the disclosure relates to uses of the genetically-modified non-human animal of the disclosure in constructing a disease model related to abnormal IL-17A/IL-17RA signaling pathway.

In some embodiments, the disease is selected from autoimmune diseases and tumors. In some embodiments, the disease may be selected from multiple sclerosis, asthma, inflammatory bowel disease, psoriasis, rheumatoid arthritis, Crohn's disease, Behcet's disease, systemic lupus erythematosus, primary Sjogren's syndrome, myocarditis, type I diabetes, thyroiditis, atopic dermatitis, hypersensitivity, and graft versus host disease.

In one aspect, the disclosure relates to uses of the IL-17A humanized animal of the disclosure in testing the in vivo effectiveness of an agent targeting human IL-17A.

In some embodiments, the agent is selected from an antibody or antibody fragment or a small molecule antagonist against human IL-17A.

In some embodiments, the genetically-modified non-human animal is used to construct a disease model related to abnormal IL-17A signaling pathway, and to test the in vivo effectiveness of the agent in the disease model.

In some embodiments, the disease model is an autoimmune disease model, for example selected from experimental autoimmune encephalomyelitis (EAE) model and psoriasis model. In some embodiments, the psoriasis model is an imiquimod-induced psoriasis model.

In another aspect, the disclosure relates to a method for detecting the in vivo effectiveness of an agent targeting human IL-17A, comprising:

a. constructing a disease model associated with abnormal IL-17A signaling pathway using the IL-17A humanized animals of the disclosure;

b. administering the agent targeting human IL-17A to the disease model animal; and c. evaluating the in vivo effectiveness of the agent targeting IL-17A.

In some embodiments, the agent is selected from an antibody or antibody fragment and a small molecule antagonist against human IL-17A.

In some embodiments, the disease model is an autoimmune disease model, for example selected from experimental autoimmune encephalomyelitis (EAE) model and psoriasis model. In some embodiments, the psoriasis model is an imiquimod-induced psoriasis model.

Targeting Vector

In one aspect, the disclosure relates to a targeting vector comprising the coding sequence or the sequence from the start codon to the stop codon of the human IL-17A gene, and the upstream and downstream homologous arm sequences of the mouse IL-17A gene.

As used herein, the term "targeting vector" refers to a vector that can be integrated into the genome of a host cell after being introduced into the host cell, thereby replicating together with the host genome. Generally, expression vectors useful in recombinant DNA technology are usually in the form of plasmids. However, the disclosure is intended to include other forms of expression vectors, such as viral vectors (e.g., replication defective retroviruses, adenoviruses, and adeno-associated viruses), which perform equivalent functions.

In some embodiments, the sequence of the human IL-17A gene comprises a nucleotide sequence with at least 80% sequence identity, such as at least 85%, at least 90%, at least 95%, at least 98% or at least 99% sequence identity with SEQ ID NO: 7. In a preferred embodiment, the sequence of the human IL-17A gene comprises or consists of SEQ ID NO: 7.

In some embodiments, each of the upstream and downstream homology arm sequences of the mouse IL-17A gene comprises at least 100 nucleotides, for example at least 200 nucleotides, at least 300 nucleotides, at least 500 nucleotides, at least 1,000 nucleotides, at least 2,000 nucleotides, or at least 3,000 nucleotides, such as 100-500 nucleotides, 500-1,000 nucleotides, 1,000-2,000 nucleotides, 2,000-3,000 nucleotides, 3,000-5,000 nucleotides or 5,000-10,000 nucleotides. Preferably, each of the upstream and downstream homology arm sequences of the mouse IL-17RA gene comprises 3,000 to 5,000 nucleotides.

In a preferred embodiment, the upstream homology arm sequence of the mouse IL-17A gene comprises SEQ ID NO: 5, and the downstream homology arm sequence of the mouse IL-17A gene comprises SEQ ID NO: 6.

In another aspect, the disclosure relates to a targeting vector comprising the coding sequence or the sequence from exon 2 to exon 11 of the human IL-17RA gene, and the upstream and downstream homologous arm sequences of the mouse IL-17RA gene.

In some embodiments, the sequence of the human IL-17RA gene comprises a nucleotide sequence with at least 80% sequence identity, such as at least 85%, at least 90%, at least 95%, at least 98% or at least 99% sequence identity with SEQ ID NO: 31 or SEQ ID NO: 35. In a preferred embodiment, the sequence of the human IL-17RA gene comprises or consists of SEQ ID NO: 35.

In some embodiments, each of the upstream and downstream homology arm sequences of the mouse IL-17RA gene comprises at least 100 nucleotides, for example at least 200 nucleotides, at least 300 nucleotides, at least 500 nucleotides, at least 1,000 nucleotides, at least 2,000 nucleotides, or at least 3,000 nucleotides, such as 100-500 nucleotides, 500-1,000 nucleotides, 1,000-2,000 nucleotides, 2,000-3,000 nucleotides, 3,000-5,000 nucleotides or 5,000-10,000 nucleotides. Preferably, each of the upstream and downstream homology arm sequences of the mouse IL-17RA gene comprises 3,000 to 5,000 nucleotides.

In a preferred embodiment, the upstream homology arm sequence of the mouse IL-17RA gene comprises SEQ ID NO: 33, and the downstream homology arm sequence of the mouse IL-17RA gene comprises SEQ ID NO: 34.

In yet another aspect, the disclosure relates to a targeting vector comprising the coding sequence or the sequence from the start codon to the stop codon of the human TNF-α gene and the upstream and downstream homology arm sequences of the mouse TNF-α gene.

In some embodiments, the targeting vector comprises the sequence from the start codon to the stop codon of the human TNF-α gene and the upstream and downstream homology arm sequences of the mouse TNF-α gene.

In some embodiments, the sequence of the human TNF-α gene comprises a nucleotide sequence with at least 80% sequence identity, such as at least 85%, at least 90%, at least 95%, at least 98% or at least 99% sequence identity with SEQ ID NO: 61. In a preferred embodiment, the sequence of the human TNF-α gene comprises or consists of SEQ ID NO: 61.

In some embodiments, each of the upstream and downstream homology arm sequences of the mouse TNF-α gene comprises at least 100 nucleotides, for example at least 200 nucleotides, at least 300 nucleotides, at least 500 nucleotides, at least 1,000 nucleotides, at least 2,000 nucleotides, or at least 3,000 nucleotides, such as 100-500 nucleotides, 500-1,000 nucleotides, 1,000-2,000 nucleotides, 2,000-3,000 nucleotides, 3,000-7,000 nucleotides or 7,000-10,000 nucleotides. Preferably, each of the upstream and downstream homology arm sequences of the mouse TNF-α gene comprises 3,000 to 7,000 nucleotides.

In a preferred embodiment, the upstream homology arm sequence of the mouse TNF-α gene comprises SEQ ID NO: 59, and the downstream homology arm sequence of the mouse TNF-α gene comprises SEQ ID NO: 60.

In any embodiment regarding a targeting vector, the targeting vector may further comprise a resistance gene for positive screening. In some embodiments, the resistance gene is the coding sequence of neomycin phosphotransferase.

It is usually beneficial to avoid reporter genes because there is no need remove them later. However, the expression of the reporter gene at the embryo/modification stage at cell level allows the exclusion of cells that do not express the reporter gene. Alternatively, it allows the selection of cells expressing the reporter gene for use in animals by cloning or by other genetically-modified animal technology, or for being transferred to a second culture for further cultivation and/or number expansion and/or addition of other vectors and/or nucleic acids and/or other genetic modifications. Selecting cells based on the expression of reporter gene which does not depend on the gene of interest is a co-selection method. The term reporter gene, as used herein, includes reporter genes and selectable markers. The term selectable marker, as used herein, refers to genetically expressed biomolecules that allow separation by selection criteria for positive or negative survival. The reporter gene may be, for example, a fluorescent marker such as green fluorescent protein and yellow fluorescent protein. The reporter gene may be a selectable marker, such as puromycin, ganciclovir, adenosine deaminase (ADA), aminoglycoside phosphotransferase (neo, G418, APH), dihydrofolate reductase (DHFR), Hygromycin-B-phosphotransferase, thymidine kinase (TK), or xanthine-guanine phosphoribosyltransferase (XGPRT). For example, cells can be removed from culture and used for cloning. Alternatively, cells can be removed from the culture and placed in a second culture to establish a clony or use in further experiments. Alternatively, embryos or fertilized eggs expressing the reporter gene can be used for implantation into surrogate animals or for cloning, while other embryos or fertilized eggs that do not express the reporter gene are not used for cloning. In some embodiments, the reporter gene is a selectable marker, which is used to select cells or embryos expressing the marker.

In some embodiments, the targeting vector further includes a marker gene for negative screening. In some embodiments, the marker gene is the coding sequence of diphtheria toxin A subunit.

In any embodiment regarding the targeting vector, the vector can be used to replace the corresponding endogenous gene sequence in the mouse genome.

In yet another aspect, the disclosure relates to uses of the targeting vector of the disclosure in replacing the corresponding endogenous gene sequence in the mouse genome.

In another aspect, the disclosure relates to uses of the targeting vector of the disclosure in constructing a genetically-modified mouse or a genetically-modified mouse cell.

Methods of Making Genetically Modified Animals

In one aspect, the disclosure relates to a method for producing a genetically-modified non-human animal containing a sequence of the human IL-17A gene, comprising inserting the sequence of the human IL-17A gene into the genome of the animal.

In some embodiments, the sequence of the human IL-17A gene is used to replace the corresponding endogenous sequence in the genome of the animal.

In some embodiments, the animal is a rodent, such as a mouse.

In some embodiments, the method comprises the following steps:

a. providing the targeting vector comprising the coding sequence or the sequence from the start codon to the stop codon of the human IL-17A gene, and the upstream and downstream homologous arm sequences of the mouse IL-17A gene of the disclosure;

b1. injecting the targeting vector into a fertilized egg of a mouse;

c1. transplanting the fertilized egg into a surrogate mother mouse and breeding, to obtain the genetically-modified mouse; or b2. injecting the targeting vector into an embryonic stem cell of a mouse;

c2. generating the genetically-modified mouse by the embryonic stem cell.

Methods for preparing colonies from cultured cells are known. One of such method involves dispersing cells from a first culture into a second culture, in which individual cells do not contact each other, for example, by diluting the cells into a multi-well plate, or into a dish having a relatively large surface area relative to the number of total cells in the dish. The cells are cultured for a period of time to proliferate. Proliferating cells are cultured under conditions in which they are unlikely to move far from their original location. As a result, after a period of time, the user can observe the cells and see the individual colonies established by single cell and its progeny. It is possible to sample a subset of cells in a colony without disturbing other cells in the colony.

In some embodiments, step c2 comprises introducing the embryonic stem cell into an isolated blastocyst, and transplanting the obtained chimeric blastocysts into a surrogate mother mouse, and breeding to obtain the genetically-modified mouse.

In some embodiments, the method further comprises the step of detecting the offspring of the surrogate mother mouse to screen genetically-modified mouse containing the sequence of the human IL-17A gene sequence in the genome.

In some embodiments, the method further comprises the step of crossing the genetically-modified mice to obtain a mouse homozygous for the sequence of the human IL-17A gene.

In another aspect, the disclosure relates to a method of producing a genetically-modified animal containing a sequence of the human IL-17RA gene, comprising inserting the sequence of the human IL-17RA gene into the genome of the animal.

In some embodiments, the sequence of the human IL-17RA gene is used to replace the corresponding endogenous sequence in the genome of the animal.

In some embodiments, the method comprises the following steps:

a. providing a targeting vector comprising the coding sequence or the sequence from exon 2 to exon 11 of the human IL-17RA gene, and the upstream and downstream homologous arm sequences of the mouse IL-17RA gene;

b1. injecting the targeting vector into a fertilized egg of a mouse;

c1. transplanting the fertilized egg into a surrogate mother mouse and breeding, to obtain the genetically-modified mouse; or b2. injecting the targeting vector into an embryonic stem cell of a mouse;

c2. generating the genetically-modified mouse by the embryonic stem cell.

In some embodiments, step c2 comprises introducing the embryonic stem cell into an isolated blastocyst, and transplanting the obtained chimeric blastocysts into a surrogate mother mouse, and breeding to obtain the genetically-modified mouse.

In some embodiments, the method further comprises the step of detecting the offspring of the surrogate mother mouse to screen genetically-modified mice containing the sequence of the human IL-17RA gene sequence in the genome.

In some embodiments, the method further comprises the step of crossing the genetically-modified mice to obtain a mouse homozygous for the sequence of the human IL-17RA gene.

In another aspect, the disclosure relates to a method for producing a genetically-modified non-human animal containing a sequence of the human TNF-α gene, comprising inserting the sequence of the human TNF-α gene into the genome of the animal.

In some embodiments, the sequence of the human TNF-α gene is used to replace the corresponding endogenous sequence in the genome of the animal.

In some embodiments, the method comprises the following steps:

a. providing a targeting vector comprising the coding sequence or the sequence from the start codon to the stop codon of the human TNF-α gene and the upstream and downstream homology arm sequences of the mouse TNF-α gene.

b1. injecting the targeting vector into a fertilized egg of a mouse;

c1. transplanting the fertilized egg into a surrogate mother mouse and breeding, to obtain the genetically-modified mouse; or b2. injecting the targeting vector into an embryonic stem cell of a mouse;

c2. generating the genetically-modified mouse by the embryonic stem cell.

In some embodiments, step c2 comprises introducing the embryonic stem cell into an isolated blastocyst, and transplanting the obtained chimeric blastocysts into a surrogate mother mouse, and breeding to obtain the genetically-modified mouse.

In some embodiments, the method further comprises the step of detecting the offspring of the surrogate mother mouse to screen genetically-modified mice containing the sequence of the human TNF-α gene in the genome.

In some embodiments, the method further comprises the step of crossing the genetically-modified mice to obtain a mouse homozygous for the sequence of the human TNF-α gene.

In any embodiment of the above methods, the animal may be a rodent, such as a rat or a mouse. In a preferred embodiment, the animal is a mouse.

The present disclosure also includes a genetically-modified non-human animal, such as a genetically-modified mouse, comprising a sequence of the human IL-17A gene, a sequence of the human IL-17RA gene, or a sequence of the human TNF-α gene, produced by the method of the disclosure.

In another aspect, the disclosure relates to a method for producing a genetically-modified non-human animal, such as a genetically-modified mouse, containing a sequence of the human IL-17A gene and a sequence of the human IL-17RA gene, comprising crossing a genetically-modified non-human animal, such as a genetically-modified mouse, having a sequence of the human IL-17A gene and a genetically-modified non-human animal, such as a genetically-modified mouse, having a sequence of the human IL-17RA gene of the disclosure.

In another aspect, the disclosure relates to a method for producing a genetically-modified non-human animal, such as a genetically-modified mouse, containing a sequence of the human IL-17A gene and a sequence of the human TNF-α gene, comprising crossing a genetically-modified non-human animal, such as a genetically-modified mouse, having a sequence of the human IL-17A gene and a genetically-modified non-human animal, such as a genetically-modified mouse, having a sequence of the human TNF-α gene of the disclosure.

In another aspect, the disclosure relates to a method for producing a genetically-modified non-human animal, such as a genetically-modified mouse, containing a sequence of the human IL-17RA gene and a sequence of the human TNF-α gene, comprising crossing a genetically-modified non-human animal, such as a genetically-modified mouse, having a sequence of the human IL-17RA gene and a genetically-modified non-human animal, such as a genetically-modified mouse, having a sequence of the human TNF-α gene of the disclosure.

In another aspect, the disclosure relates to a method for producing a genetically-modified non-human animal, such as a genetically-modified mouse, containing a sequence of the human IL-17A gene, a sequence of the human IL-17RA gene, and a sequence of the human TNF-α gene, comprising crossing a genetically-modified non-human animal, such as a genetically-modified mouse, having a sequence of the human IL-17A gene, a genetically-modified non-human animal, such as a genetically-modified mouse, having a sequence of the human IL-17RA gene, and a genetically-modified non-human animal, such as a genetically-modified mouse, having a sequence of the human TNF-α gene of the disclosure.

In yet another aspect, the disclosure relates to a method for producing a genetically-modified non-human animal, such as a genetically-modified mouse, having a sequence of the human IL-17A gene and a sequence of the human IL-17RA gene, comprising a1. providing a fertilized egg or an embryonic stem cell obtained from a genetically-modified non-human animal, such as a genetically-modified mouse, having a sequence of the human IL-17A gene of the disclosure;

b1. in the fertilized egg or embryonic stem cell, inserting a sequence of the human IL-17RA gene into the genome of the genetically-modified non-human animal, such as the genetically-modified mouse, by the method of the disclosure, thereby generating a genetically-modified mouse comprising a sequence of the human IL-17A gene and a sequence of the human IL-17RA gene; or a2. providing a fertilized egg or an embryonic stem cell obtained from a genetically-modified non-human animal, such as a genetically-modified mouse, having a sequence of the human IL-17RA gene of the disclosure;

b2. in the fertilized egg or embryonic stem cell, inserting a sequence of the human IL-17A gene into the genome of the genetically-modified non-human animal, such as the genetically-modified mouse, by the method of the disclosure, thereby generating a genetically-modified mouse comprising a sequence of the human IL-17A gene and a sequence of the human IL-17RA gene.

In yet another aspect, the disclosure relates to a method for producing a genetically-modified non-human animal, such as a genetically-modified mouse, having a sequence of the human IL-17A gene and a sequence of the human TNF-α gene, comprising a1. providing a fertilized egg or an embryonic stem cell obtained from a genetically-modified non-human animal, such as a genetically-modified mouse, having a sequence of the human IL-17A gene of the disclosure;

b1. in the fertilized egg or embryonic stem cell, inserting a sequence of the human TNF-α gene into the genome of the genetically-modified non-human animal, such as the genetically-modified mouse, by the method of the disclosure, thereby generating a genetically-modified mouse comprising a sequence of the human IL-17A gene and a sequence of the human TNF-α gene; or a2. providing a fertilized egg or an embryonic stem cell obtained from a genetically-modified non-human animal, such as a genetically-modified mouse, having a sequence of the human TNF-α gene of the disclosure;

b2. in the fertilized egg or embryonic stem cell, inserting a sequence of the human IL-17A gene into the genome of the genetically-modified non-human animal, such as the genetically-modified mouse, by the method of the disclosure, thereby generating a genetically-modified mouse comprising a sequence of the human IL-17A gene and a sequence of the human TNF-α gene.

In yet another aspect, the disclosure relates to a method for producing a genetically-modified non-human animal, such as a genetically-modified mouse, having a sequence of the human IL-17RA gene and a sequence of the human TNF-α gene, comprising a1. providing a fertilized egg or an embryonic stem cell obtained from a genetically-modified non-human animal, such as a genetically-modified mouse, having a sequence of the human IL-17RA gene of the disclosure;

b1. in the fertilized egg or embryonic stem cell, inserting a sequence of the human TNF-α gene into the genome of the genetically-modified non-human animal, such as the genetically-modified mouse, by the method of the disclosure, thereby generating a genetically-modified mouse comprising a sequence of the human IL-17RA gene and a sequence of the human TNF-α gene; or a2. providing a fertilized egg or an embryonic stem cell obtained from a genetically-modified non-human animal, such as a genetically-modified mouse, having a sequence of the human TNF-α gene of the disclosure;

b2. in the fertilized egg or embryonic stem cell, inserting a sequence of the human IL-17RA gene into the genome of the genetically-modified non-human animal, such as the genetically-modified mouse, by the method of the disclosure, thereby generating a genetically-modified mouse comprising a sequence of the human IL-17RA gene and a sequence of the human TNF-α gene.

Polypeptide and Polynucleotide Encoding the Same

In one aspect, the disclosure relates to a polypeptide comprises an amino acid sequence with at least 80% sequence identity, such as at least 85%, at least 90%, at least 95%, at least 98% or at least 99% sequence identity with SEQ ID NO: 39. In some embodiments, the polypeptide comprises or consists of SEQ ID NO: 39.

In another aspect, the disclosure relates to a polynucleotide encoding the polypeptide of the disclosure. In some embodiments, the polynucleotide comprises SEQ ID NO: 38.

In yet another aspect, the disclosure relates to a vector comprising the polynucleotide of the disclosure.

In one aspect, the disclosure relates to a chimeric IL17-RA gene comprising a partial human IL-17RA gene sequence and a partial non-human animal IL-17RA gene sequence, preferably, all or part of the partial human IL17RA gene sequence has at least 85%, at least 90%, at least 95%, at least 98% or at least 99% identity with SEQ ID NO: 35, SEQ ID NO: 36 or SEQ ID NO: 37, and more preferably, the partial human IL17RA gene sequence is SEQ ID NO: 35.

In another aspect, the disclosure relates to a chimeric TNF-α gene comprising a partial human TNF-α gene sequence and a partial non-human animal TNF-α gene sequence, preferably, the partial human TNF-α gene sequence has at least 85%, at least 90%, at least 95%, at least 98% or at least 99% identity with SEQ ID NO: 61, and more preferably, the partial human TNF-α gene sequence is SEQ ID NO: 61

In one aspect, the disclosure relates to a chimeric IL-17A gene comprising a partial human IL-17A gene sequence and a partial non-human animal IL-17A gene sequence, preferably, all or part of the partial human IL-17A gene sequence has at least 85%, at least 90%, at least 95%, at least 98% or at least 99% identity with SEQ ID NO: 7, SEQ ID NO: 8 or SEQ ID NO: 9, and more preferably, the partial human IL-17A gene sequence is SEQ ID NO: 7.

DESCRIPTION OF DRAWINGS

Herein after, the embodiments of the disclosure will be described in detail with reference to the accompanying drawings.

panel (C), use primer pair Frt-F and Frt-R to amplify the neo fragment to verify whether the resistance gene is removed; and panel (D), use primer pair Flp-F2 and Flp-R2 to confirm the presence of the Flp fragment; in which, WT: wild-type mouse, M: Marker, and PC: positive control.

Figure 7:
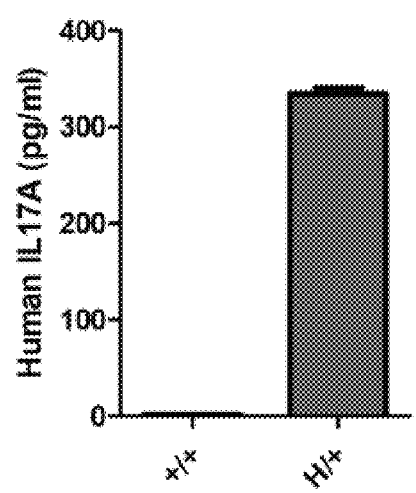

FIG. 7: ELISA test results of human IL-17A.

Figure 8:
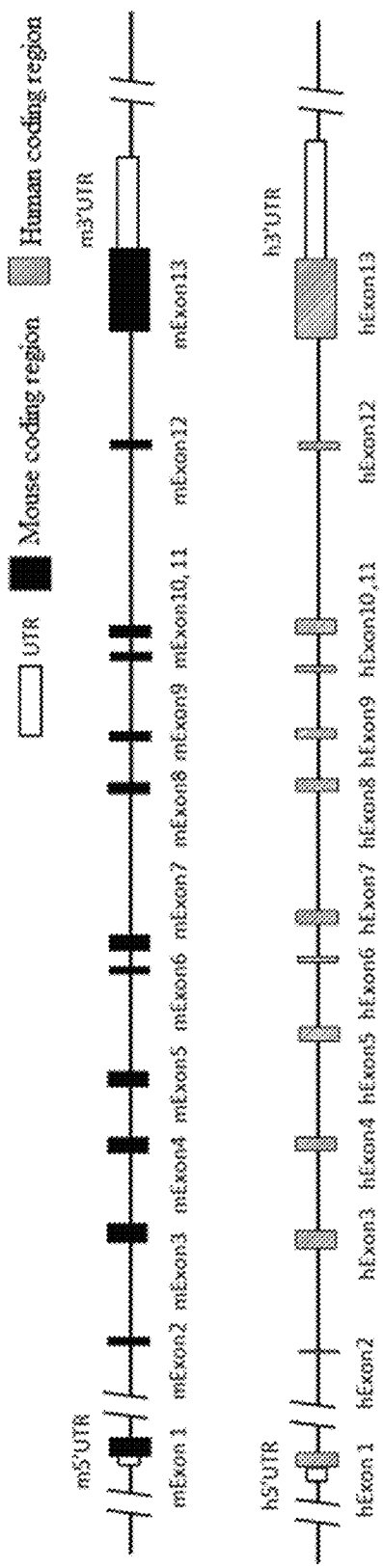

FIG. 8: Schematic diagram showing mouse IL-17RA gene compared with human IL-17RA gene (not to scale).

Figure 9:
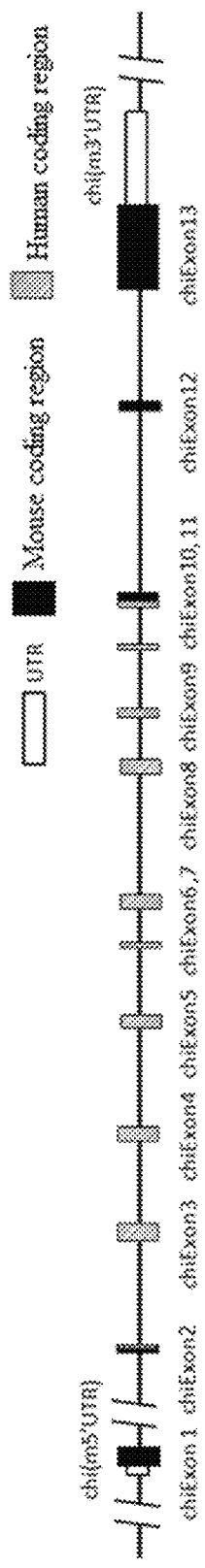

FIG. 9: Schematic diagram showing humanized mouse IL-17RA gene (not to scale).

Figure 10:
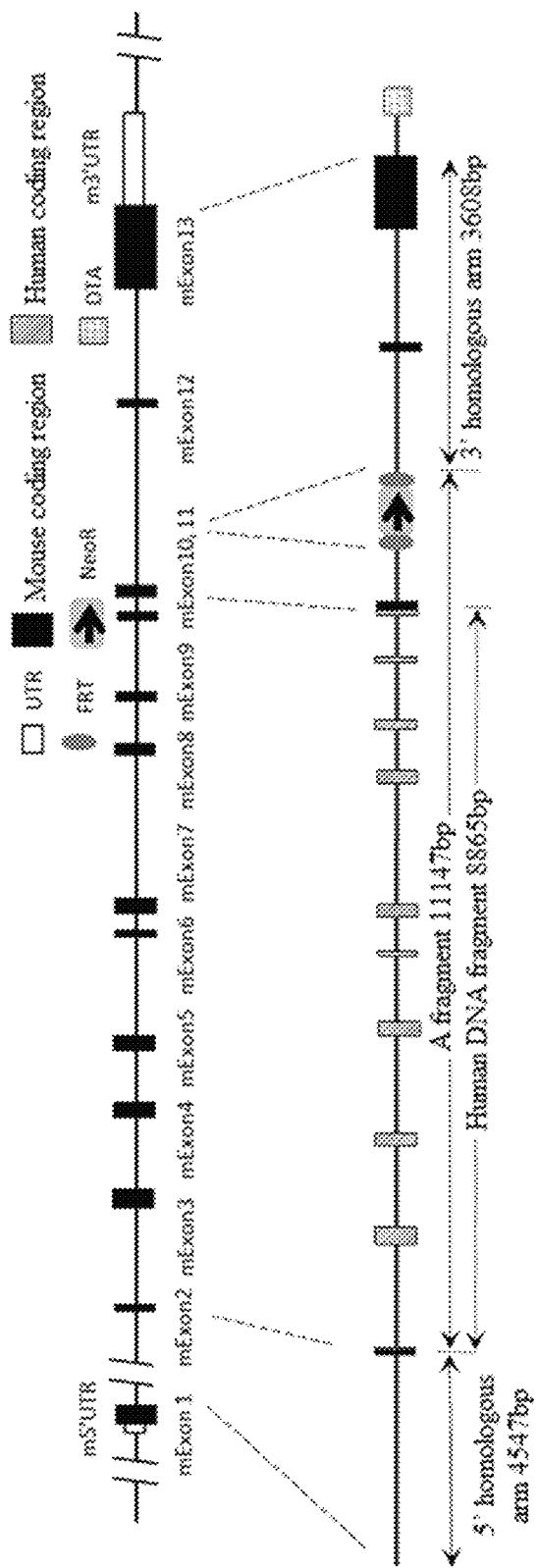

FIG. 10: Schematic diagram showing the targeting strategy for replacing the mouse endogenous IL-17RA gene sequence with a targeting vector containing the human IL-17RA gene sequence (not to scale).

Figure 11:
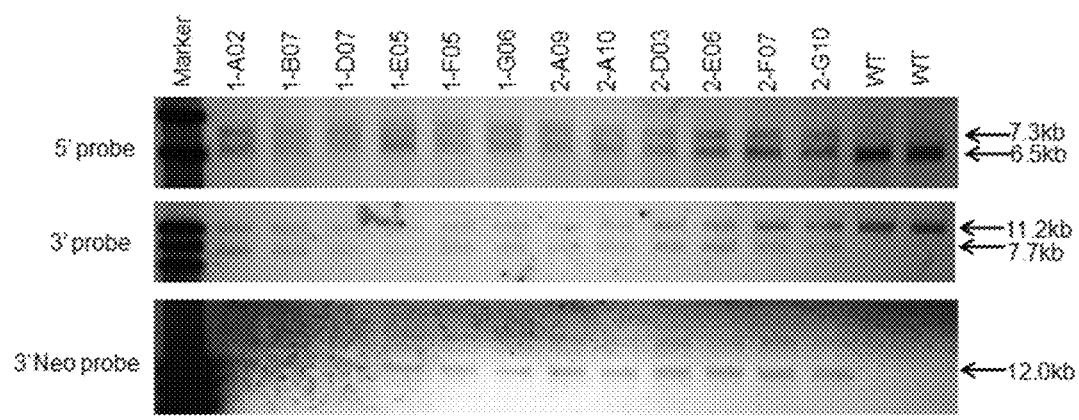

FIG. 11: Southern Blot results from different positive cell colonies, in which WT refers to a wild-type control.

Figure 12:
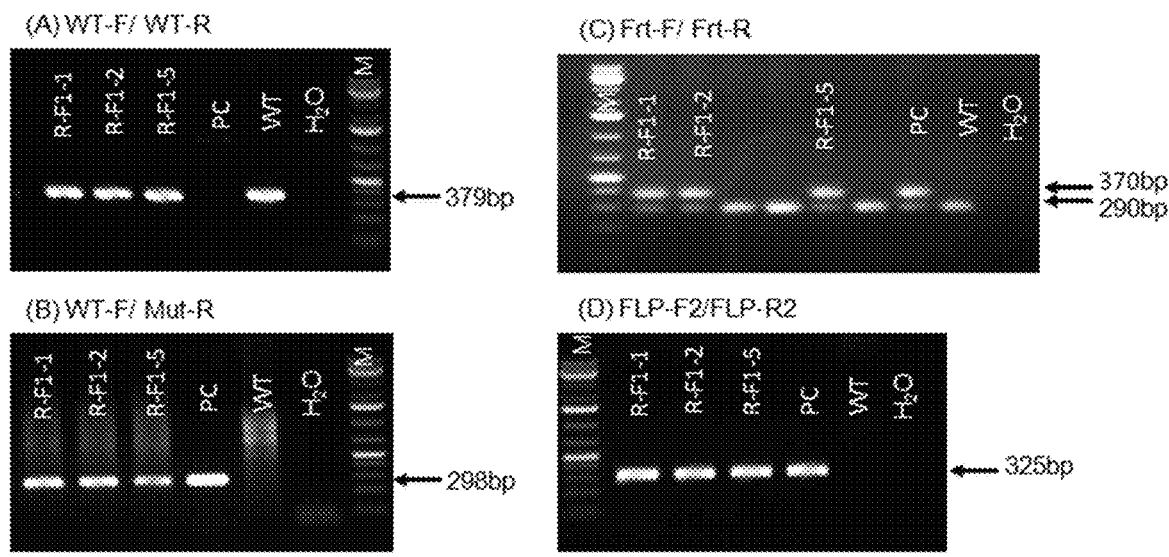

FIG. 12: tail vein PCR identification results for F1 generation mouse, in which: panel (A), use primer pair WT-F and WT-R to amplify the endogenous mouse wild-type IL-17RA gene fragment; panel (B), use primer pair WT-F and Mut-R to amplify the modified IL-17RA gene fragment to verify whether the targeting vector is correctly inserted into the mouse genome site; panel (C), use primer pair Frt-F and Frt-R to amplify the neo fragment to verify whether the resistance gene is removed; and panel (D), use primer pair Flp-F2 and Flp-R2 to confirm the presence of the Flp fragment; in which, WT: wild-type, M: marker, and PC: positive control.

Figure 13:
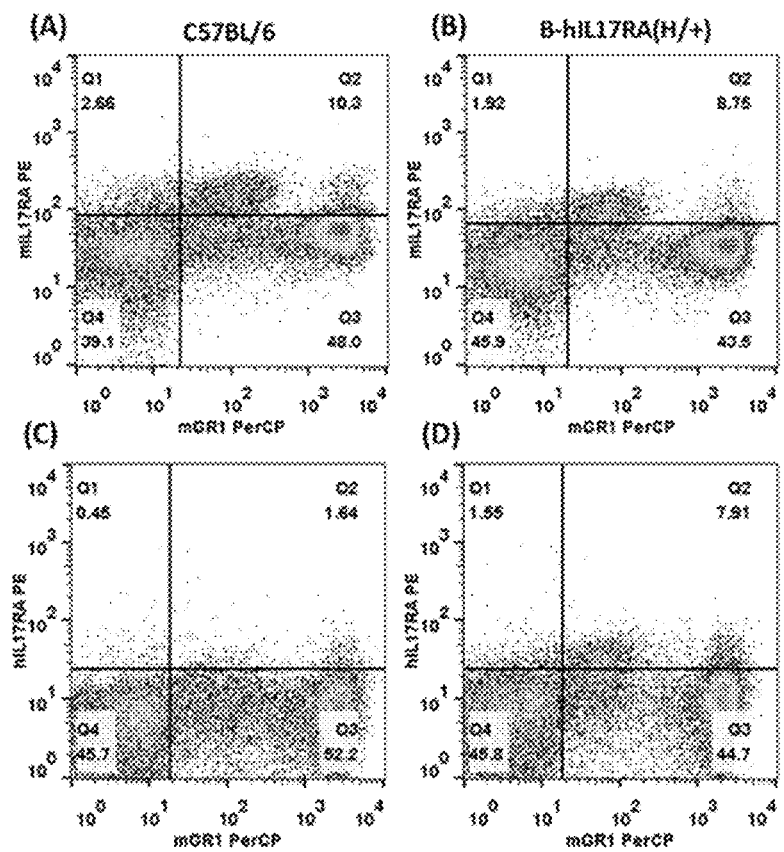

FIG. 13: Results of flow cytometric analysis of C57BL/6 wild-type mice (panels (A) and (C)) and IL-17RA humanized genetically-modified mice (panels (B) and (D)) using mIL-17RA PE (panels (A) and (C)) or hIL-17RA PE (panels (B) and (D)) and mGR1PerCP for cell labeling.

Figure 14:
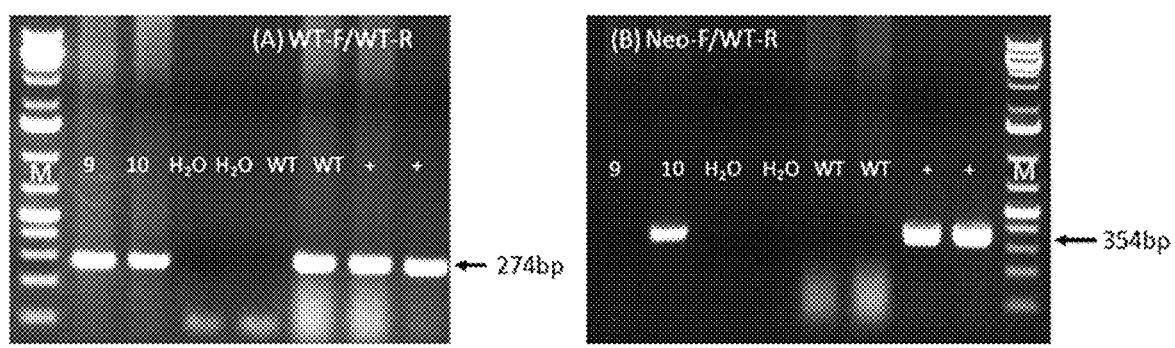

FIG. 14: tail vein PCR identification results for F1 generation mouse, in which: panel (A), use primer pair WT-F and WT-R to amplify the endogenous mouse wild-type TNF-α gene fragment; panel (B), use primer pair Neo-F and WT-R to amplify modified TNF-α gene fragments to verify whether the neo fragments are present and inserted into the genome site correctly; in which, WT: wild type, M: marker, and +: positive control.

Figure 15:
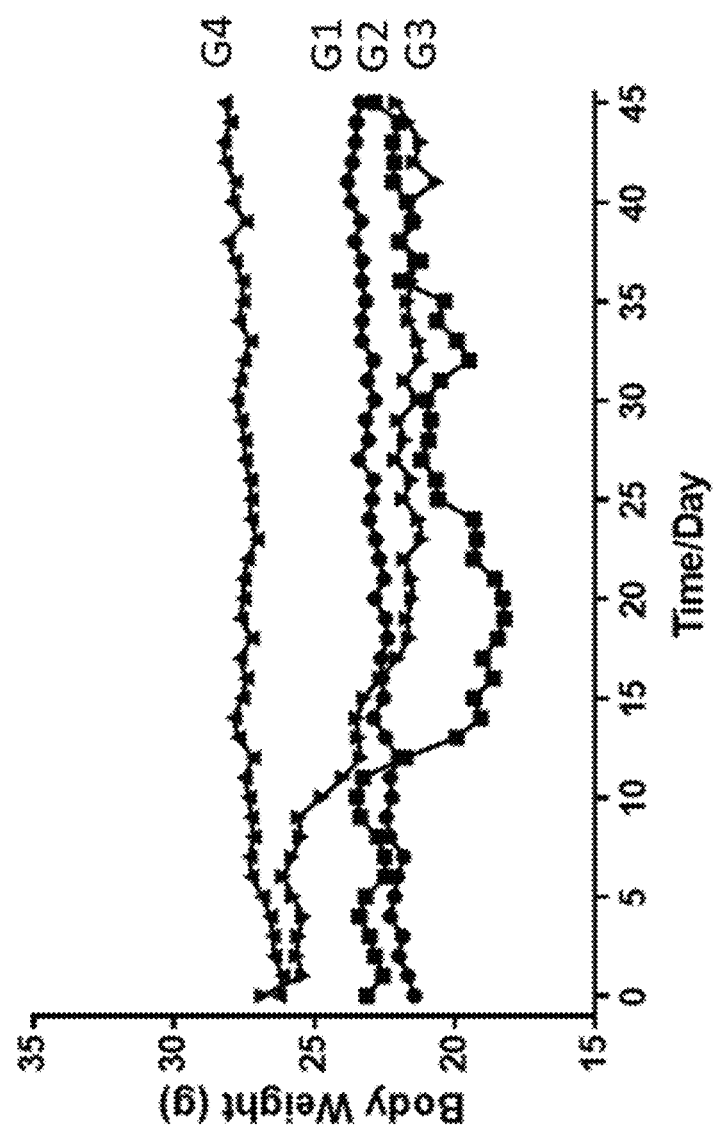

FIG. 15: A graph of the body weight of mice over time, in the MOG-induced EAE model and the control group (no induction) of IL-17A gene humanized mouse homozygotes. G1 and G3 are control groups; G2 and G4 are EAE models.

Figure 16:
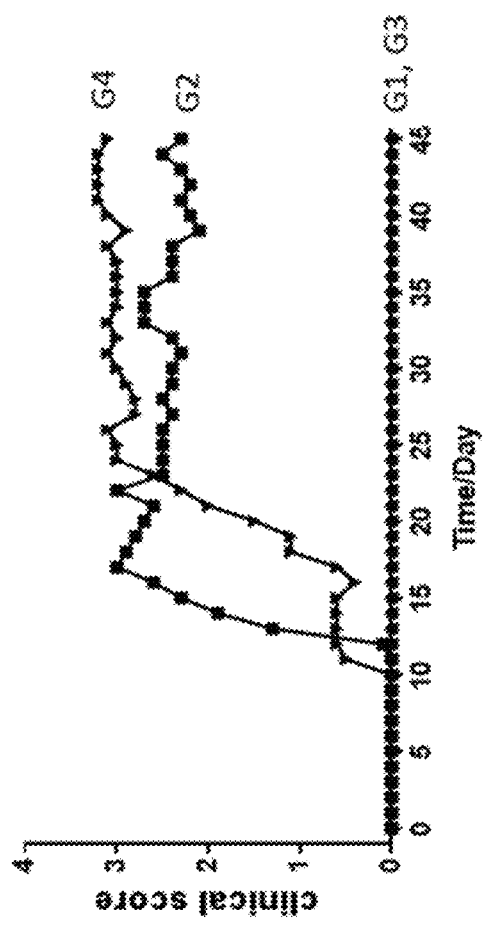

FIG. 16: A graph of the clinical score of mice over time, in the MOG-induced EAE model and the control group using mouse homozygotes for humanized IL-17A gene. G1 and G3 are control groups; G2 and G4 are EAE models.

Figure 17:
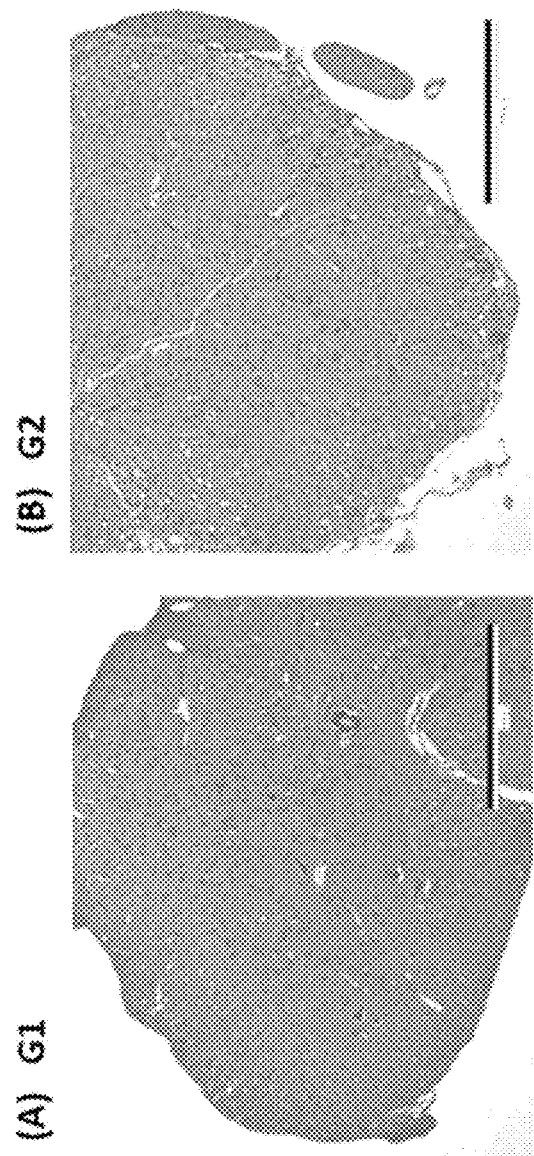

FIG. 17: HE staining results (100×) of spinal cord tissue sections from the MOG-induced EAE model and the control group of mice homozygous for humanized IL-17A gene, 45 day after the induction. G1 is the control group, and G2 is the EAE model.

Figure 18:
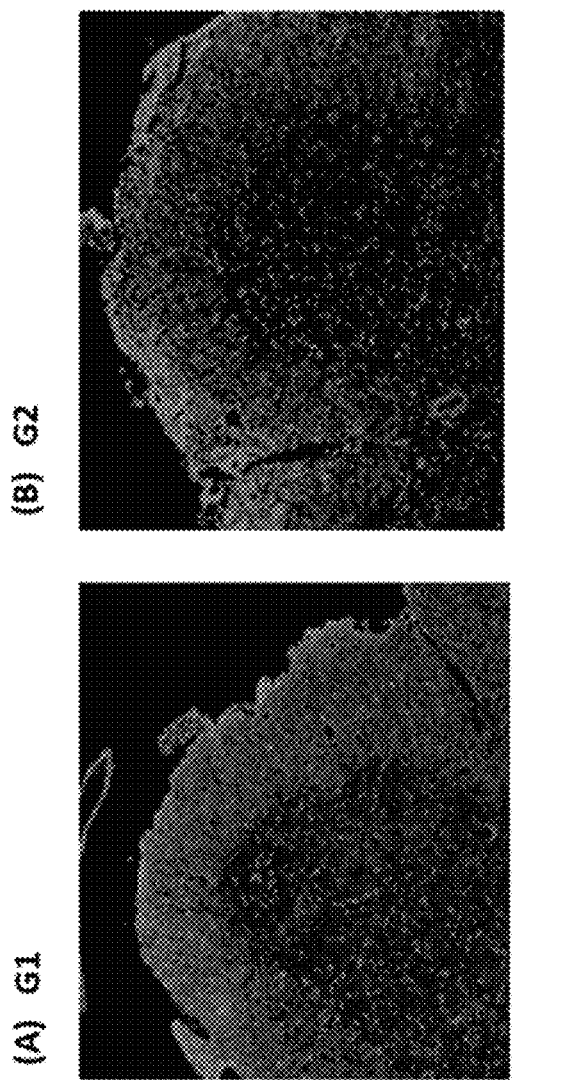

FIG. 18: Immunohistochemical staining results (100×) of spinal cord tissue sections from the MOG-induced EAE model and the control group of mice homozygous for humanized IL-17A gene, 45 day after the induction. Green: MBP; blue: DAPI. G1 is the control group, and G2 is the EAE model.

Figure 19:
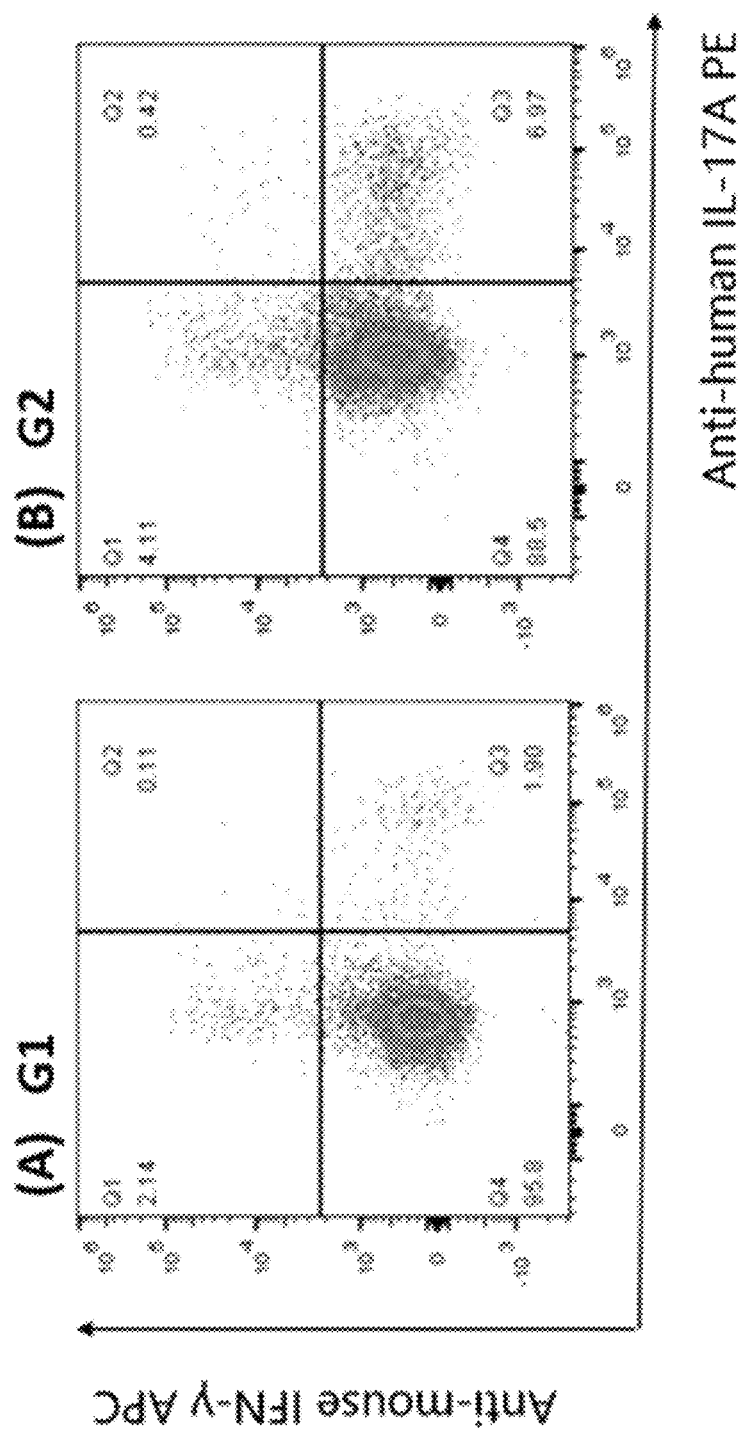

FIG. 19: Exemplary FACS results for detecting IL-17 and IFNγ in lymph nodes in vitro from the MOG-induced EAE model and the control group of mice homozygous for humanized IL-17A gene, 45 day after the induction. Panel A shows the result of a mouse from the control group G1, and panel B shows the result of a mouse from the model group G2.

Figure 20:
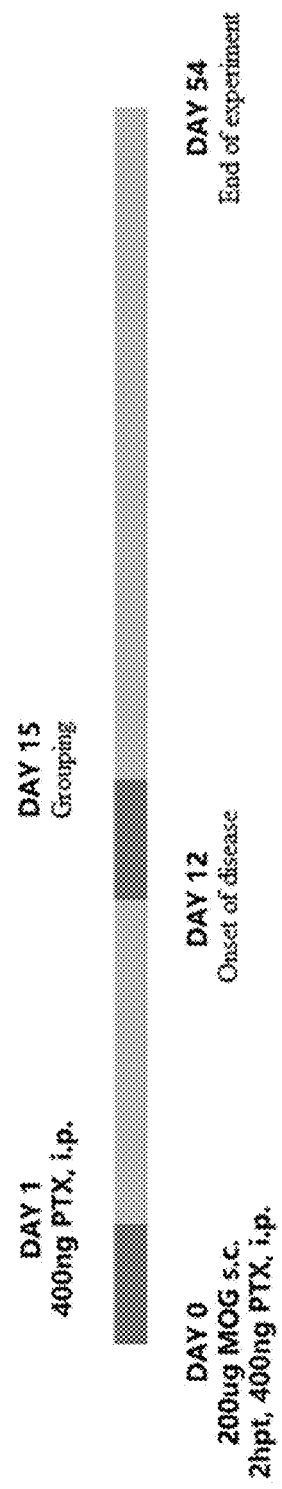

FIG. 20: Experimental flow chart for evaluating the effectiveness of anti-human IL-17A antibodies in the MOG-induced EAE model of mice homozygous for humanized IL-17A gene.

Figure 21:
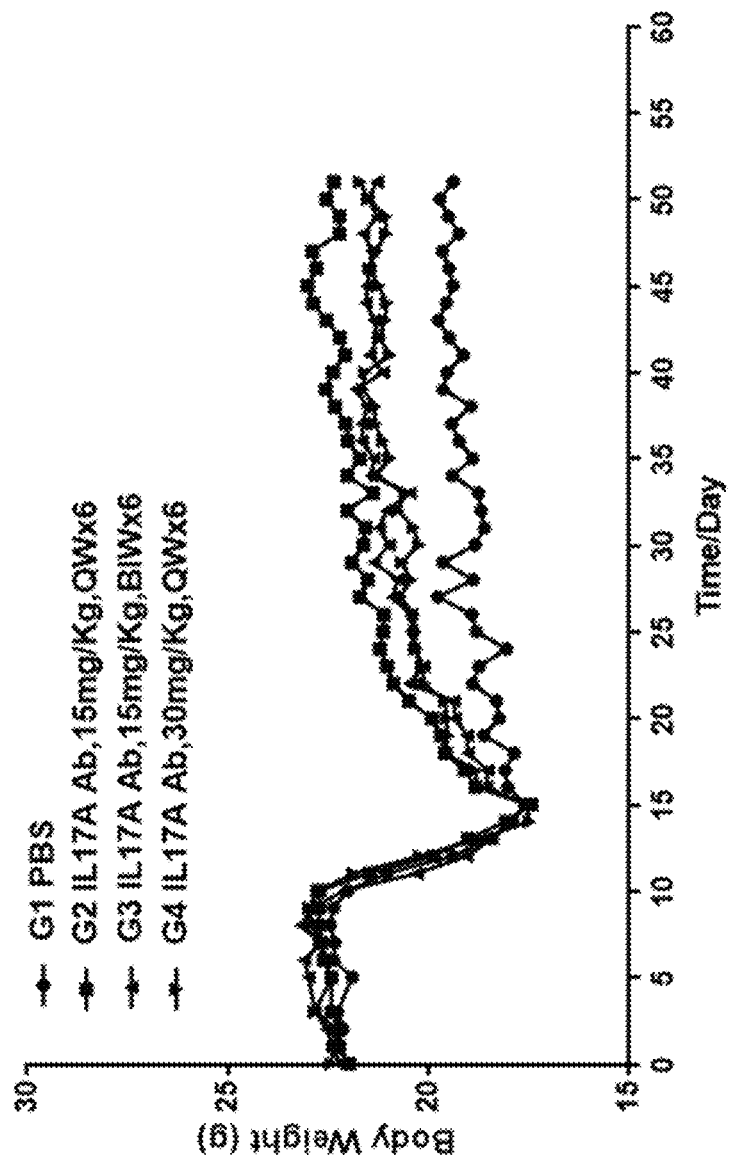

FIG. 21: A statistical graph of body weights of mice in the anti-human IL-17A antibody treatment group and the control group (PBS), in MOG-induced EAE models of mice homozygous for humanized IL-17A gene.

Figure 22:
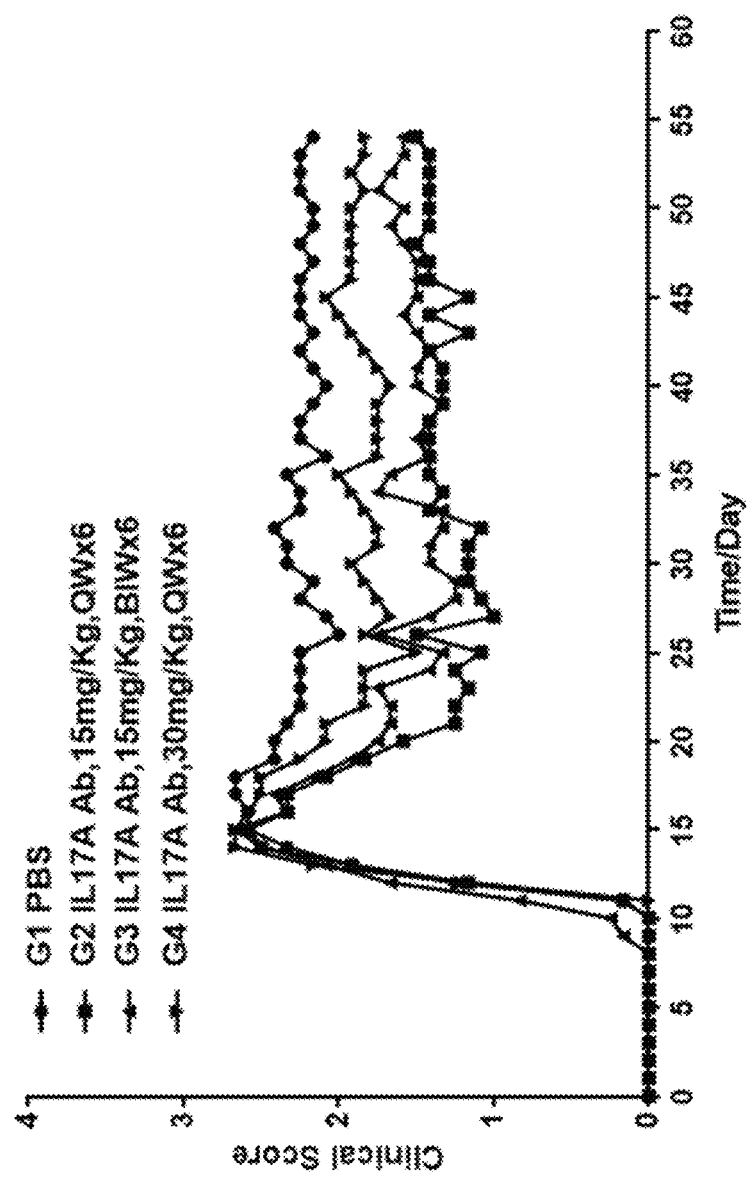

FIG. 22: A statistical graph of clinical scores of mice in the anti-human IL-17A antibody treatment group and the control group, in MOG-induced EAE models of mice homozygous for humanized IL-17A gene.

Figure 23:
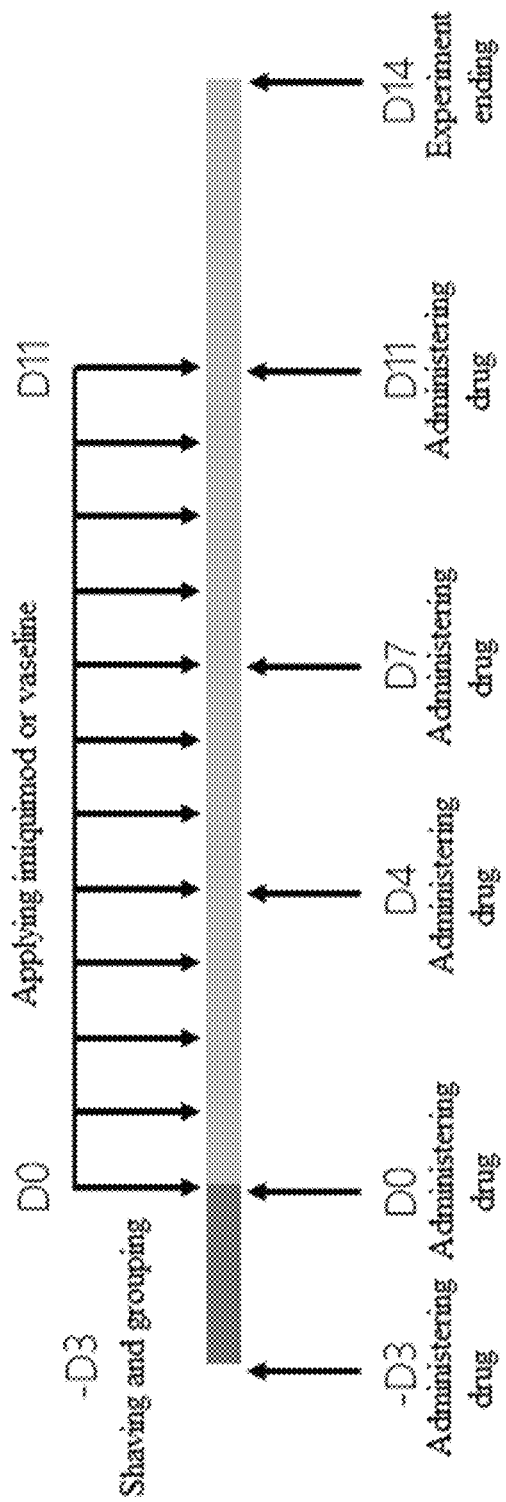

FIG. 23: Experimental flow chart for evaluating the effectiveness of anti-human IL-17A antibodies in imiquimod-induced psoriasis model of mice homozygous for humanized IL-17A gene.

Figure 24:
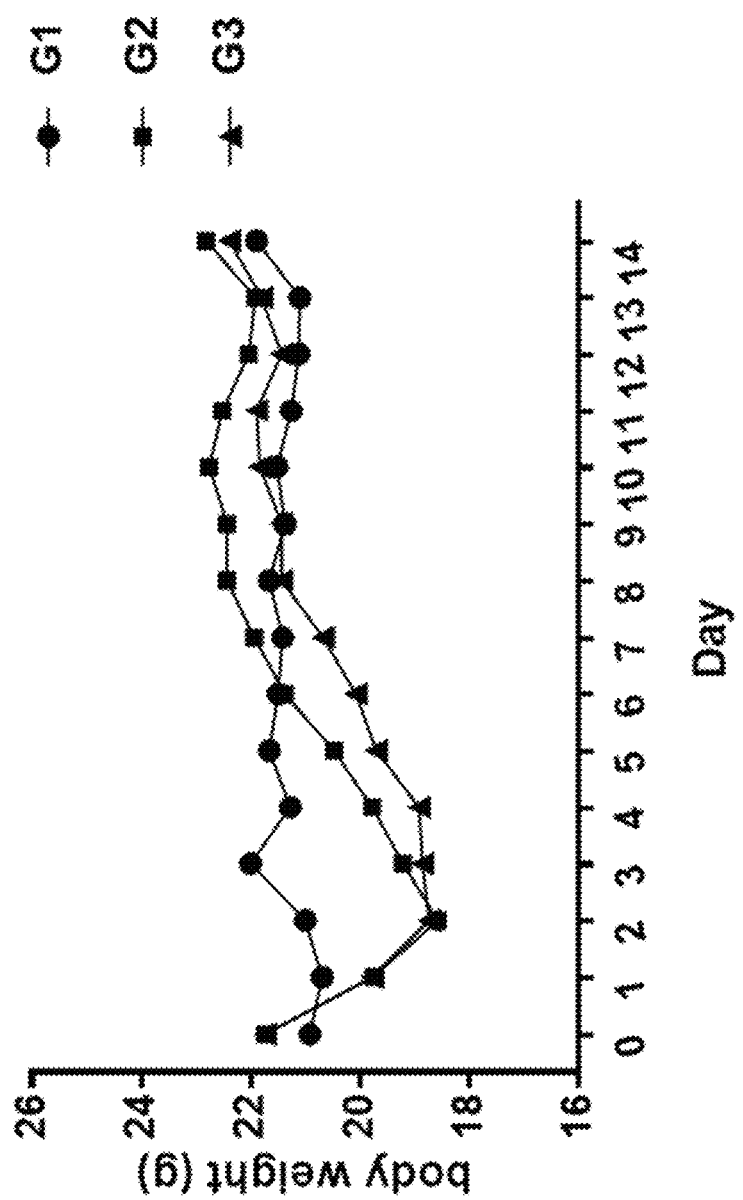

FIG. 24: A statistical graph of body weights of mice in the control group (G1), model group (G2) and anti-human IL-17A antibody treatment group (G3), in imiquimod-induced psoriasis model of mice homozygous for humanized IL-17A gene.

Figure 25:
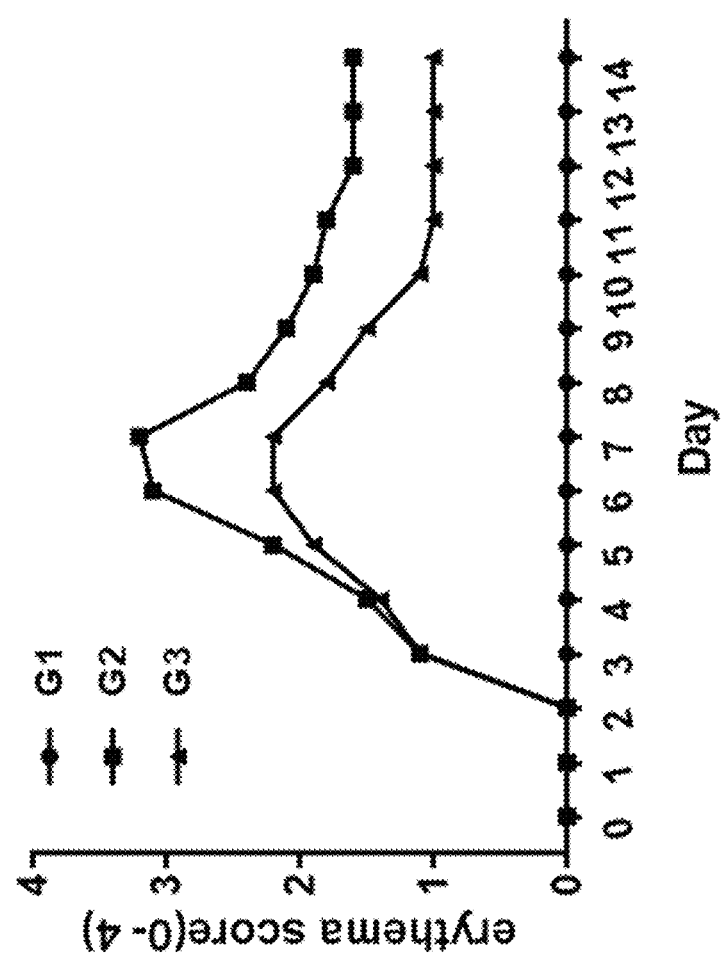

FIG. 25: A statistical graph of erythema scores on psoriasis-like lesions of mice in the control group (G1), model group (G2) and anti-human IL-17A antibody treatment group (G3), in imiquimod-induced psoriasis model of mice homozygous for humanized IL-17A gene.

Figure 26:
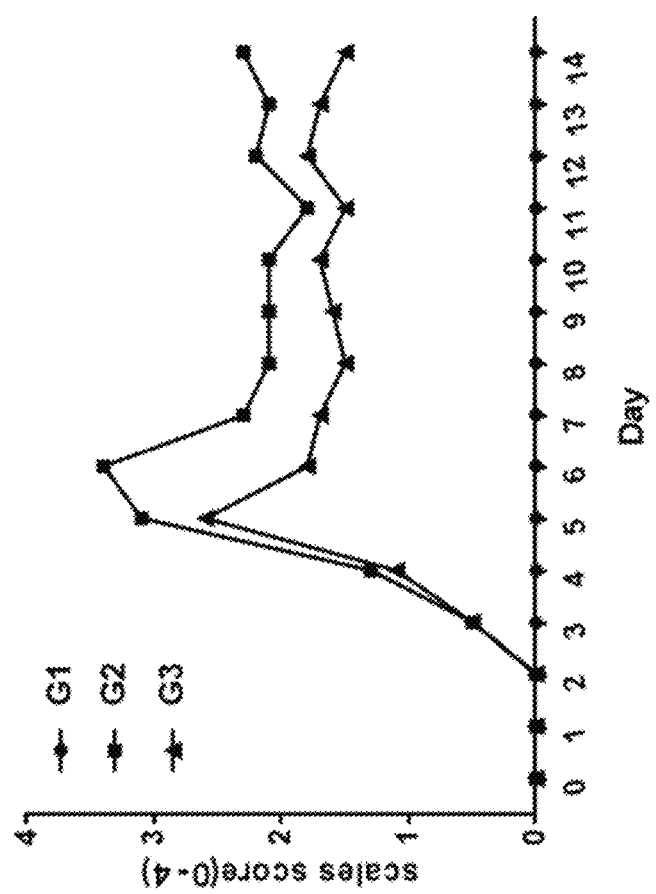

FIG. 26: A statistical graph of psoriasis-like scales scores of mice in the control group (G1), model group (G2) and anti-human IL-17A antibody treatment group (G3), in imiquimod-induced psoriasis model of mice homozygous for humanized IL-17A gene.

Figure 27:
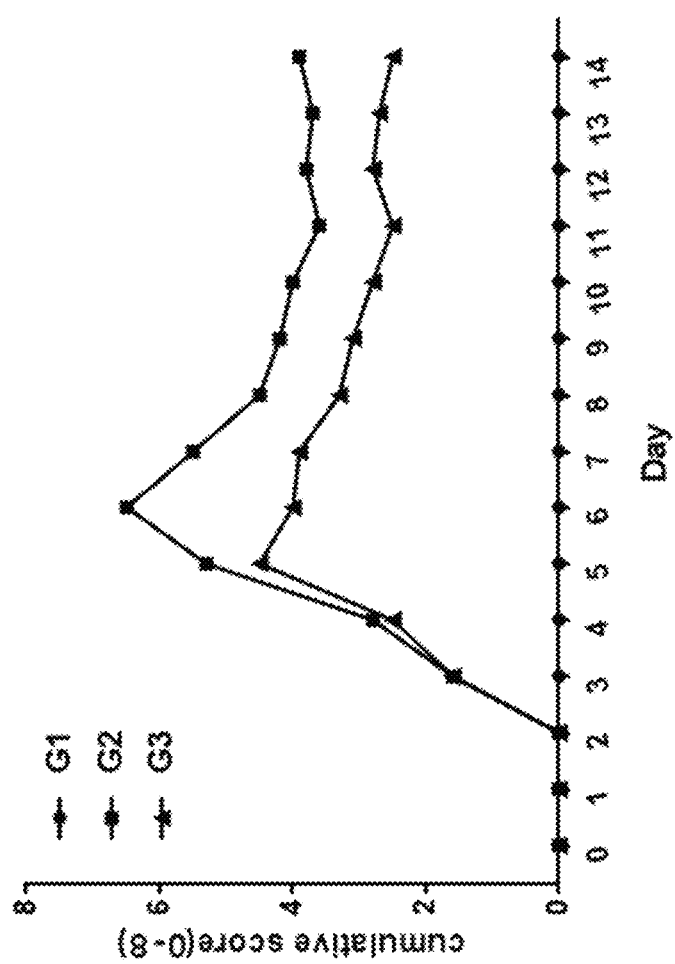

FIG. 27: A statistical graph of PASI scores of mice in the control group (G1), model group (G2) and anti-human IL-17A antibody treatment group (G3), in imiquimod-induced psoriasis model of mice homozygous for humanized IL-17A gene.

Figure 28:
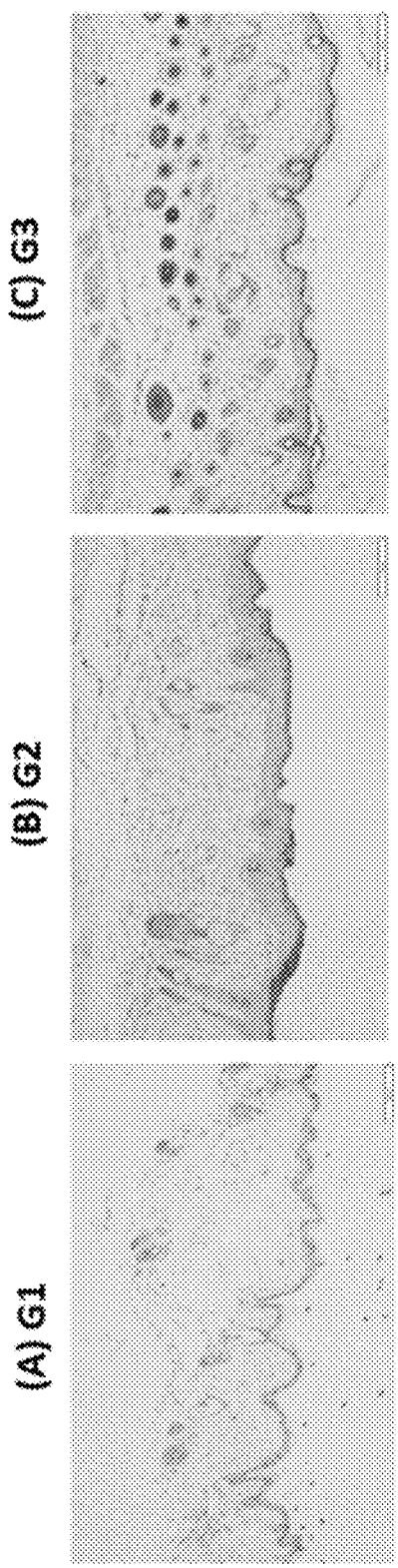

FIG. 28: HE staining results of the dorsal tissue sections of mice in the control group (G1), model group (G2) and anti-human IL-17A antibody treatment group (G3), in imiquimod-induced psoriasis model of mice homozygous for humanized IL-17A gene.

Figure 29:
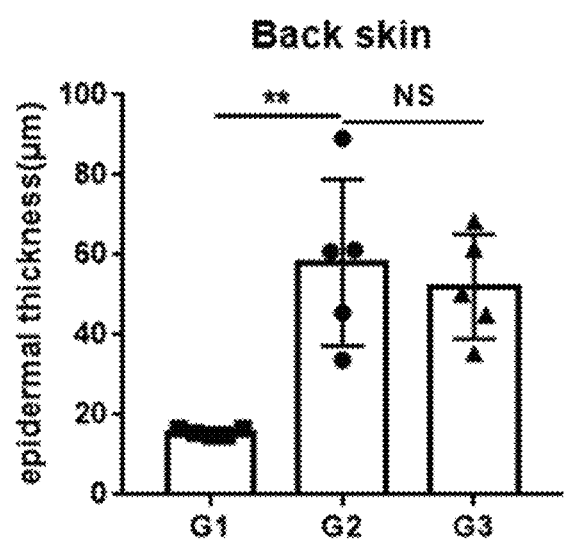

FIG. 29: A statistical graph of the epidermal thickness of the back tissue of mice in the control group (G1), model group (G2) and anti-human IL-17A antibody treatment group (G3), in imiquimod-induced psoriasis model of mice homozygous for humanized IL-17A gene.

Figure 30:
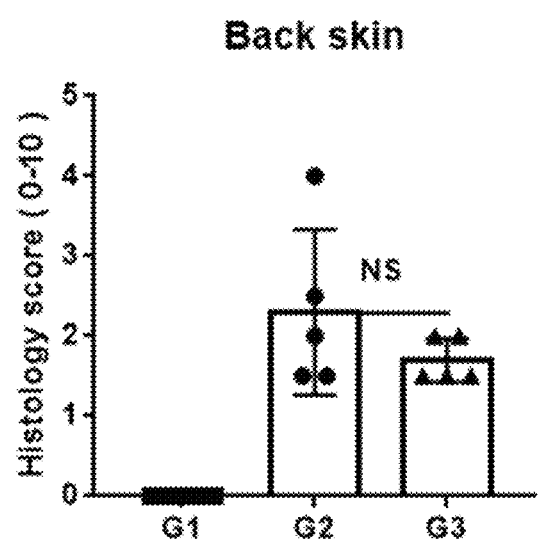

FIG. 30: A statistical graph of the pathological scores of the back skin sections of mice in the control group (G1), model group (G2) and anti-human IL-17A antibody treatment group (G3), in imiquimod-induced psoriasis model of mice homozygous for humanized IL-17A gene.

Figure 31:
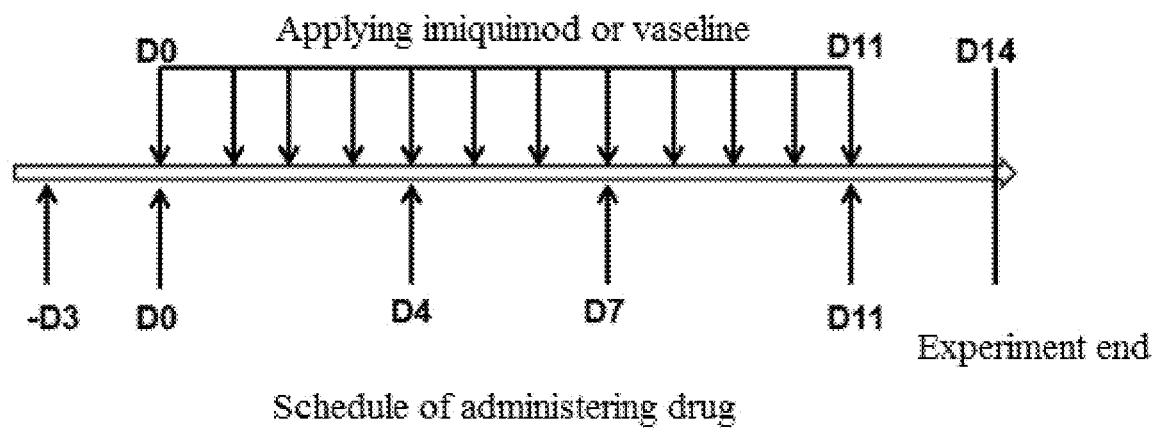

FIG. 31: Experimental flow chart of evaluating the effectiveness of different doses of anti-human IL-17A antibody in imiquimod-induced psoriasis model of mice homozygous for humanized IL-17A gene.

Figure 32:
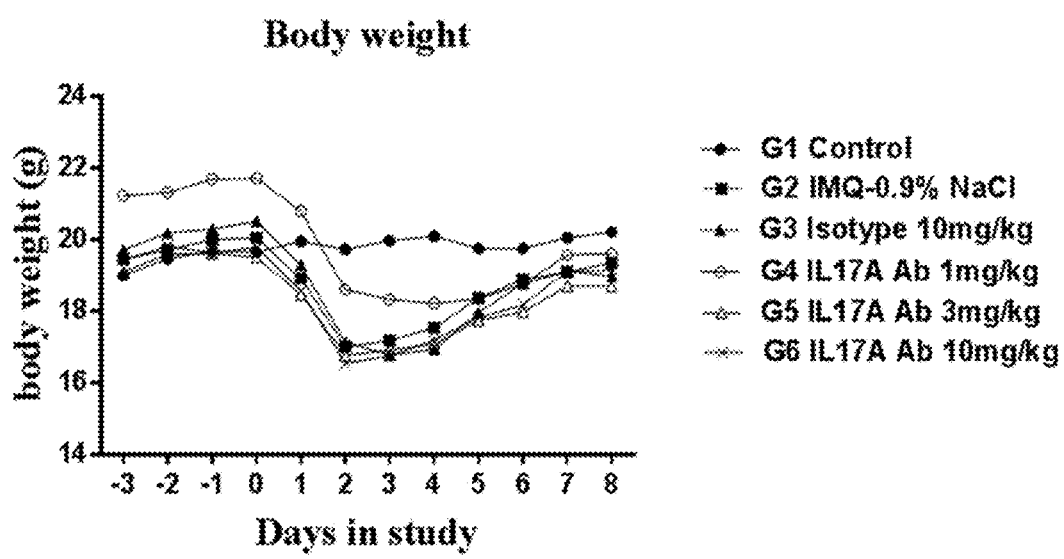

FIG. 32: A statistical graph of body weights of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

Figure 33:
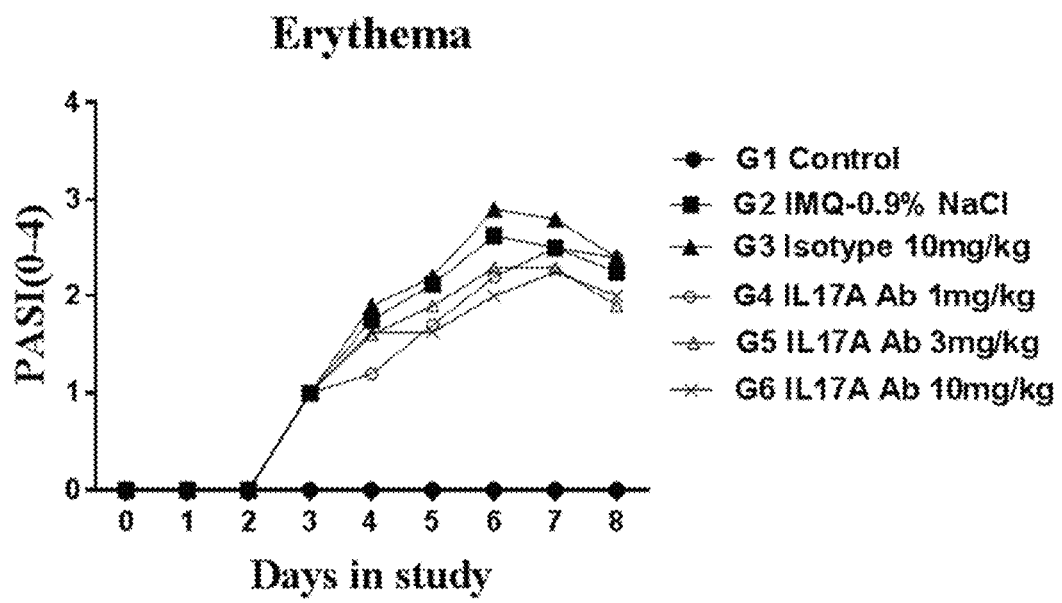

FIG. 33: A statistical graph of erythema scores on psoriasis-like lesions of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

Figure 34:
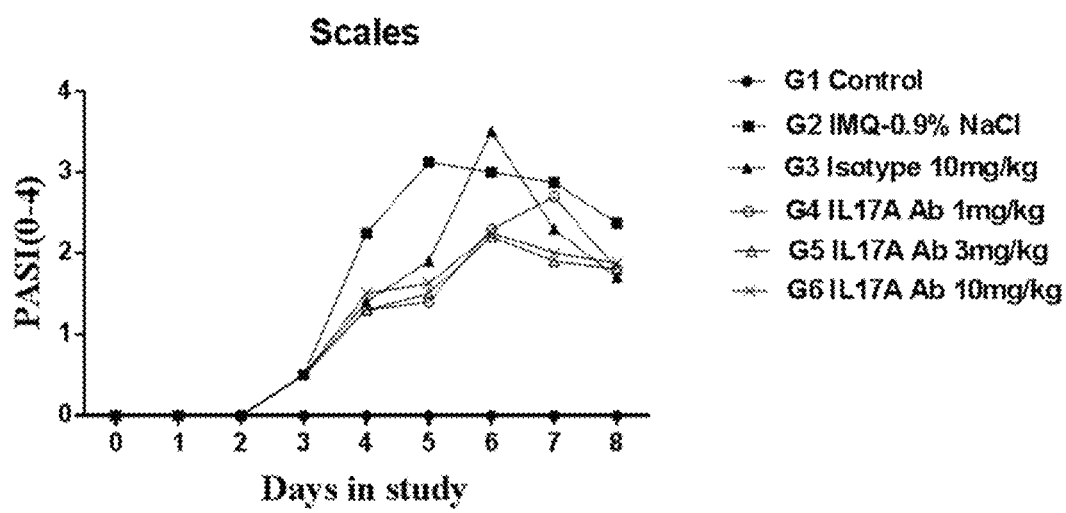

FIG. 34: A statistical graph of psoriasis-like scales scores of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

Figure 35:
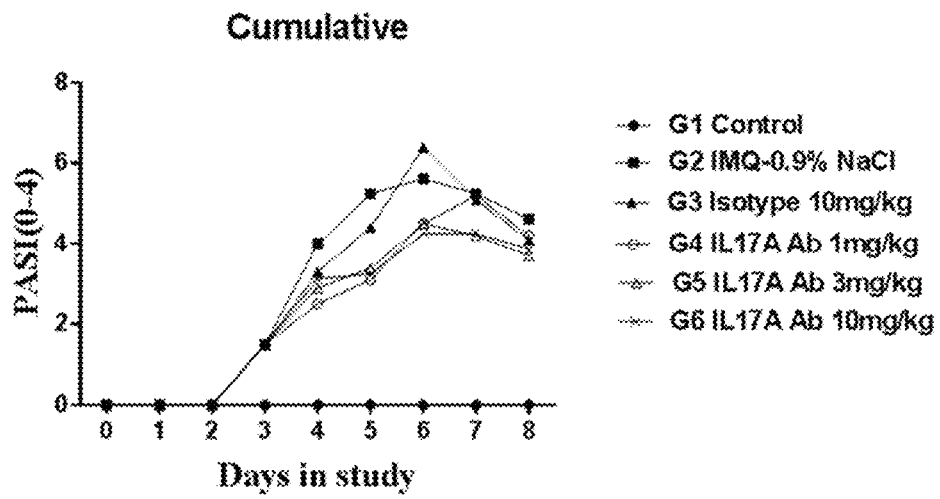

FIG. 35: A statistical graph of PASI scores of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

Figure 36:
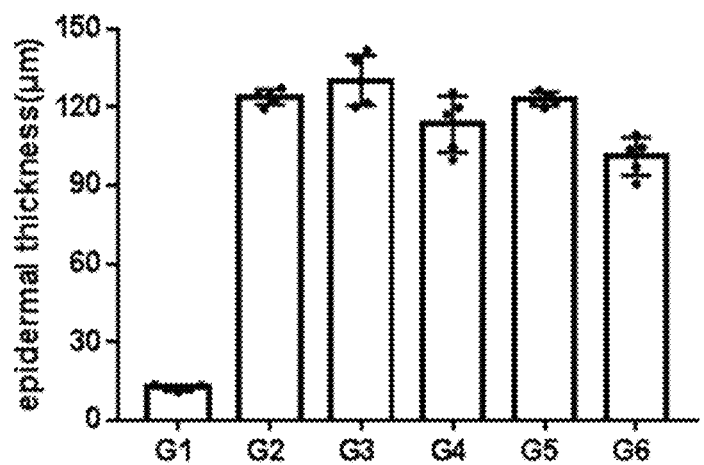

FIG. 36: A statistical graph of the epidermal thickness of the back tissue of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

Figure 37:
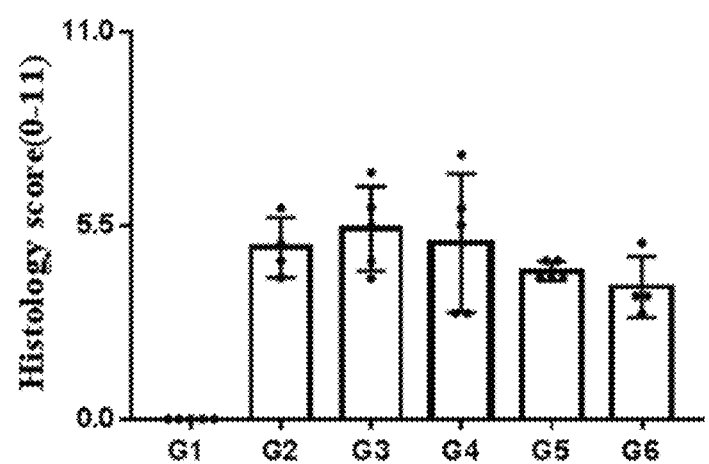

FIG. 37: A statistical graph of the pathological scores of the back skin sections of mice in the blank control group (G1), NaCl control group (G2), $IgG_4$ isotype control group (G3) and treatment groups of anti-human IL-17A antibody at different concentrations (G4-G6), in imiquimod-induced psoriasis model of mice homozygous for humanized IL-17A gene.

SEQUENCE LISTING

The instant application contains a Sequence Listing which has been submitted electronically in ASCII format and is hereby incorporated by reference in its entirety. Said ASCII copy, created on Nov. 19, 2019, is named Revised Sequence Listing.txt and is 129,510 bytes in size.

DETAILED DESCRIPTION

The invention will be further described below in conjunction with specific examples, and the advantages and characteristics of the invention will become clearer with the description. However, these examples are only exemplary and do not constitute any limitation to the scope of the invention. Those skilled in the art should understand that the details and forms of the technical solution of the invention can be modified or replaced without departing from the spirit and scope of the invention, and these modifications and replacements fall within the protection scope of the invention.

In the following examples, the equipment and materials were obtained from the companies indicated below.

EcoRI, ScaI, HindIII, amHI, XhoI, EcoRV, SalI and BbsI enzymes were purchased from NEB, with catalog numbers R3101M, R3122M, R3104M, R3136M, R0146M, R3195M, R3138M and R0539L, respectively.

C57BL/6 mice were purchased from the National Resource Center for Rodent Laboratory Animal of the National Institutes for Food and Drug Control, China.

Mouse MC38 colon cancer cells were purchased from Shanghai Biological Technology Co., Ltd. enzyme research.

The BAC library was purchased from Invitrogen, with catalog numbers RPCI23.0 and RPCI11.C.

BV711 hamster anti-mouse CD3e (mCD3) was purchased from BD, with catalog number 63123.

Flow cytometer was purchased from BD, with model Calibur.

IL-17A ELISA kit was purchased from Biolegend, with catalog number 433917.

CD217 (IL-17Ra) monoclonal antibody (PM-17R), PE (mIL17RA PE) was purchased from ebioscience, with catalog number 12-7182-80.

CD217 (IL-17Ra) monoclonal antibody (J10MBS), PE (hIL17RA PE) was purchased from ebioscience, with catalog number 12-7517-41.

APC anti-mouse Ly-6G/Ly-6C (Gr-1) antibody (mGR1PerCP) was purchased from Biolegend, with catalog number 108412.

PE anti-human IL-17A antibody (anti-human IL-17A PE) was purchased from Biolegend, with catalog number 512305.

APC anti-mouse IFN-γ antibody (anti-mouse IFN-γAPC) was purchased from Biolegend, with catalog number 505809.

Alexa Fluor® 488 anti-mouse CD3 antibody was purchased from Biolegend, with catalog number 100212.

Brilliant Violet 421™ anti-mouse CD4 antibody was purchased from Biolegend, with catalog number 100443.

Brilliant Violet 510™ anti-mouse CD45 antibody was purchased from Biolegend, with catalog number 103137.

eBioscience™ Foxp3/Transcription Factor Staining Buffer Set was purchased from ThermoFisher, with catalog number 00-5523-00.

Imiquimod cream (Aldara) was purchased from 3M Health Care Limited, with specification 250 mg: 12.5 mg, and approval number H20160079.

MOG35-55 was purchased from Pro Spec, with specification 100 mg.

Pertussis toxin (PTX) was purchased from Millipore, with catalog number 516560.

Example 1

IL-17A Gene Humanized Mice

Figure 1:
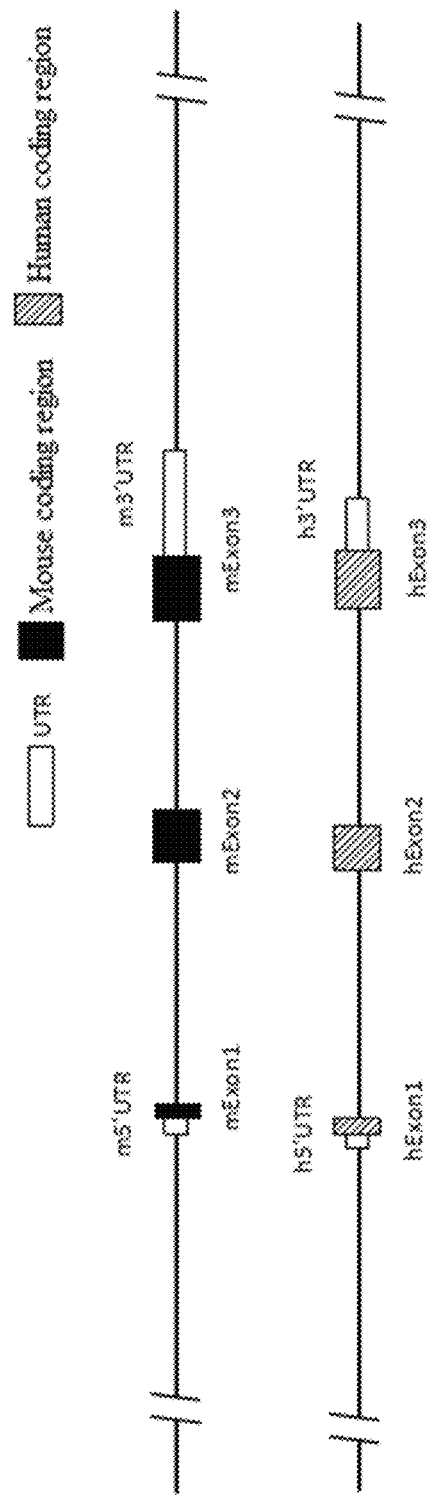
FIG. 1: Schematic diagram showing mouse IL-17A gene locus and human IL-17A gene locus (not to scale).

The mouse IL-17A gene (NCBI Gene ID: 16171, Primary source: MGI: 107364, UniProt ID: Q62386, located at 20730905 to 20734496 of chromosome 1 NC_000067.6, based on the transcript NM_010552.3 (SEQ ID NO: 1) and encoded protein NP_034682.1 (SEQ ID NO: 2)) and human IL-17A gene (NCBI Gene ID: 3605, Primary source: HGNC: 5981, UniProt ID: Q16552, located at 52186387 to 52190638 of chromosome 6 NC_000006.12, based on the transcript NM_002190.3 (SEQ ID NO: 3) and encoded protein NP_002181.1 (SEQ ID NO: 4)) is shown in FIG. 1.

Figure 2:
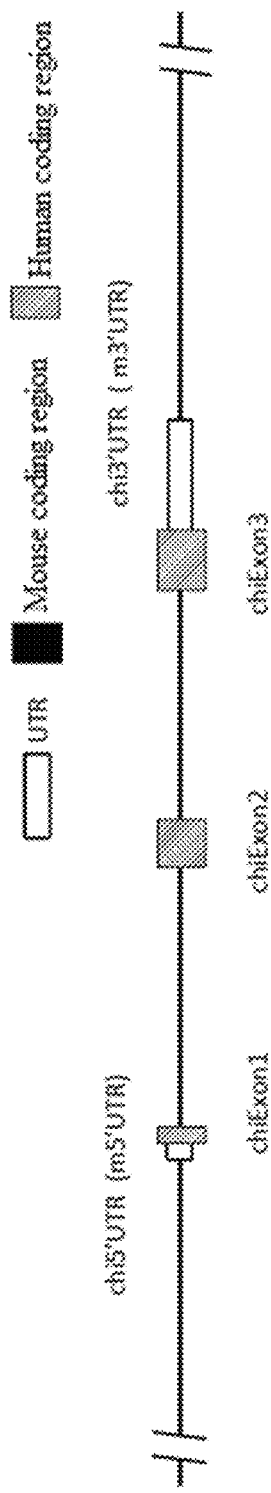
FIG. 2: Schematic diagram showing humanized mouse IL-17A gene (not to scale).

In order to achieve the purpose of the disclosure, a sequence encoding human IL-17A protein can be introduced into the mouse endogenous IL-17A locus, such that the mouse can express human IL-17A protein. Specifically, gene editing technology can be used to replace the specific mouse IL-17A gene sequence on the mouse endogenous IL-17A locus with a human IL-17A gene sequence, for example, replace the about 2.9 kb (2898 bp) sequence containing at least the start codon ATG to the stop codon TAA of the mouse IL-17A gene with the corresponding human DNA sequence to obtain a humanized IL-17A locus (as shown schematically in FIG. 2), to realize the humanization of mouse IL-17A gene.

Figure 3:
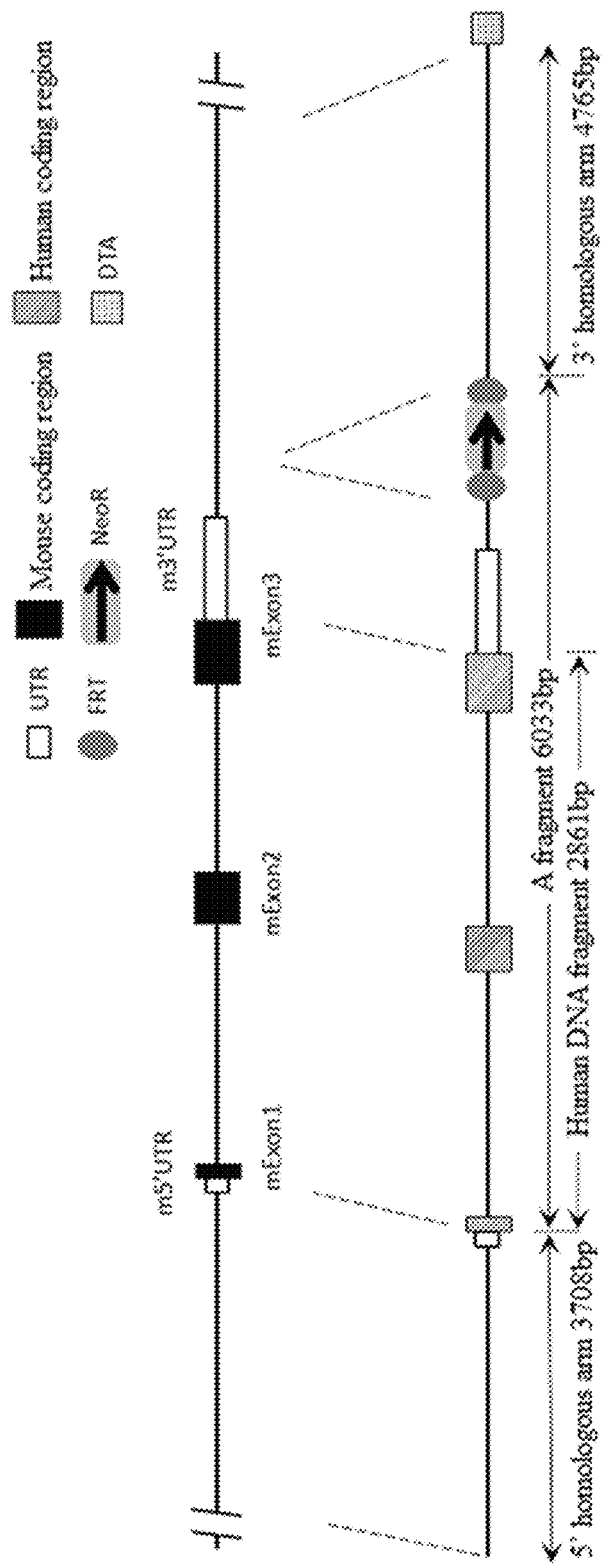
FIG. 3: Schematic diagram showing the targeting strategy for replacing the endogenous IL-17A gene sequence in mice with a targeting vector containing the human IL-17A gene sequence (not to scale).

Bacterial Artificial Chromosome (BAC) was used to obtain the DNA sequences of mouse and human IL-17A genes, respectively. In the schematic diagram of the targeting strategy shown in FIG. 3, it shows the 3708 bp and 4765 bp upstream and downstream homology arm sequences and the 2861 bp sequence of the human IL-17A gene (extended from the ATG in exon 1 to the stop codon TAA in exon 3) on the targeting vector. The upstream homology arm sequence (5' homology arm, SEQ ID NO: 5) is identical to the 20727254-20730961 of NC_000067.6, the downstream homology arm sequence (3'homology arm, SEQ ID NO: 6) is identical to the 20735137-20739901 of NC_000067.6, and the sequence of the human IL-17A gene (SEQ ID NO: 7) is identical to the 52186432-52189292 of NC_000006.12. The connection sequence of the human IL-17A gene and the mouse locus upstream is designed as 5'-GC-ACCCAGCACCAGCTGATCAGGACGCG<u>CAAACAT GAC</u>TCCTGGGAAGACCTCATTG GTG-3' (SEQ ID NO: 8), in which the last "C" of the sequence "CAAAC" is the last nucleotide of the mouse sequence, and the first "A" of the sequence "ATGAC" is the first nucleotide of the human sequence. The connection sequence of the human IL-17A gene and the mouse locus downstream is designed as 5'-CGATTGTCCACCATGTGG<u>CCTAAACAGAG</u>ACCC GCGGCTGACCCCTAAGA-3'(SEQ ID NO: 9), in which the last "A" of the sequence "CCTAA" is the last nucleotide of the human sequence, and the first "A" of the sequence "ACAGA" is the first nucleotide of the mouse sequence. The mRNA sequence and the encoded protein sequence of the modified humanized mouse IL-17A are shown in SEQ ID NO: 66 and SEQ ID NO: 4, respectively.

In addition, the targeting vector also includes an antibiotic resistance gene for positive clone screening (neomycin phosphotransferase coding sequence Neo) and two FRT recombination sites on both sides of the antibiotic resistance gene that formed a Neo cassette. The connection sequence between the 5'end of the Neo cassette and the mouse locus is designed as 5'-CCGGTGGACACATCTGGAGTACAG CG<u>TCTGCGTCGAC</u>GGTATCGATAAGCTTGATATCGA ATTCCGAAGTTCCTATTCTCTAG-3' (SEQ ID NO: 10), in which the last "C" of the sequence "TCTGC" is the last nucleotide of the mouse sequence, and the first "G" of the sequence "GTCGA" is the first nucleotide of the Neo cassette. The connection sequence between the 3' end of the Neo cassette and the mouse locus is designed as 5'-AGTATAGGAACTTCATCAGTCAGGTACATAATGG TGGATCCA<u>CTAGTATCTG</u>TAGCTCGGGGAACATCA TGAGAGAGGAGC-3'(SEQ ID NO: 11), in which the last "T" of the sequence "CTAGT" is the last nucleotide of the Neo cassette, and the "A" of the sequence "ATCTG" is the first nucleotide of the mouse sequence. In addition, a coding sequence for a negative selectable marker, that is, the coding sequence for diphtheria toxin A subunit (DTA) was designed downstream of the 3'homology arm of the targeting vector.

Figure 4:
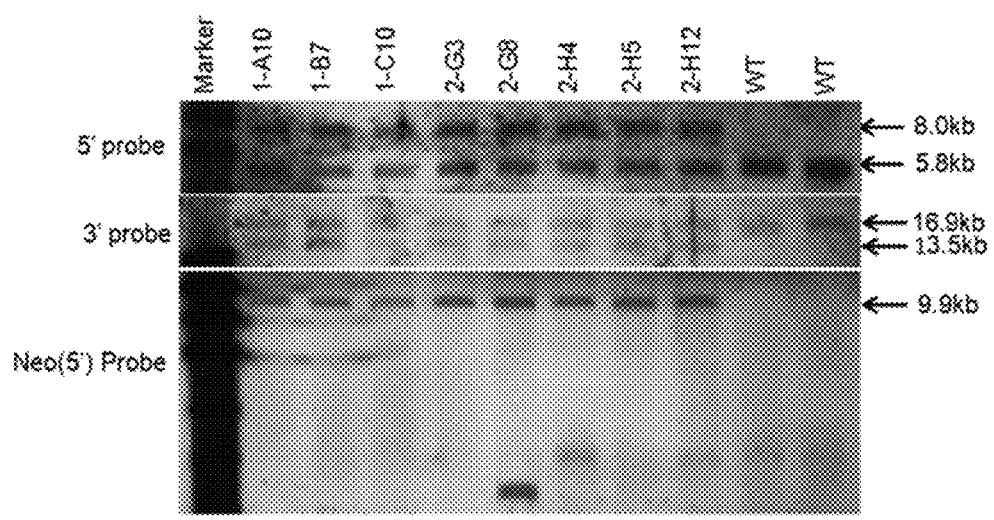
FIG. 4: Southern Blot results from different positive cell colonies, in which WT is wild-type control.

The vector can be constructed by conventional methods, such as restriction digestion and ligation, and the like. The constructed targeting vector sequence can be initially verified by restriction digestion, followed the sequencing company for sequencing verification. The targeting vector verified by sequencing was transferred into embryonic stem cells of C57BL/6 mice by electroporation, and the obtained cells were screened by selectable marker for the positive clones, and the integration of foreign genes was confirmed by PCR and Southern Blot methods, to screen out the correct positive clones. The positive clones were identified by PCR (PCR results not shown) were then subjected to Southern Blot (DNA extracted from cells was digested with EcoRV or SpeI or SacI, and then hybridized with 3 probes). The results are shown in FIG. 4, and the detection results indicate that among the 8 clones that are positive in PCR, 6 clones (1-A10, 1-B7, 1-C10, 2-G3, 2-H5, 2-H12) are positive heterozygous clones without random insertion.

The following primers are used for PCR.

```
F1:
                                     (SEQ ID NO: 12)
5'-CTTCTGATACATATGCATCCACGTGC-3';

R1:
                                     (SEQ ID NO: 13)
5'-ATGCCCACGGTCCAGAAATACTAT-3';

F2:
                                     (SEQ ID NO: 14)
5'-GCTCGACTAGAGCTTGCGGA-3';

R2:
                                     (SEQ ID NO: 15)
5'-GTGAGAGCAGCAAGTGCTCTTAACC-3'.
```

The following probes are used for Southern Blot.

```
5'Probe:
F:
                                     (SEQ ID NO: 16)
5'-AGAGCAGCATACCAATTAGCAACAT-3';

R:
                                     (SEQ ID NO: 17)
5'-CTAGGTGGGTTCCTCACTGGTCT-3'.

3'Probe:
F:
                                     (SEQ ID NO: 18)
5'-ACCAAAGGAACAAGTGGAAAGAATCGG-3';

R:
                                     (SEQ ID NO: 19)
5'-ATCTTCCTGCCCAGCATTGCCT-3'.

Neo Probe:
F:
                                     (SEQ ID NO: 20)
5'-GGATCGGCCATTGAACAAGATGG-3';

R:
                                     (SEQ ID NO: 21)
5'-CAGAAGAACTCGTCAAGAAGGCG-3'.
```

Figure 5:
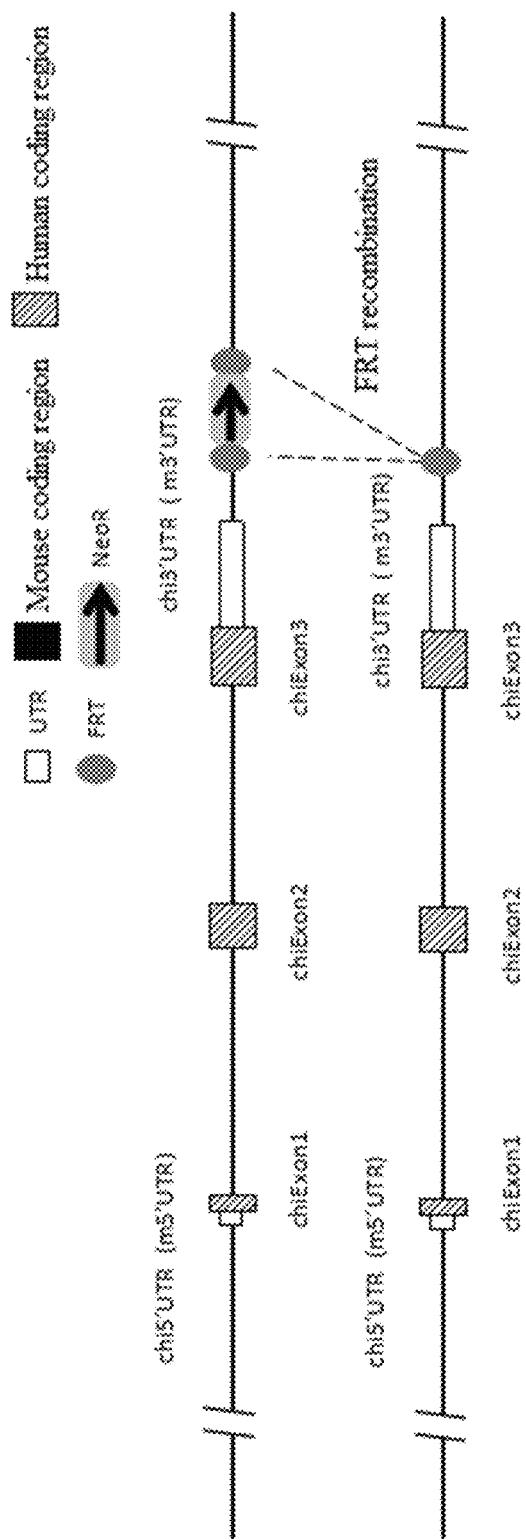
FIG. 5: Schematic diagram showing the FRT recombination process (not to scale).
Figure 6:
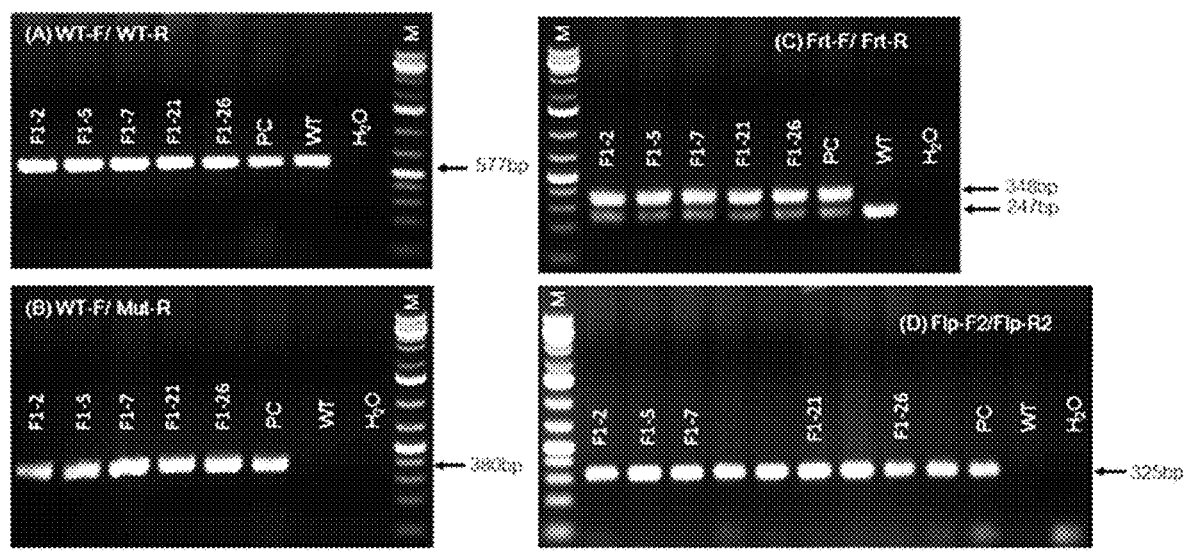
FIG. 6: tail vein PCR identification results for F1 generation mice, in which, panel (A), use primer pair WT-F and WT-R to amplify the endogenous mouse wild-type IL-17A gene fragment; panel (B), use primer pair WT-F and Mut-R to amplify the modified IL-17A gene fragment to verify whether the targeting vector is correctly inserted into the mouse genome site.

According to the technique known in the art, the positive colonies (from black mouse) were selected and introduced into the isolated blastocyst (from white mouse), and the obtained chimeric blastocyst was transferred to the culture medium for short-term culture and then transplanted into the oviduct of the recipient mother mouse (white mouse) to produce F0 generation chimeric mouse (black and white chequered). The F0 generation chimeric mice and wild-type mice were backcrossed to obtain F1 generation mice, and then F1 generation heterozygous mice were mated with each other to obtain F2 generation homozygous mice. The positive mouse can also be bred with the Flp tool mouse to remove the selectable marker gene from the positive clone (the process diagram is shown in FIG. 5), and then mated with each other to obtain the IL-17A gene humanized homozygous mouse expressing human IL-17A protein. The genotypes of the somatic cells of the offspring mice can be identified by PCR. The identification results of exemplary F1 generation mice (the Neo marker gene removed) are shown in FIG. 6, in which mice numbered F1-2, F1-5, F1-7, F1-21, F1-26 are positive heterozygous mice. The following primers are used for PCR.

```
WT-F:
                                     (SEQ ID NO: 22)
5'-TCTCTGTTCAGCTCCCAAGAAGTCA-3';

WT-R:
                                     (SEQ ID NO: 23)
5'-CTCATTGCATAGCGTCATGTGACA-3';

WT-F: SEQ ID NO: 22;

Mut-R:
                                     (SEQ ID NO: 24)
5'-ATGCCCACGGTCCAGAAATACTAT-3';

Frt-F:
                                     (SEQ ID NO: 25)
5'-GAATGTAGCTAGCCTGTGCAAGGA-3';

Frt-R:
                                     (SEQ ID NO: 26)
5'-CAGCAGACTTCCTGTTGTTCTGCTC-3';

Flp-F2:
                                     (SEQ ID NO: 27)
5'-GACAAGCGTTAGTAGGCACATATAC-3';

Flp-R2:
                                     (SEQ ID NO: 28)
5'-GCTCCAATTTCCCACAACATTAGT-3'.
```

Through this method, it is possible to construct a humanized IL-17A gene genetically-modified mouse without random insertion that can be stably passaged.

The expression of human IL-17A protein in the obtained positive mice can be confirmed by routine detection methods, for example, using the ELISA method. One wild-type C57BL/6 mouse and one mouse heterozygous for humanized IL-17A gene were selected, and 7.5 μg anti-mouse CD3 antibody (mCD3) and 4 μg anti-mouse CD28 antibody (mCD28) were injected intraperitoneally into the mice. After 2 hours, the serum was collected and diluted 2 times, and then the level of human IL-17A protein was detected. The detection results (see FIG. 7) showed that no human or humanized IL-17A protein was detected in the wild-type C57BL/6 mice, while human IL-17A protein was detected in mouse heterozygous for humanized IL-17A gene.

Example 2

IL-17RA Gene Humanized Mice

Schematic diagram of mouse IL-17RA gene (NCBI Gene ID: 16172, Primary source: MGI: 107399, UniProt ID: Q60943, located at 120463181 to 120483731 of chromosome 6 NC_000072.6, based on the transcript NM_008359.2 (SEQ ID NO: 29) and encoded protein NP_032385.1 (SEQ ID NO: 30)) compared with human IL-17RA gene (NCBI Gene ID: 23765, Primary source: HGNC: 5985, UniProt ID: Q96F46, located at 17084959 to 17115694 of chromosome 22 NC_000022.11, based on the transcript NM_014339.6 (NM_014339.6) and encoded protein NP_055154.3 (SEQ ID NO: 32) is shown in FIG. 8.

In order to achieve the purpose of the disclosure, a sequence encoding human IL-17RA protein can be introduced into the extracellular region of the mouse endogenous IL-17RA locus, so that the mouse expresses human or humanized IL-17RA protein. Specifically, gene editing technology is used to modify mouse cells to replace the specific mouse IL-17RA gene sequence on the mouse endogenous IL-17RA locus with a human IL-17RA gene sequence. Under the control of the mouse IL-17RA gene regulatory element, for example, at least a 8.9 kb sequence from exon2 to exon 11 of the mouse IL-17RA gene was replaced with the corresponding human gene sequence to obtain the mouse humanized IL-17RA locus, as shown in FIG. 9.

Further, a target strategy as shown in FIG. 10 was designed. Bacterial artificial chromosome (BAC) was used to obtain the DNA sequences of mouse and human IL-17RA genes, respectively. The targeting vector shown in FIG. 10 contains a 5'homology arm (SEQ ID NO: 33), a 3'homology arm (SEQ ID NO: 34) and a human IL-17RA gene fragment (SEQ ID NO: 35), in which the 5'homology arm is identical to the 120467551-120472097 of NC_000072.6, the 3' homology arm is identical to the 120478869-120482476 of NC_000072.6, and the human IL-17RA gene fragment identical to the 17097068-17105932 of NC_000022.11. The connection between the sequence of the human IL-17RA gene and the mouse locus upstream is designed as 5'-CTTCCTTTCTTCCCACAGGGGCTGAACTGCACG GTCAAGAATAGTAAGTC-3'(SEQ ID NO: 36), in which the last "G" of the sequence "GGCTG" is the last nucleotide of the mouse sequence, and the first "A" of the sequence "AACTG" is the first nucleotide of the human sequence. The connection sequence between the human IL-17RA gene and the mouse locus downstream is designed as 5'-TGGTGGGCTCCGTCATCCTGCTCATCGTCTGTAT GACCTGGAGGCTTTCTGGTAAGGACT-3' (SEQ ID NO: 37), in which the last "C" of the sequence "TCGTC" is the last nucleotide of the human sequence, and the first "T" of the sequence "TGTAT" is the first nucleotide of the mouse sequence. The mRNA sequence and the encoded protein sequence of the modified humanized mouse IL-17RA are shown in SEQ ID NO: 38 and SEQ ID NO: 39, respectively.

The targeting vector also includes an antibiotic resistance gene for positive clone screening, (neomycin phosphotransferase coding sequence Neo), and two FRT recombination sites on both sides of antibiotic the resistance gene, which constitutes a Neo cassette. The connection sequence between the 5' end of the Neo cassette and the mouse IL-17RA locus is designed as 5'-AGGAGCAGACCCT-GAACTCACAAGGGAAGACCCTCACTCGATATCGA ATTCCGAAGTTCCTATTCTCTAGAAAGTATAGG-3' (SEQ ID NO: 40), in which the last "C" of the sequence "CACTC" is the last nucleotide of the mouse, and the "G" of the sequence "GATAT" is the first nucleotide of the Neo cassette. The connection sequence between the 3' end of the Neo cassette and the mouse IL-17RA locus is designed as 5'-GTATAGGAACTTCATCAGTCAGGTACATAATGGT GGATCCCAATTGTCCACCAGCTTTGTAGTCACAGG AGACCTAATCT-3'(SEQ ID NO: 41), in which the "G" of the sequence "AATTG" is the last nucleotide of the Neo cassette, and the "T" of the sequence "TCCAC" is the first nucleotide of the mouse sequence. In addition, a coding sequence for a negative selectable marker, that is, the coding sequence for diphtheria toxin A subunit (DTA) was designed downstream of the 3' homology arm of the targeting vector.

The targeting vectors can be constructed by conventional methods, such as restriction digestion and ligation, direct synthesis and the like. The constructed targeting vector sequence can be initially verified by restriction digestion, followed the sequencing company for sequencing verification. The targeting vector verified by sequencing was transferred into embryonic stem cells of C57BL/6 mice by electroporation, and the obtained cells were screened by selectable marker gene of the positive clones, and the integration of foreign genes was confirmed by PCR and Southern Blot methods, to screen out the correct positive clones. The positive clones that were identified by PCR were then subjected to Southern Blot (DNA extracted from cells was digested with PstI, MfeI or SspI, and hybridized with 3 probes). The Southern Blot results are shown in FIG. 11, and the detection results indicate that 12 clones identified as positive by PCR (1-A02, 1-B07, 1-D07, 1-E05, 1-F05, 1-G06, 2-A09, 2-A10, 2-D03, 2-E06, 2-F07, 2-G10) are all determined to be positive heterozygous clones without random insertion.

The following primers are used for PCR.

```
F1:
                                (SEQ ID NO: 42)
5'-GCTCGACTAGAGCTTGCGGA-3';

R1:
                                (SEQ ID NO: 43)
5'-TCTTAAGTAGCAGGCTCAGGAGGCC-3';

F2:
                                (SEQ ID NO: 44)
5'-GTTCACCAGCGTGAATGCTCACA-3';

R2:
                                (SEQ ID NO: 45)
5'-CTGTCAGAAGTTGGCAGCAGG-3'.
```

The following probes are used for Southern Blot.

```
5'Probe:
F:
                                (SEQ ID NO: 46)
5'-GGACTGGATGAGACAGCTCAAAGGG-3';

R:
                                (SEQ ID NO: 47)
5'-GCTGCTTACAGGGCTTCTTCCTCAA-3'.

3'Probe:
F:
                                (SEQ ID NO: 48)
5'-GAGACGCAATGGGCAGTTAGATTCC-3';

R:
                                (SEQ ID NO: 49)
5'-AAATGTTCCAGCACTTCCTGGGTGT-3'.

Neo Probe:
F: (SEQ ID NO: 20);

R: (SEQ ID NO: 21).
```

According to the methods described in Example 1, the blastocyst injection and progeny breeding were carried out to obtain heterozygous and homozygous mice for humanized IL-17RA gene expressing humanized IL-17RA protein. The genotypes of somatic cells in offspring mice can be identified by PCR. The identification results of exemplary F1 generation mice (Neo has been removed) are shown in FIG. 12, in which the mice numbered R-F1-1, R-F1-2, and R-F1-5 are positive heterozygous mice. The following primers are used for PCR.

```
WT-F:
                                (SEQ ID NO: 50)
5'-ACCACTCACCTCCTCTGCTGGA-3';

WT-R:
                                (SEQ ID NO: 51)
5'-CCTCATGGAGCACAGATGCCTAT-3';
```

-continued

WT-F: SEQ ID NO: 50;

Mut-R:
(SEQ ID NO: 52)
5'-CTGTCAGAAGTTGGCAGCAGG-3';

Frt-F:
(SEQ ID NO: 53)
5'-CAAACAGCAGCCTACACAACTTCAT-3';

Frt-R:
(SEQ ID NO: 54)
5'-CTAGGCAACACACCTTCTCCCTGT-3';

Flp-F2: SEQ ID NO: 27;

Flp-R2: SEQ ID NO: 28.

Through this method, a humanized IL-17RA gene genetically-modified mouse without random insertion that can be stably passaged was constructed.

The expression of humanized IL-17RA protein in mice can be confirmed by conventional detection methods, for example, the anti-mouse IL-17RA antibody mIL-17RA PE and the anti-mouse Gr-1 antibody mGR1PerCP, or the anti-human IL-17RA antibody hIL-17RA PE and anti-mouse Gr-1 antibody mGR1PerCP were used to identify and stain the bone marrow cells of mice, and then a flow cytometry was used to detect the expression of IL-17RA protein. The flow analysis result is shown (see FIG. 13). In the spleen of mice heterozygous for humanized IL-17RA gene, cells expressing murine IL-17RA protein (FIG. 13B) and humanized IL-17RA protein (FIG. 13D) were detected; while in the spleen of wild-type C57BL/6 mice, only murine IL-17RA protein was detected (FIG. 13A), and no cells expressing human or humanized IL-17RA protein were detected (FIG. 13C).

Example 3

TNF-α Gene Humanized Mice

Mouse TNF-α gene (NCBI Gene ID: 21926, Primary source: MGI: 104798, UniProt ID: P06804, located at 35199367 to 35202007 of 17 NC_000083.6, based on the transcript NM_013693.3 (SEQ ID NO: 55) and encoded protein NP_038721.1 (SEQ ID NO: 56)), human TNF-α gene (NCBI Gene ID: 7124, Primary source: HGNC: 11892, UniProt ID: P01375, located at 31575567 to 31575567 of chromosome 6 NC_000006.12, based on the transcript NM_000594.3 (SEQ ID NO: 57) and encoded protein NP_000585.2 (SEQ ID NO: 58)).

In order to achieve the purpose of the disclosure, a sequence encoding human TNF-α protein can be introduced into the endogenous mouse TNF-α locus so that the mouse expresses human TNF-α protein. Specifically, gene editing technology can be used to replace a specific mouse TNF-α gene sequence on the mouse endogenous TNF-α locus with a human TNF-α gene sequence, for example, replace the about 1.8 kb (1,796 bp) sequence containing at least the start codon ATG to the stop codon TAA of the mouse TNF-α gene with the corresponding human gene sequence to realize the humanization of the mouse TNF-α gene.

A targeting vector for homologous recombination was constructed, which contains an upstream homology arm sequence and a downstream homology arm sequence (the DNA sequence of 6,173 bp upstream and 4,033 bp downstream of the mouse endogenous TNF-α locus), and a sequence of the human TNF-α locus. The upstream homology arm sequence (5' homology arm, SEQ ID NO: 59) is identical to the 35209909-35203737 of NC_0000083.6, the downstream homology arm sequence (3' homology arm, SEQ ID NO: 60) is identical to the 35197201 to 35193169 of NC_0000083.6, and the DNA fragment containing the human TNF-α gene sequence (6,287 bp, SEQ ID NO: 61) is identical to the 31573694-31579980 of NC_000006.12.

The targeting vector also includes an antibiotic resistance gene for positive clone screening (neomycin phosphotransferase coding sequence Neo), and two LoxP recombination sites on both sides of the resistance gene, which constitutes a Neo cassette. The 5' end of the Neo cassette is directly connected to the DNA fragment sequence (SEQ ID NO: 61) containing human TNF-α, and the connection sequence between the 3' end of the Neo cassette and the mouse locus is designed as 5'-AATGTATGCTATACGAAGTTATT-AGGTCCCTCGAGGGGATCCGAATTCATCGGCTTCC TCCTGGAACTCCTCCTCCTCG-3'(SEQ ID NO: 62), in which the last "T" of the sequence "GAATT" is the last nucleotide of the Neo cassette, and the first "C" of the sequence "CATCG" is the first nucleoside of the mouse sequence acid. In addition, a coding sequence for a negative selectable marker, for example, the coding sequence for diphtheria toxin A subunit (DTA) was designed downstream of the 3' homology arm of the targeting vector.

The vector can be constructed by conventional methods, such as restriction digestion and ligation and the like. After the constructed targeting vector was first verified by restriction digestion, it was sent to the sequencing company for sequencing verification. The targeting vector verified by sequencing was transferred into embryonic stem cells of C57BL/6 mice by electroporation, and the obtained cells were screened by selectable marker for the positive clones, and the integration of foreign genes was confirmed by PCR and Southern Blot methods, to screen out the correct positive clones. According to the method described in Example 1, the blastocyst injection and progeny breeding were carried out to obtain humanized TNF-α gene heterozygous and homozygous mice expressing human TNF-α protein. The genotype of the somatic cells of the offspring mouse can be identified by PCR. The identification result of an exemplary F1 generation mouse is shown in FIG. 14, in which the mouse numbered 10 is a positive heterozygous mouse. The following primers are used for PCR.

WT-F:
(SEQ ID NO: 63)
5'-GGTGACCTAGATAGTGCCTGG-3';

WT-R:
(SEQ ID NO: 64)
5'-TCAGTCGCAGGCACGTTAAG-3';

Neo-F:
(SEQ ID NO: 65)
5'-TGCATCGCATTGTCTGAGTAGG-3';

WT-R:
(SEQ ID NO: 64)
5'-TCAGTCGCAGGCACGTTAAG-3'.

Through this method, a humanized TNF-α gene genetically-modified mouse without random insertion that can be stably passaged was constructed.

Example 4

Production and Identification of Double Humanized or Multi-humanized Mice

The genetically-modified mice with humanized IL-17A gene, IL-17RA gene, or TNF-α gene produced by the method can also be used to produce mouse model with double humanized or multi-humanized genes. For example, in the above Example 1, the embryonic stem cells used for blastocyst microinjection can be selected from mice containing other genetic modifications. Alternatively, on the basis of genetically-modified mice with humanized IL-17A and/or IL-17RA and/or TNF-α, isolated mouse ES cells and gene homologous recombination technology can be used to obtain double-gene or multi-gene modified mouse model with modified IL-17A and/or IL-17RA and/or TNF-α genes and other gene.

The homozygous or heterozygous IL-17A and/or IL-17RA and/or TNF-α genetically-modified mice obtained by this method can also be bred with other genetically modified homozygous or heterozygous mice, and their offspring can be screened. According to Mendelian inheritance rules, there is a certain chance of getting double-gene or multi-gene modified heterozygous mice with humanized IL-17A and/or IL-17RA and/or TNF-α genes and other genetic modifications, and then the heterozygous mice can be bred with each other to obtain double-gene or multi-gene modified homozygous mice. These double-gene or multi-gene modified mice can be used for in vivo pharmacodynamics verification of regulators targeting human IL-17A and/or IL-17RA and/or TNF-α and other related signaling pathways.

For example, for L-17A/TNF-α genes double humanized mice, since the mouse IL-17A gene and TNF-α gene are located on chromosomes 1 and 17, respectively, the IL-17A gene humanized mice are bred with the TNF-α gene humanized mice, and the positive offspring mice are screened to finally obtain the IL-17A/TNF-α genes double humanized mice.

For example, for L-17A/IL-17RA genes double humanized mice, since the mouse IL-17A gene and IL-17RA gene are located on chromosomes 1 and 6, respectively, the IL-17A gene humanized mice are mated with the IL-17RA gene humanized mice, and the positive offspring mice are screened to finally obtain the IL-17A/IL-17RA genes double humanized mice.

Example 5

Establishment of EAE Disease Model Using Humanized Mice

The humanized mice disclosed in the disclosure can be used to produce a variety of human disease models, including multiple sclerosis, asthma, allergies, and other diseases, which can be used to test the in vivo effectiveness of human specific antibodies. For example, mice with humanized IL-17A and/or IL-17RA genes can be used to evaluate the pharmacodynamics, pharmacokinetics and in vivo therapeutic effectiveness of specific antagonists for human IL-17 signaling pathway in various disease models known in the art.

For example, for the production of Experimental Autoimmune Encephalomyelitis (EAE) model, the mice (about 10 weeks age) with humanized IL-17A, IL-17A/IL-17RA and other genes produced in the disclosure can be immunized with MOG once (on day 0, by subcutaneous injection of 200m/mouse), and given intraperitoneal injection of pertussis toxin (PTX) twice (day 0 and day 1, at a dose of 400m/mouse). After the first immunization, the mice were weighed and observed continuously every day. After the onset of the disease, the mice were divided into groups and administered drugs by gavage, intraperitoneal injection, or tail vein injection. Multiple detection indicators such as behavioral score, brain/spinal cord IHC pathology, HE pathology examination, detection of Th17 type cytokines of serum/brain homogenate, and flow cytometry of CNS, spleen, and lymph nodes maybe used to assess the in vivo effectiveness of different drugs for human.

In one study, the mouse homozygous for humanized IL-17A as described in Example 1 was used to establish an EAE disease model. The experimental groups are shown in Table 1. After immunization as described in the above method, none of the mice in the PBS control group (G1, G3) developed the disease, and only mice in the modeling group (G2, G4) were found to have the disease. The clinical symptoms included listlessness, weight loss, loss of tail tension, paralysis of hind limbs or extremities, incontinence, and ataxia developed in individual mice. A total of 10 mice in the two modeling groups developed the disease at 10-12 days after the first immunization, and had weight loss. With the increase in the number of days after sensitization, the number of cases gradually increased. The clinical symptoms reached a peak 3-5 days after the onset, and then entered a remission period, when the weight gradually increased, showing an "onset-remission" trend.

The incidence of female mice was compared with that of the male mice in the modeling group. Every day, animal body weight was measured and the neurological indicators were evaluated according to a 4-point scale (clinical score): 0, normal; 1, weak tail; 2, paralysis of partial hind limbs; 3, paralysis of all hind limbs; 4, paralysis of limbs. It was found that there was no significant difference in morbidity, onset time, peak time, and severity of symptom during the modeling process of both sexes, but the weight and clinical symptoms of female mice recovered better (see FIG. 15, FIG. 16). At the end of the experiment (the 45th day), the spinal cord tissues of female mice were fixed with paraformaldehyde, subjected to paraffin embeding and then sectioned, and stained with HE and IHC to observe histopathological changes. The longitudinal section of white matter of the lumbar enlargement of spinal cord was stained. As shown in FIG. 17 and FIG. 18, there are a large number of inflammatory cells infiltrated and myelin protein is greatly reduced in the spinal cord of MOG-immunized mice (modeling group). No abnormalities in the spinal cord of control mice.

TABLE 1

| Group | Immunogen | Age (weeks) | Number of mice | Gender | Genotype |
|---|---|---|---|---|---|
| G1(control group) | PBS | 10 | 4 | Female | IL17A (h/h) |
| G2(model group) | MOG | 10 | 5 | Female | IL17A (h/h) |
| G3(control group) | PBS | 10 | 5 | Male | IL17A (h/h) |
| G4(model group) | MOG | 10 | 5 | Male | IL17A (h/h) |

In the EAE model, IL-17A is mainly produced by CD4+ Th17 cells during the development of the disease. In order to detect the production of human IL-17 in mice, lymph node cells from MOG-immunized mice homozygous for humanized IL-17A (female, n=5) were isolated and stimulated with PMA and ionomycin in the presence of Brefeldin A for 6 hours. Cells producing IL-17 and IFNγ were analyzed by FACS. FIG. 19 shows exemplary flow cytometry results. The results show that the percentages of hIL-17+ CD3+CD4+ T cells and IFNγ+ T cells in CD3+CD4+ T cells in mouse lymph nodes increased after MOG immunization, which proved the successful establishment of EAE model in the molecular level.

The above results indicate that the genetically humanized mice produced by the methods of the disclosure can be used to establish a stable EAE model.

Example 6

Evaluation of In Vivo Effectiveness Using EAE Model of IL-17A Humanized Mice

The EAE model was established according to the method described in Example 5 using female IL-17A humanized mouse homozygotes. After the onset of disease, the mice were divided into groups and injected intraperitoneally with the anti-human IL-17A antibody Ixekizumab according to different dosing schedules; and the control group was injected with PBS. The experimental procedure is shown in FIG. 20, and the dosage regimen is shown in Table 2. Specifically, from the day of MOG immunization (day 0), the weights of the mice were recorded every day and the mice were clinically scored to observe the neurological performance. The mice were grouped on day 15. As shown in FIG. 21 and FIG. 22, compared with the control group, the weight loss of the mice in the treatment group was significantly alleviated, and the clinical scores were significantly reduced. In addition, the administration mode of the G2 group provides a better effect than that of the G3 and G4 groups. The above results indicate that the EAE model established using the IL-17A humanized mice of the disclosure can be used to evaluate the in vivo effectiveness of drugs targeting human IL-17A.

TABLE 2

| Group | Number of animals | Administration | Single dose (mg/kg) | Frequency | Dosing times |
|---|---|---|---|---|---|
| G1 | 6 | PBS | / | QW | 6 |
| G2 | 6 | Anti-human IL17A antibody | 15 | QW | 6 |
| G3 | 6 | Anti-human IL17A antibody | 15 | BIW | 6 |
| G4 | 6 | Anti-human IL17A antibody | 30 | QW | 6 |

BIW: once every two weeks, QW: once a week

Example 7

Establishment of Psoriasis Model Using IL-17A Humanized Mice And Evaluation of In Vivo Effectiveness Using The Model Toll-like receptors play an important role in the occurrence and development of psoriasis. Imiquimod is a Toll-like receptor agonist and can be used to model psoriasis. In this example, the humanized mouse homozygous for IL-17A as described in Example 1 was used to establish a psoriasis model by the method of imiquimod induction. The female IL-17A humanized mice were randomly divided into a control group (G1; no induction), a model group (G2) and a treatment group (G3), with 5 mice in each group. At the beginning of the experiment (−D3), the back hairs of the mice were removed with a shaver, exposing a 2 cm×3 cm skin area. After 3 days (D0), mice in the model group and the treatment group were administered with 5% Imiquimod (IMQ) cream (local dose 83 mg) to the back skin area every day for 12 consecutive days; and mice in the control group were administered with Vaseline. Mice in the treatment group were intraperitoneally injected with anti-human IL-17A antibody (Ixekizumab, 100 mg/kg single dose) at −D3, D0, D4, D7 and D11 for 5 times in total. The entire experiment period is 17 days, and the specific experiment scheme is shown in FIG. 23.

Starting from D0, the mice were weighed daily and photographed to observe the back skin conditions, and the clinical score of the condition of the mice was obtained. The scoring items include erythema and scales in mouse skin lesions. Each item is divided into 0-4 points according to the severity, based on the following PASI scoring standards: 0-none; 1-mild; 2-moderate; 3-severe; 4-extremely severe. For each group of mice, the score of each item or the average of the total scores of two items are compared. At the end of the experiment (D14), the skin specimens of the back and right ear of the mice were sliced and stained with hematoxylin and eosin (HE). The erosion, appearance of spinous processes, hypokeratosis, and mixed inflammatory cell infiltration on the back of each group of mice were scored according to the severity (0.5-2 points): 0.5-slight, 1-mild, 1.5-moderate, 2-severe. Stromal cell proliferation was scored (0.5-2 points): 0.5: 2-4 layers, 1: 4-6 layers, 1.5: 6-8 layers, and 2: 8-10 layers; the appearance of scabs: 0.5. Results statistics and pathological analysis scores between groups were performed, and the epidermal thickness was measured.

From the change of mouse body weight over time (FIG. 24), it can be seen that the weight of the control group was stable throughout the experimental period; and the weight trend of the model group and the treatment group was the same, that is, decreased firstly from D0, to the minimum around D2, and then slowly increased. During the experiment, there was little difference in body weight between the two groups. At the end of the experiment, the body weights of mice in all groups were close and had no significant difference. The results of back skin erythema, scaly and comprehensive PASI scores in FIGS. 25-27 show that none of the mice in the control group developed the disease, while the model group and the treatment group showed different degrees of disease. Comparing the model group and the treatment group, the skin PASI score of the mice in the treatment group is significantly lower than that of the model group, indicating that administration of anti-human IL-17A antibody to model mice has a therapeutic effect on psoriasis. The HE staining results of the back tissue sections of the mice (FIG. 28), the statistical results of the epidermal thickness of the back tissues (FIG. 29) and the pathological score statistical results of the back tissue sections (FIG. 30) showed that, the pathological changes of the back skin of the treatment group in terms of stromal cell proliferation and thickening of the epidermis were lower than those in the model group. In addition, some mice in the model group showed scabs on the back and ear skins, but no such lesions were seen in the treatment group, suggesting that the skin of the animals in the model group had ulceration or erosion, and the severity of the lesions was worse than that in the treatment group.

The above results demonstrate that the humanized mice of the disclosure can be used to establish a psoriasis model for evaluating the in vivo effectiveness of drugs targeting human IL-17A.

Example 8

Establishment of Psoriasis Model Using Humanized IL-17A Mice for Testing In Vivo Dose The humanized mouse homozygous for IL-17A as described in Example 1 was used to establish a psoriasis model by the method of imiquimod induction. Female mice were randomly divided into blank control G1 group (Vaseline; no induction of disease) and different treatment model groups (the following doses are single doses): control G2 group (0.9% NaCl), isotype control G3 group (10 mg/kg IgG$_4$), G4 group (1 mg/kg ixekizumab), G5 group (3 mg/kg ixekizumab), G6 group (10 mg/kg ixekizumab), with 5 animals in each group. At the beginning of the experiment (−D3), the back hairs were removed with a shaver, exposing a 2 cm×3 cm skin area. Three days later (D0), mice in the treatment group were administered with 5% imiquimod (IMQ) cream (local dose 80 mg) to the back skin area every day for 12 consecutive days; and mice in the G1 group were administered with Vaseline as a blank control. The treatment group was intraperitoneally injected with anti-human IL17A antibody (ixekizumab), 0.9% NaCl or IgG$_4$ every week from the beginning of the experiment (−D3) for a total of 5 administrations. The entire experimental period is 14 days, and the specific experimental scheme is shown in FIG. 31.

From the change of mouse body weight over time (FIG. 32), it can be seen that the weight of the control group was stable throughout the experimental period; the weight trend of the model group and the treatment group was the same, that is, decreased firstly from D0, to the minimum around D2, and then slowly increased. During the experiment, there was little difference in body weight between the two groups, and the weight of mice in all groups was similar and had no significant difference. The results of the erythema, scaly and comprehensive PASI score of the back skin in FIGS. 33-35 showed that none of the mice in the blank control group developed the disease, while the model groups treated with different treatments showed different degrees of skin diseases. The skin PASI score of mice (G4-G6) treated with the anti-human IL-17A antibody ixekizumab was lower than that of NaCl and IgG$_4$ treated mice, indicating that anti-human IL-17A antibody treatment in model mice alleviated the clinical signs of skin inflammation caused by imiquimod, and the treatment with 10 mg/kg ixekizumab had the best effect.

The statistical results of the epidermal thickness of the back tissues of the mice in each group (FIG. 36) show that the pathological changes of the back skin of the anti-human IL-17A antibody administration group in terms of stromal cell proliferation and epidermal thickening were lower than those of the NaCl and IgG$_4$ injection groups, indicating that the anti-human IL-17A antibody reduces the epidermal thickening of disease model mice. The pathological score statistical results of the back tissue sections of the mice are shown in FIG. 37. The pathological changes of the back skin of the treatment group in terms of stromal cell proliferation and epidermal thickening are lower than those of the model group. In addition, some mice in the model group showed scabs on the back and ear skins, but no such lesions were seen in the treatment group, suggesting that the skin of the animals in the model group had ulceration or erosion, and the severity of the lesions was higher than that in the treatment group. It shows that administration of mouse anti-human IL-17A antibody alleviated the signs of inflammation caused by imiquimod. Among them, treatment with a dose of 10 mg/kg ixekizumab had the best effect. The above results indicate that the humanized mice of the disclosure can be used to establish a psoriasis model to evaluate the in vivo dose of drugs targeting human IL-17A.

The preferred embodiments of the invention are described in detail above. However, the invention is not limited to the specific details in the above embodiments. Those skilled in the art will understand that within the scope of the technical concept of the invention, various modifications can be made to the technical solution of the invention, and these modifications all belong to the protection scope of the invention.

In addition, it should be noted that the various specific technical features described in the above specific embodiments can be combined in any suitable manner without contradiction. In order to avoid unnecessary repetition, various possible combinations are not described separately in the invention.

In addition, various different embodiments of the invention can also be combined arbitrarily, as long as they do not violate the spirit of the invention, and they should also be regarded as the disclosed content of the invention.

The invention claimed is:

1. A genetically-modified, non-human animal whose genome comprises a sequence encoding a humanized IL-17RA protein at an endogenous IL-17RA gene locus, wherein the sequence encoding the humanized IL-17RA protein is operably linked to an endogenous IL-17RA regulatory element at an endogenous IL-17RA gene locus, wherein the animal comprises a replacement of a part of exon 2, exons 3-10 and a part of exon 11 of the endogenous IL-17RA gene, with a part of exon 2, exons 3-10 and a part of exon 11 of a human IL-17RA gene, wherein the non-human animal detectably expresses the humanized IL-17RA protein on the surface of spleen cells, and the humanized IL-17RA protein comprises an amino acid sequence that is at least 95% identical SEQ ID NO: 39.

2. The animal of claim 1, wherein the humanized IL-17RA protein comprises SEQ ID NO: 39.

3. The animal of claim 1, wherein the genome of the animal further comprises a sequence encoding a human IL-17A protein, wherein the sequence encoding the human IL-17A protein is operably linked to an endogenous 5'UTR at an endogenous IL-17A gene locus.

4. The animal of claim 3, wherein the human IL-17A protein comprises an amino acid sequence that is at least 80% identical to SEQ ID NO: 4.

5. The animal of claim 3, wherein the human IL-17A protein comprises SEQ ID NO: 4.

6. The animal of claim 3, wherein the animal expresses the human IL-17A protein.

7. The animal of claim 3, wherein the animal is a rodent.

8. The animal of claim 3, wherein the animal is a mouse.

9. The animal of claim 3, whose genome comprises a replacement of a sequence encoding an endogenous IL-17A protein with a sequence encoding the human IL-17A protein.

10. The animal of claim 3, wherein the animal further comprises a sequence encoding a human TNF-α protein.

11. A method for making a genetically-modified non-human animal, comprising:
(a) replacing in a fertilized egg or an embryonic stem cell, at an endogenous IL-17RA gene locus, a part of exon 2, exons 3-10, and a part of exon 11 of endogenous IL-17RA gene with a part of exon 2, exons 3-10 and a part of exon 11 of a human IL-17RA gene;
(b) transplanting the fertilized egg of step (a) into a female non-human animal or transplanting the embryonic stem cell of step (a) into a blastocyst, which is then transferred into a female non-human animal; and
(c) obtaining a genetically-modified, non-human animal, wherein the non-human animal has genome that comprises a sequence encoding a humanized IL-17RA protein that is operably linked to an endogenous IL-17RA regulatory element at an endogenous IL-17RA gene locus.

12. The method of claim 11, wherein the humanized IL-17RA protein comprises an amino acid sequence that is at least 95% identical SEQ ID NO: 39.

13. The method of claim 11, wherein the humanized IL-17RA protein comprises SEQ ID NO: 39.

14. The method of claim 11, wherein the non-human animal detectably expresses the humanized IL-17RA protein on the surface of spleen cells.

* * * * *